(12) United States Patent
Inouye et al.

(10) Patent No.: US 8,765,921 B2
(45) Date of Patent: Jul. 1, 2014

(54) COELENTERAZINE ANALOGS AND MANUFACTURING METHOD THEREOF

(71) Applicants: JNC Corporation, Tokyo (JP); Tokyo Institute of Technology, Tokyo (JP)

(72) Inventors: Satoshi Inouye, Kanagawa (JP); Yuiko Sahara, Kanagawa (JP); Rie Iimori, Tokyo (JP); Takamitsu Hosoya, Tokyo (JP)

(73) Assignees: JNC Corporation, Tokyo (JP); Tokyo Institute of Technology, Tokyo (JP)

( * ) Notice: Subject to any disclaimer, the term of this patent is extended or adjusted under 35 U.S.C. 154(b) by 0 days.

(21) Appl. No.: 13/973,477

(22) Filed: Aug. 22, 2013

(65) Prior Publication Data
US 2014/0024058 A1    Jan. 23, 2014

Related U.S. Application Data

(62) Division of application No. 13/146,784, filed as application No. PCT/JP2010/051807 on Feb. 8, 2010, now Pat. No. 8,546,568.

(30) Foreign Application Priority Data

Feb. 9, 2009    (JP) ................................. 2009-027921

(51) Int. Cl.
| | | |
|---|---|---|
| G01N 21/76 | (2006.01) | |
| G01N 33/53 | (2006.01) | |
| C07D 487/04 | (2006.01) | |
| C12Q 1/66 | (2006.01) | |

(52) U.S. Cl.
USPC ........... 530/409; 544/350; 544/336; 544/349; 530/350; 530/402; 436/172; 436/79

(58) Field of Classification Search
USPC .......... 544/350, 336, 349; 530/350, 402, 409; 436/172, 79
See application file for complete search history.

(56) References Cited

U.S. PATENT DOCUMENTS

| | | |
|---|---|---|
| 7,268,229 B2 | 9/2007 | Wood et al. |
| 2003/0153090 A1 | 8/2003 | Wood et al. |
| 2006/0234324 A1 | 10/2006 | Inouye et al. |
| 2006/0246534 A1 | 11/2006 | Inouye et al. |
| 2008/0076156 A1 | 3/2008 | Inouye et al. |

FOREIGN PATENT DOCUMENTS

| | | |
|---|---|---|
| JP | 2005-515977 A | 6/2005 |
| JP | 2006-271327 A | 10/2006 |
| JP | 2006-308501 A | 11/2006 |
| WO | WO-01/46691 A1 | 6/2001 |
| WO | 2008-099669 A | 5/2008 |

OTHER PUBLICATIONS

International Search Report mailed Apr. 27, 2010 in PCT/JP2010/051807 filed Feb. 8, 2010.
M. Kuse et al., "Synthesis of 13C-Dehydrocoelenterazine and NMR Studies on the Bioluminescence of a Sympiectoteuthis Model", Tetrahedron, vol. 56, No. 17, pp. 2629-2639, 2000.
K. Teranishi et al., "Bioluminescence of the arm light organs of the luminous squid *Watasenia scintillans*", Biochimica et Biophysica Acta, vol. 1780, No. 5, pp. 784-792, Feb. 2008.
M. Adamczyk et al., "Synthesis of 3,7-dihydroimidazo[1,2a]pyrazine-3-ones and their chemiluminescent properties", Tetrahedron, vol. 59, No. 14, pp. 8129-8142, 2003.
T. Hirano et al., "Chemi- and Bioluminescence of Coelenterazine Analogues Possessing an Adamantylmethyl Group", Tetrahedron, vol. 53, No. 38, pp. 12903-12916, 1997.
T. Hirano et al., "Bioluminescent Properties of Fluorinated Semi-synthetic Aequorins", Tetrahedron Letters, vol. 39, pp. 5541-5544, 1998.
O. Shimomura et al., "Semi-synthetic aequorins with improved sensitivity to Ca2+ ions", Biochem. J., vol. 261, No. 3, pp. 913-920, 1989.
S. Inouye at al., "The Use of *Renilla* Luciferase, *Oplophorus* Luciferase, and Apoaequorin as Bioluminescent Reporter Protein in the Presence of Coelenterazine Analogues as Substrate", Biochemical and Biophysical Research Communications, vol. 233, No. 2, pp. 349-353, 1997.
S. Inouye et al., "Overexpression, purification and characterization of the catalytic component of *Oplophorus* luciferase in the deep-sea shrimp, *Oplophorus gracilirostris*", Protein Expression and Purification, vol. 56, pp. 261-268, 2007.
J. Levi at al. "Bisdeoxycoelenterazine Derivatives for Improvement of Bioluminescence Resonance Energy Transfer Assays", Journal of American Chemical Society, vol. 129, No. 39, pp. 11900-11901, 2007.
M. Isobe et al., "Synthesis of 13C-Dehydrocoelenterazine and Model Studies on *Symplectoteuthis* Squid Bioluminescence", Bioorganic & Medicinal Chemistry Letters, vol. 8, pp. 2919-2924, 1998.

(Continued)

*Primary Examiner* — Sreeni Padmanabhan
*Assistant Examiner* — Irina Neagu
(74) *Attorney, Agent, or Firm* — Drinker Biddle & Reath LLP

(57) ABSTRACT

There has been a need for coelenterazine analogs that exhibit luminescence properties different from those of known coelenterazine analogs. The present invention provides the compound represented by general formula (1).

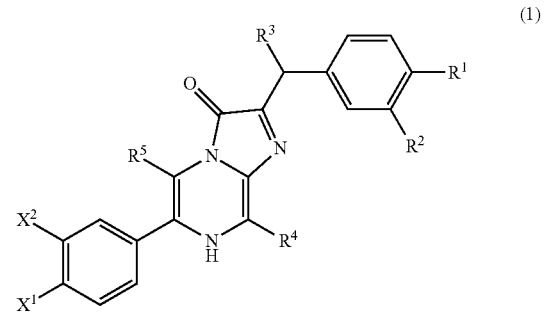

(1)

1 Claim, 7 Drawing Sheets

(56) References Cited

OTHER PUBLICATIONS

M. Isobe et al., "Chemistry of photoproteins as interface between bioactive molecules and protein function", Pure & Applied Chemistry, vol. 70, No. 11, pp. 2085-2092, 1998.

O. Shimomura et al., "Semi-synthetic aequorin", Biochem. J., vol. 251, No. 2, pp. 405-410, 1988.

S. Inouye, "Identification of two catalytic domains in a luciferase secreted by the copepod *Gaussia princeps*", Biochemical and Biophysical Research Communications, vol. 365, No. 1, pp. 96-101, 2008.

S. Inouye, "Expression, purification and characterization of calcium-triggered luciferin-binding protein of *Renilla reniformis*", Protein Expression and Purification, vol. 52, No, 1, pp. 66-73, 2007.

S. Inouye, "Cloning, Expression, Purification and Characterization of an Isotype of Clytin, a Calcium-Binding Photoprotein from the Luminous Hydromedusa *Clytia gregarium*", J. Biochem., vol. 143, No. 5, pp. 711-717, 2008.

```
SEQUENCE LISTING

<160> NUMBER OF SEQ ID NOS: 18

<210> SEQ ID NO 1
<211> LENGTH: 591
<212> TYPE: DNA
<213> ORGANISM: Aequorea victoria
<220> FEATURE:
<221> NAME/KEY: CDS
<222> LOCATION: (1)..(591)

<400> SEQUENCE: 1 atg aca agc aaa caa tac tca gtc aag ctt aca tca gac ttc gac aac    48
Met Thr Ser Lys Gln Tyr Ser Val Lys Leu Thr Ser Asp Phe Asp Asn
1               5                   10                  15 cca aga tgg att gga cga cac aag cat atg ttc aat ttc ctt gat gtc    96
Pro Arg Trp Ile Gly Arg His Lys His Met Phe Asn Phe Leu Asp Val
            20                  25                  30 aac cac aat gga aaa atc tct ctt gac gag atg gtc tac aag gca tct   144
```

```
                Asn His Asn Gly Lys Ile Ser Leu Asp Glu Met Val Tyr Lys Ala Ser
                             35                  40                  45 gat att gtc atc aat aac ctt gga gca aca cct gag caa gcc aaa cga         192
Asp Ile Val Ile Asn Asn Leu Gly Ala Thr Pro Glu Gln Ala Lys Arg
 50                  55                  60 cac aaa gat gct gta gaa gcc ttc ttc gga gga gct gga atg aaa tat         240
His Lys Asp Ala Val Glu Ala Phe Phe Gly Gly Ala Gly Met Lys Tyr
 65                  70                  75                  80 ggt gtg gaa act gat tgg cct gca tat att gaa gga tgg aaa aaa ttg         288
Gly Val Glu Thr Asp Trp Pro Ala Tyr Ile Glu Gly Trp Lys Lys Leu
                     85                  90                  95 gct act gat gaa ttg gag aaa tac gcc aaa aac gaa cca acg ctc atc         336
Ala Thr Asp Glu Leu Glu Lys Tyr Ala Lys Asn Glu Pro Thr Leu Ile
                100                 105                 110 cgt ata tgg ggt gat gct ttg ttt gat atc gtt gac aaa gat caa aat         384
Arg Ile Trp Gly Asp Ala Leu Phe Asp Ile Val Asp Lys Asp Gln Asn
            115                 120                 125 gga gcc att aca ctg gat gaa tgg aaa gca tac acc aaa gct gct ggt         432
Gly Ala Ile Thr Leu Asp Glu Trp Lys Ala Tyr Thr Lys Ala Ala Gly
        130                 135                 140 atc atc caa tca tca gaa gat tgc gag gaa aca ttc aga gtg tgc gat         480
Ile Ile Gln Ser Ser Glu Asp Cys Glu Glu Thr Phe Arg Val Cys Asp
145                 150                 155                 160 att gat gaa agt gga caa ctc gat gtt gat gag atg aca aga caa cat         528
Ile Asp Glu Ser Gly Gln Leu Asp Val Asp Glu Met Thr Arg Gln His
                    165                 170                 175 tta gga ttt tgg tac acc atg gat cct gct tgc gaa aag ctc tac ggt         576
Leu Gly Phe Trp Tyr Thr Met Asp Pro Ala Cys Glu Lys Leu Tyr Gly
                180                 185                 190 gga gct gtc ccc taa                                                     591
Gly Ala Val Pro
            195

<210> SEQ ID NO 2
<211> LENGTH: 196
<212> TYPE: PRT
<213> ORGANISM: Aequorea victoria

<400> SEQUENCE: 2

Met Thr Ser Lys Gln Tyr Ser Val Lys Leu Thr Ser Asp Phe Asp Asn
 1               5                  10                  15

Pro Arg Trp Ile Gly Arg His Lys His Met Phe Asn Phe Leu Asp Val
                20                  25                  30

Asn His Asn Gly Lys Ile Ser Leu Asp Glu Met Val Tyr Lys Ala Ser
             35                  40                  45

Asp Ile Val Ile Asn Asn Leu Gly Ala Thr Pro Glu Gln Ala Lys Arg
 50                  55                  60

His Lys Asp Ala Val Glu Ala Phe Phe Gly Gly Ala Gly Met Lys Tyr
 65                  70                  75                  80

Gly Val Glu Thr Asp Trp Pro Ala Tyr Ile Glu Gly Trp Lys Lys Leu
                     85                  90                  95

Ala Thr Asp Glu Leu Glu Lys Tyr Ala Lys Asn Glu Pro Thr Leu Ile
                100                 105                 110

Arg Ile Trp Gly Asp Ala Leu Phe Asp Ile Val Asp Lys Asp Gln Asn
            115                 120                 125

Gly Ala Ile Thr Leu Asp Glu Trp Lys Ala Tyr Thr Lys Ala Ala Gly
        130                 135                 140

Ile Ile Gln Ser Ser Glu Asp Cys Glu Glu Thr Phe Arg Val Cys Asp
```

```
                    145                 150                 155                 160
Ile Asp Glu Ser Gly Gln Leu Asp Val Asp Glu Met Thr Arg Gln His
                165                 170                 175
Leu Gly Phe Trp Tyr Thr Met Asp Pro Ala Cys Glu Lys Leu Tyr Gly
            180                 185                 190
Gly Ala Val Pro
        195

<210> SEQ ID NO 3
<211> LENGTH: 597
<212> TYPE: DNA
<213> ORGANISM: Clytia gregaria
<220> FEATURE:
<221> NAME/KEY: CDS
<222> LOCATION: (1)..(597)

<400> SEQUENCE: 3 atg gct gac act gca tca aaa tac gcc gtc aaa ctc aga ccc aac ttc        48
Met Ala Asp Thr Ala Ser Lys Tyr Ala Val Lys Leu Arg Pro Asn Phe
1               5                   10                  15 gac aac cca aaa tgg gtc aac aga cac aaa ttt atg ttc aac ttt ttg        96
Asp Asn Pro Lys Trp Val Asn Arg His Lys Phe Met Phe Asn Phe Leu
            20                  25                  30 gac att aac ggc gac gga aaa atc act ttg gat gaa atc gtc tcc aaa       144
Asp Ile Asn Gly Asp Gly Lys Ile Thr Leu Asp Glu Ile Val Ser Lys
        35                  40                  45 gct tcg gat gac att tgc gcc aaa ctt gga gca aca cca gaa cag acc       192
Ala Ser Asp Asp Ile Cys Ala Lys Leu Gly Ala Thr Pro Glu Gln Thr
    50                  55                  60 aaa cgt cac cag gat gct gtc gaa gct ttc ttc aaa aag att ggt atg       240
Lys Arg His Gln Asp Ala Val Glu Ala Phe Phe Lys Lys Ile Gly Met
65                  70                  75                  80 gat tat ggt aaa gaa gtc gaa ttc cca gct ttt gtt gat gga tgg aaa       288
Asp Tyr Gly Lys Glu Val Glu Phe Pro Ala Phe Val Asp Gly Trp Lys
                85                  90                  95 gaa ctg gcc aat tat gac ttg aaa ctt tgg tct caa aac aag aaa tct       336
Glu Leu Ala Asn Tyr Asp Leu Lys Leu Trp Ser Gln Asn Lys Lys Ser
            100                 105                 110 ttg atc cgc gac tgg gga gaa gct gtt ttc gac att ttt gac aaa gac       384
Leu Ile Arg Asp Trp Gly Glu Ala Val Phe Asp Ile Phe Asp Lys Asp
        115                 120                 125 gga agt ggc tca atc agt ttg gac gaa tgg aag gct tat gga cga atc       432
Gly Ser Gly Ser Ile Ser Leu Asp Glu Trp Lys Ala Tyr Gly Arg Ile
    130                 135                 140 tct gga atc tgc tca tca gac gaa gac gcc gaa aag acc ttc aaa cat       480
Ser Gly Ile Cys Ser Ser Asp Glu Asp Ala Glu Lys Thr Phe Lys His
145                 150                 155                 160 tgc gat ttg gac aac agt ggc aaa ctt gat gtt gat gag atg acc aga       528
Cys Asp Leu Asp Asn Ser Gly Lys Leu Asp Val Asp Glu Met Thr Arg
                165                 170                 175 caa cat ttg gga ttc tgg tac acc ttg gac ccc aac gct gat ggt ctt       576
Gln His Leu Gly Phe Trp Tyr Thr Leu Asp Pro Asn Ala Asp Gly Leu
            180                 185                 190 tac ggc aat ttt gtt cct taa                                            597
Tyr Gly Asn Phe Val Pro
        195

<210> SEQ ID NO 4
<211> LENGTH: 198
<212> TYPE: PRT
<213> ORGANISM: Clytia gregaria
```

-continued

```
<400> SEQUENCE: 4

Met Ala Asp Thr Ala Ser Lys Tyr Ala Val Lys Leu Arg Pro Asn Phe
1               5                   10                  15

Asp Asn Pro Lys Trp Val Asn Arg His Lys Phe Met Phe Asn Phe Leu
            20                  25                  30

Asp Ile Asn Gly Asp Gly Lys Ile Thr Leu Asp Glu Ile Val Ser Lys
        35                  40                  45

Ala Ser Asp Asp Ile Cys Ala Lys Leu Gly Ala Thr Pro Glu Gln Thr
    50                  55                  60

Lys Arg His Gln Asp Ala Val Glu Ala Phe Lys Lys Ile Gly Met
65                  70                  75                  80

Asp Tyr Gly Lys Glu Val Glu Phe Pro Ala Phe Val Asp Gly Trp Lys
                85                  90                  95

Glu Leu Ala Asn Tyr Asp Leu Lys Leu Trp Ser Gln Asn Lys Lys Ser
            100                 105                 110

Leu Ile Arg Asp Trp Gly Glu Ala Val Phe Asp Ile Phe Asp Lys Asp
        115                 120                 125

Gly Ser Gly Ser Ile Ser Leu Asp Glu Trp Lys Ala Tyr Gly Arg Ile
    130                 135                 140

Ser Gly Ile Cys Ser Ser Asp Glu Asp Ala Glu Lys Thr Phe Lys His
145                 150                 155                 160

Cys Asp Leu Asp Asn Ser Gly Lys Leu Asp Val Asp Glu Met Thr Arg
                165                 170                 175

Gln His Leu Gly Phe Trp Tyr Thr Leu Asp Pro Asn Ala Asp Gly Leu
            180                 185                 190

Tyr Gly Asn Phe Val Pro
        195

<210> SEQ ID NO 5
<211> LENGTH: 657
<212> TYPE: DNA
<213> ORGANISM: Clytia gregaria
<220> FEATURE:
<221> NAME/KEY: CDS
<222> LOCATION: (1)..(657)

<400> SEQUENCE: 5 atg tcg gct tta gct gca aga tca aga ttg caa cgc aca gca aat ttt    48
Met Ser Ala Leu Ala Ala Arg Ser Arg Leu Gln Arg Thr Ala Asn Phe
1               5                   10                  15 cac acc agc ata ctg ttg gct aca gat tca aaa tac gcg gtc aaa ctc    96
His Thr Ser Ile Leu Leu Ala Thr Asp Ser Lys Tyr Ala Val Lys Leu
            20                  25                  30 gat cct gat ttt gca aat cca aaa tgg atc aac aga cac aaa ttt atg   144
Asp Pro Asp Phe Ala Asn Pro Lys Trp Ile Asn Arg His Lys Phe Met
        35                  40                  45 ttc aac ttt ttg gac ata aac ggt aat ggg aaa atc aca tta gat gaa   192
Phe Asn Phe Leu Asp Ile Asn Gly Asn Gly Lys Ile Thr Leu Asp Glu
    50                  55                  60 atc gtc tcc aaa gct tca gac gac att tgt gct aaa ctg gat gca aca   240
Ile Val Ser Lys Ala Ser Asp Asp Ile Cys Ala Lys Leu Asp Ala Thr
65                  70                  75                  80 cca gaa cag acc aaa cgt cac cag gat gct gtt gaa gcg ttt ttc aag   288
Pro Glu Gln Thr Lys Arg His Gln Asp Ala Val Glu Ala Phe Phe Lys
                85                  90                  95 aaa atg ggc atg gat tat ggt aaa gaa gtt gca ttc cca gaa ttt att   336
Lys Met Gly Met Asp Tyr Gly Lys Glu Val Ala Phe Pro Glu Phe Ile
```

```
                  100                 105                 110
aag gga tgg gaa gag ttg gcc gaa cac gac ttg gaa ctc tgg tct caa         384
Lys Gly Trp Glu Glu Leu Ala Glu His Asp Leu Glu Leu Trp Ser Gln
        115                 120                 125 aac aaa agt aca ttg atc cgt gaa tgg gga gat gct gtt ttc gac att         432
Asn Lys Ser Thr Leu Ile Arg Glu Trp Gly Asp Ala Val Phe Asp Ile
130                 135                 140 ttc gac aaa gac gca agt ggc tca atc agt tta gac gaa tgg aag gct         480
Phe Asp Lys Asp Ala Ser Gly Ser Ile Ser Leu Asp Glu Trp Lys Ala
145                 150                 155                 160 tac gga cga atc tct gga atc tgt cca tca gac gaa gac gct gag aag         528
Tyr Gly Arg Ile Ser Gly Ile Cys Pro Ser Asp Glu Asp Ala Glu Lys
            165                 170                 175 acg ttc aaa cat tgt gat ttg gac aac agt ggc aaa ctt gat gtt gat         576
Thr Phe Lys His Cys Asp Leu Asp Asn Ser Gly Lys Leu Asp Val Asp
            180                 185                 190 gag atg acc agg caa cat tta ggc ttc tgg tac aca ttg gat cca act         624
Glu Met Thr Arg Gln His Leu Gly Phe Trp Tyr Thr Leu Asp Pro Thr
        195                 200                 205 tct gat ggt ctt tat ggc aat ttt gtt ccc taa                             657
Ser Asp Gly Leu Tyr Gly Asn Phe Val Pro
        210                 215

<210> SEQ ID NO 6
<211> LENGTH: 218
<212> TYPE: PRT
<213> ORGANISM: Clytia gregaria

<400> SEQUENCE: 6

Met Ser Ala Leu Ala Ala Arg Ser Arg Leu Gln Arg Thr Ala Asn Phe
1               5                   10                  15

His Thr Ser Ile Leu Leu Ala Thr Asp Ser Lys Tyr Ala Val Lys Leu
            20                  25                  30

Asp Pro Asp Phe Ala Asn Pro Lys Trp Ile Asn Arg His Lys Phe Met
        35                  40                  45

Phe Asn Phe Leu Asp Ile Asn Gly Asn Gly Lys Ile Thr Leu Asp Glu
    50                  55                  60

Ile Val Ser Lys Ala Ser Asp Asp Ile Cys Ala Lys Leu Asp Ala Thr
65                  70                  75                  80

Pro Glu Gln Thr Lys Arg His Gln Asp Ala Val Glu Ala Phe Phe Lys
                85                  90                  95

Lys Met Gly Met Asp Tyr Gly Lys Glu Val Ala Phe Pro Glu Phe Ile
            100                 105                 110

Lys Gly Trp Glu Glu Leu Ala Glu His Asp Leu Glu Leu Trp Ser Gln
        115                 120                 125

Asn Lys Ser Thr Leu Ile Arg Glu Trp Gly Asp Ala Val Phe Asp Ile
    130                 135                 140

Phe Asp Lys Asp Ala Ser Gly Ser Ile Ser Leu Asp Glu Trp Lys Ala
145                 150                 155                 160

Tyr Gly Arg Ile Ser Gly Ile Cys Pro Ser Asp Glu Asp Ala Glu Lys
                165                 170                 175

Thr Phe Lys His Cys Asp Leu Asp Asn Ser Gly Lys Leu Asp Val Asp
            180                 185                 190

Glu Met Thr Arg Gln His Leu Gly Phe Trp Tyr Thr Leu Asp Pro Thr
        195                 200                 205

Ser Asp Gly Leu Tyr Gly Asn Phe Val Pro
    210                 215
```

<210> SEQ ID NO 7
<211> LENGTH: 597
<212> TYPE: DNA
<213> ORGANISM: Mitrocoma cellularia
<220> FEATURE:
<221> NAME/KEY: CDS
<222> LOCATION: (1)..(597)

<400> SEQUENCE: 7

| | | | | | | | | | | | | | | | | |
|---|---|---|---|---|---|---|---|---|---|---|---|---|---|---|---|---|
| atg | tca | atg | ggc | agc | aga | tac | gca | gtc | aag | ctt | acg | act | gac | ttt | gat | 48 |
| Met | Ser | Met | Gly | Ser | Arg | Tyr | Ala | Val | Lys | Leu | Thr | Thr | Asp | Phe | Asp | |
| 1 | | | | 5 | | | | | 10 | | | | | 15 | | |
| aat | cca | aaa | tgg | att | gct | cga | cac | aag | cac | atg | ttc | aac | ttc | ctt | gac | 96 |
| Asn | Pro | Lys | Trp | Ile | Ala | Arg | His | Lys | His | Met | Phe | Asn | Phe | Leu | Asp | |
| | | | 20 | | | | | 25 | | | | | 30 | | | |
| atc | aat | tca | aat | ggc | caa | atc | aat | ctg | aat | gaa | atg | gtc | cat | aag | gct | 144 |
| Ile | Asn | Ser | Asn | Gly | Gln | Ile | Asn | Leu | Asn | Glu | Met | Val | His | Lys | Ala | |
| | | 35 | | | | | 40 | | | | | 45 | | | | |
| tca | aac | att | atc | tgc | aag | aag | ctt | gga | gca | aca | gaa | gaa | caa | acc | aaa | 192 |
| Ser | Asn | Ile | Ile | Cys | Lys | Lys | Leu | Gly | Ala | Thr | Glu | Glu | Gln | Thr | Lys | |
| 50 | | | | | 55 | | | | | 60 | | | | | | |
| cgt | cat | caa | aag | tgt | gtc | gaa | gac | ttc | ttt | ggg | gga | gct | ggt | ttg | gaa | 240 |
| Arg | His | Gln | Lys | Cys | Val | Glu | Asp | Phe | Phe | Gly | Gly | Ala | Gly | Leu | Glu | |
| 65 | | | | 70 | | | | | 75 | | | | | 80 | | |
| tat | gac | aaa | gat | acc | aca | tgg | cct | gag | tac | atc | gaa | gga | tgg | aag | agg | 288 |
| Tyr | Asp | Lys | Asp | Thr | Thr | Trp | Pro | Glu | Tyr | Ile | Glu | Gly | Trp | Lys | Arg | |
| | | | | 85 | | | | | 90 | | | | | 95 | | |
| ttg | gct | aag | act | gaa | ttg | gaa | agg | cat | tca | aag | aat | caa | gtc | aca | ttg | 336 |
| Leu | Ala | Lys | Thr | Glu | Leu | Glu | Arg | His | Ser | Lys | Asn | Gln | Val | Thr | Leu | |
| | | | 100 | | | | | 105 | | | | | 110 | | | |
| atc | cga | tta | tgg | ggt | gat | gct | ttg | ttc | gac | atc | att | gac | aaa | gat | aga | 384 |
| Ile | Arg | Leu | Trp | Gly | Asp | Ala | Leu | Phe | Asp | Ile | Ile | Asp | Lys | Asp | Arg | |
| | | 115 | | | | | 120 | | | | | 125 | | | | |
| aat | gga | tcg | gtt | tcg | tta | gac | gaa | tgg | atc | cag | tac | act | cat | tgt | gct | 432 |
| Asn | Gly | Ser | Val | Ser | Leu | Asp | Glu | Trp | Ile | Gln | Tyr | Thr | His | Cys | Ala | |
| | 130 | | | | | 135 | | | | | 140 | | | | | |
| ggc | atc | caa | cag | tca | cgt | ggg | caa | tgc | gaa | gct | aca | ttt | gca | cat | tgc | 480 |
| Gly | Ile | Gln | Gln | Ser | Arg | Gly | Gln | Cys | Glu | Ala | Thr | Phe | Ala | His | Cys | |
| 145 | | | | | 150 | | | | | 155 | | | | | 160 | |
| gat | tta | gat | ggt | gac | ggt | aaa | ctt | gat | gtg | gac | gaa | atg | aca | aga | caa | 528 |
| Asp | Leu | Asp | Gly | Asp | Gly | Lys | Leu | Asp | Val | Asp | Glu | Met | Thr | Arg | Gln | |
| | | | | 165 | | | | | 170 | | | | | 175 | | |
| cat | ttg | gga | ttt | tgg | tat | tcg | gtc | gac | cca | act | tgt | gaa | gga | ctc | tac | 576 |
| His | Leu | Gly | Phe | Trp | Tyr | Ser | Val | Asp | Pro | Thr | Cys | Glu | Gly | Leu | Tyr | |
| | | | 180 | | | | | 185 | | | | | 190 | | | |
| ggt | ggt | gct | gta | cct | tat | taa | | | | | | | | | | 597 |
| Gly | Gly | Ala | Val | Pro | Tyr | | | | | | | | | | | |
| | | | 195 | | | | | | | | | | | | | |

<210> SEQ ID NO 8
<211> LENGTH: 198
<212> TYPE: PRT
<213> ORGANISM: Mitrocoma cellularia

<400> SEQUENCE: 8

Met Ser Met Gly Ser Arg Tyr Ala Val Lys Leu Thr Thr Asp Phe Asp
1               5                   10                  15

Asn Pro Lys Trp Ile Ala Arg His Lys His Met Phe Asn Phe Leu Asp
            20                  25                  30

Ile Asn Ser Asn Gly Gln Ile Asn Leu Asn Glu Met Val His Lys Ala

```
                    35                  40                  45
Ser Asn Ile Ile Cys Lys Lys Leu Gly Ala Thr Glu Glu Gln Thr Lys
 50                  55                  60

Arg His Gln Lys Cys Val Glu Asp Phe Phe Gly Gly Ala Gly Leu Glu
 65                  70                  75                  80

Tyr Asp Lys Asp Thr Thr Trp Pro Glu Tyr Ile Glu Gly Trp Lys Arg
                     85                  90                  95

Leu Ala Lys Thr Glu Leu Glu Arg His Ser Lys Asn Gln Val Thr Leu
                100                 105                 110

Ile Arg Leu Trp Gly Asp Ala Leu Phe Asp Ile Ile Asp Lys Asp Arg
                115                 120                 125

Asn Gly Ser Val Ser Leu Asp Glu Trp Ile Gln Tyr Thr His Cys Ala
130                 135                 140

Gly Ile Gln Gln Ser Arg Gly Cys Glu Ala Thr Phe Ala His Cys
145                 150                 155                 160

Asp Leu Asp Gly Asp Gly Lys Leu Asp Val Asp Glu Met Thr Arg Gln
                165                 170                 175

His Leu Gly Phe Trp Tyr Ser Val Asp Pro Thr Cys Glu Gly Leu Tyr
                180                 185                 190

Gly Gly Ala Val Pro Tyr
            195

<210> SEQ ID NO 9
<211> LENGTH: 588
<212> TYPE: DNA
<213> ORGANISM: Obelia longissima
<220> FEATURE:
<221> NAME/KEY: CDS
<222> LOCATION: (1)..(588)

<400> SEQUENCE: 9 atg tct tca aaa tac gca gtt aaa ctc aag act gac ttt gat aat cca      48
Met Ser Ser Lys Tyr Ala Val Lys Leu Lys Thr Asp Phe Asp Asn Pro
  1               5                  10                  15 cga tgg atc aaa aga cac aag cac atg ttt gat ttc ctc gac atc aat      96
Arg Trp Ile Lys Arg His Lys His Met Phe Asp Phe Leu Asp Ile Asn
                 20                  25                  30 gga aat gga aaa atc acc ctc gat gaa att gtg tcc aag gca tct gat     144
Gly Asn Gly Lys Ile Thr Leu Asp Glu Ile Val Ser Lys Ala Ser Asp
             35                  40                  45 gac ata tgt gcc aag ctc gaa gcc aca cca gaa caa aca aaa cgc cat     192
Asp Ile Cys Ala Lys Leu Glu Ala Thr Pro Glu Gln Thr Lys Arg His
 50                  55                  60 caa gtt tgt gtt gaa gct ttc ttt aga gga tgt gga atg gaa tat ggt     240
Gln Val Cys Val Glu Ala Phe Phe Arg Gly Cys Gly Met Glu Tyr Gly
 65                  70                  75                  80 aaa gaa att gcc ttc cca caa ttc ctc gat gga tgg aaa caa ttg gcg     288
Lys Glu Ile Ala Phe Pro Gln Phe Leu Asp Gly Trp Lys Gln Leu Ala
                 85                  90                  95 act tca gaa ctc aag aaa tgg gca aga aac gaa cct act ctc att cgt     336
Thr Ser Glu Leu Lys Lys Trp Ala Arg Asn Glu Pro Thr Leu Ile Arg
                100                 105                 110 gaa tgg gga gat gct gtc ttt gat att ttc gac aaa gat gga agt ggt     384
Glu Trp Gly Asp Ala Val Phe Asp Ile Phe Asp Lys Asp Gly Ser Gly
                115                 120                 125 aca atc act ttg gac gaa tgg aaa gct tat gga aaa atc tct ggt atc     432
Thr Ile Thr Leu Asp Glu Trp Lys Ala Tyr Gly Lys Ile Ser Gly Ile
130                 135                 140
```

```
tct cca tca caa gaa gat tgt gaa gcg aca ttt cga cat tgc gat ttg        480
Ser Pro Ser Gln Glu Asp Cys Glu Ala Thr Phe Arg His Cys Asp Leu
145             150                 155                 160 gac aac agt ggt gac ctt gat gtt gac gag atg aca aga caa cat ctt        528
Asp Asn Ser Gly Asp Leu Asp Val Asp Glu Met Thr Arg Gln His Leu
        165                 170                 175 gga ttc tgg tac act ttg gac cca gaa gct gat ggt ctc tat ggc aac        576
Gly Phe Trp Tyr Thr Leu Asp Pro Glu Ala Asp Gly Leu Tyr Gly Asn
    180                 185                 190 gga gtt ccc taa                                                        588
Gly Val Pro
        195

<210> SEQ ID NO 10
<211> LENGTH: 195
<212> TYPE: PRT
<213> ORGANISM: Obelia longissima

<400> SEQUENCE: 10

Met Ser Ser Lys Tyr Ala Val Lys Leu Lys Thr Asp Phe Asp Asn Pro
1               5                   10                  15

Arg Trp Ile Lys Arg His Lys His Met Phe Asp Phe Leu Asp Ile Asn
            20                  25                  30

Gly Asn Gly Lys Ile Thr Leu Asp Glu Ile Val Ser Lys Ala Ser Asp
        35                  40                  45

Asp Ile Cys Ala Lys Leu Glu Ala Thr Pro Glu Gln Thr Lys Arg His
    50                  55                  60

Gln Val Cys Val Glu Ala Phe Phe Arg Gly Cys Gly Met Glu Tyr Gly
65                  70                  75                  80

Lys Glu Ile Ala Phe Pro Gln Phe Leu Asp Gly Trp Lys Gln Leu Ala
                85                  90                  95

Thr Ser Glu Leu Lys Lys Trp Ala Arg Asn Glu Pro Thr Leu Ile Arg
            100                 105                 110

Glu Trp Gly Asp Ala Val Phe Asp Ile Phe Asp Lys Asp Gly Ser Gly
        115                 120                 125

Thr Ile Thr Leu Asp Glu Trp Lys Ala Tyr Gly Lys Ile Ser Gly Ile
    130                 135                 140

Ser Pro Ser Gln Glu Asp Cys Glu Ala Thr Phe Arg His Cys Asp Leu
145             150                 155                 160

Asp Asn Ser Gly Asp Leu Asp Val Asp Glu Met Thr Arg Gln His Leu
                165                 170                 175

Gly Phe Trp Tyr Thr Leu Asp Pro Glu Ala Asp Gly Leu Tyr Gly Asn
            180                 185                 190

Gly Val Pro
        195

<210> SEQ ID NO 11
<211> LENGTH: 627
<212> TYPE: DNA
<213> ORGANISM: Beroe abyssicola
<220> FEATURE:
<221> NAME/KEY: CDS
<222> LOCATION: (1)..(627)

<400> SEQUENCE: 11 atg act gaa cgt ctg aac gag cag aac aac gag agt tac cgc tac ctg         48
Met Thr Glu Arg Leu Asn Glu Gln Asn Asn Glu Ser Tyr Arg Tyr Leu
1               5                   10                  15 aga agc gtg gga aac cag tgg cag ttc aac gta gag gac ctc cac ccc         96
```

-continued

```
                Arg Ser Val Gly Asn Gln Trp Gln Phe Asn Val Glu Asp Leu His Pro
                             20                  25                  30 aag atg ttg tcc cgt ctc tac aag aga ttc gat act ttc gat cta gac      144
Lys Met Leu Ser Arg Leu Tyr Lys Arg Phe Asp Thr Phe Asp Leu Asp
             35                  40                  45 agt gac ggt aag atg gag atg gac gag gtc ttg tac tgg ccc gac agg      192
Ser Asp Gly Lys Met Glu Met Asp Glu Val Leu Tyr Trp Pro Asp Arg
 50                  55                  60 atg agg cag ctg gta aac gct act gat gag cag gtt gag aag atg cgg      240
Met Arg Gln Leu Val Asn Ala Thr Asp Glu Gln Val Glu Lys Met Arg
 65                  70                  75                  80 gat gct gtg aga gtt ttc ttt ttg cac aag gga gtg gag cca gta aac      288
Asp Ala Val Arg Val Phe Phe Leu His Lys Gly Val Glu Pro Val Asn
                 85                  90                  95 ggt ctc ctc aga gag gac tgg gtg gaa gct aac aga gtc ttc gct gag      336
Gly Leu Leu Arg Glu Asp Trp Val Glu Ala Asn Arg Val Phe Ala Glu
            100                 105                 110 gct gag aga gaa aga gag cga cga gga gaa cct tct ctt atc gca ctt      384
Ala Glu Arg Glu Arg Glu Arg Arg Gly Glu Pro Ser Leu Ile Ala Leu
            115                 120                 125 ctc tcc aac tct tac tac gat gta ctg gat gat gac ggt gat ggt act      432
Leu Ser Asn Ser Tyr Tyr Asp Val Leu Asp Asp Asp Gly Asp Gly Thr
130                 135                 140 gtt gac gtc gat gaa tta aag acc atg atg aaa gca ttt gat gtg ccc      480
Val Asp Val Asp Glu Leu Lys Thr Met Met Lys Ala Phe Asp Val Pro
145                 150                 155                 160 cag gaa gct gcc tac acc ttc ttc gag aag gca gac act gac aag agt      528
Gln Glu Ala Ala Tyr Thr Phe Phe Glu Lys Ala Asp Thr Asp Lys Ser
                165                 170                 175 gga aag ttg gag aga aca gaa cta gtt cat ctc ttt aga aag ttt tgg      576
Gly Lys Leu Glu Arg Thr Glu Leu Val His Leu Phe Arg Lys Phe Trp
            180                 185                 190 atg gag cct tac gat cca cag tgg gac gga gtc tac gct tat aag tac      624
Met Glu Pro Tyr Asp Pro Gln Trp Asp Gly Val Tyr Ala Tyr Lys Tyr
            195                 200                 205 taa                                                                   627
```

<210> SEQ ID NO 12
<211> LENGTH: 208
<212> TYPE: PRT
<213> ORGANISM: Beroe abyssicola

<400> SEQUENCE: 12

```
Met Thr Glu Arg Leu Asn Glu Gln Asn Asn Glu Ser Tyr Arg Tyr Leu
 1               5                  10                  15

Arg Ser Val Gly Asn Gln Trp Gln Phe Asn Val Glu Asp Leu His Pro
             20                  25                  30

Lys Met Leu Ser Arg Leu Tyr Lys Arg Phe Asp Thr Phe Asp Leu Asp
         35                  40                  45

Ser Asp Gly Lys Met Glu Met Asp Glu Val Leu Tyr Trp Pro Asp Arg
 50                  55                  60

Met Arg Gln Leu Val Asn Ala Thr Asp Glu Gln Val Glu Lys Met Arg
 65                  70                  75                  80

Asp Ala Val Arg Val Phe Phe Leu His Lys Gly Val Glu Pro Val Asn
                 85                  90                  95

Gly Leu Leu Arg Glu Asp Trp Val Glu Ala Asn Arg Val Phe Ala Glu
            100                 105                 110

Ala Glu Arg Glu Arg Glu Arg Arg Gly Glu Pro Ser Leu Ile Ala Leu
```

```
                115                 120                 125
Leu Ser Asn Ser Tyr Tyr Asp Val Leu Asp Asp Gly Asp Gly Thr
    130                 135                 140
Val Asp Val Asp Glu Leu Lys Thr Met Met Lys Ala Phe Asp Val Pro
145                 150                 155                 160
Gln Glu Ala Ala Tyr Thr Phe Phe Glu Lys Ala Asp Thr Asp Lys Ser
                165                 170                 175
Gly Lys Leu Glu Arg Thr Glu Leu Val His Leu Phe Arg Lys Phe Trp
            180                 185                 190
Met Glu Pro Tyr Asp Pro Gln Trp Asp Gly Val Tyr Ala Tyr Lys Tyr
        195                 200                 205

<210> SEQ ID NO 13
<211> LENGTH: 936
<212> TYPE: DNA
<213> ORGANISM: Renilla reniformis
<220> FEATURE:
<221> NAME/KEY: CDS
<222> LOCATION: (1)..(936)

<400> SEQUENCE: 13 atg act tcg aaa gtt tat gat cca gaa caa agg aaa cgg atg ata act      48
Met Thr Ser Lys Val Tyr Asp Pro Glu Gln Arg Lys Arg Met Ile Thr
1               5                   10                  15 ggt ccg cag tgg tgg gcc aga tgt aaa caa atg aat gtt ctt gat tca     96
Gly Pro Gln Trp Trp Ala Arg Cys Lys Gln Met Asn Val Leu Asp Ser
            20                  25                  30 ttt att aat tat tat gat tca gaa aaa cat gca gaa aat gct gtt att    144
Phe Ile Asn Tyr Tyr Asp Ser Glu Lys His Ala Glu Asn Ala Val Ile
        35                  40                  45 ttt tta cat ggt aac gcg gcc tct tct tat tta tgg cga cat gtt gtg    192
Phe Leu His Gly Asn Ala Ala Ser Ser Tyr Leu Trp Arg His Val Val
    50                  55                  60 cca cat att gag cca gta gcg cgg tgt att ata cca gat ctt att ggt    240
Pro His Ile Glu Pro Val Ala Arg Cys Ile Ile Pro Asp Leu Ile Gly
65                  70                  75                  80 atg ggc aaa tca ggc aaa tct ggt aat ggt tct tat agg tta ctt gat    288
Met Gly Lys Ser Gly Lys Ser Gly Asn Gly Ser Tyr Arg Leu Leu Asp
                85                  90                  95 cat tac aaa tat ctt act gca tgg ttt gaa ctt ctt aat tta cca aag    336
His Tyr Lys Tyr Leu Thr Ala Trp Phe Glu Leu Leu Asn Leu Pro Lys
            100                 105                 110 aag atc att ttt gtc ggc cat gat tgg ggt gct tgt ttg gca ttt cat    384
Lys Ile Ile Phe Val Gly His Asp Trp Gly Ala Cys Leu Ala Phe His
        115                 120                 125 tat agc tat gag cat caa gat aag atc aaa gca ata gtt cac gct gaa    432
Tyr Ser Tyr Glu His Gln Asp Lys Ile Lys Ala Ile Val His Ala Glu
    130                 135                 140 agt gta gta gat gtg att gaa tca tgg gat gaa tgg cct gat att gaa    480
Ser Val Val Asp Val Ile Glu Ser Trp Asp Glu Trp Pro Asp Ile Glu
145                 150                 155                 160 gaa gat att gcg ttg atc aaa tct gaa gaa gga gaa aaa atg gtt ttg    528
Glu Asp Ile Ala Leu Ile Lys Ser Glu Glu Gly Glu Lys Met Val Leu
                165                 170                 175 gag aat aac ttc ttc gtg gaa acc atg ttg cca tca aaa atc atg aga    576
Glu Asn Asn Phe Phe Val Glu Thr Met Leu Pro Ser Lys Ile Met Arg
            180                 185                 190 aag tta gaa cca gaa gaa ttt gca gca tat ctt gaa cca ttc aaa gag    624
Lys Leu Glu Pro Glu Glu Phe Ala Ala Tyr Leu Glu Pro Phe Lys Glu
        195                 200                 205
```

```
aaa ggt gaa gtt cgt cgt cca aca tta tca tgg cct cgt gaa atc ccg      672
Lys Gly Glu Val Arg Arg Pro Thr Leu Ser Trp Pro Arg Glu Ile Pro
    210                 215                 220 tta gta aaa ggt ggt aaa cct gac gtt gta caa att gtt agg aat tat      720
Leu Val Lys Gly Gly Lys Pro Asp Val Val Gln Ile Val Arg Asn Tyr
225                 230                 235                 240 aat gct tat cta cgt gca agt gat gat tta cca aaa atg ttt att gaa      768
Asn Ala Tyr Leu Arg Ala Ser Asp Asp Leu Pro Lys Met Phe Ile Glu
                245                 250                 255 tcg gat cca gga ttc ttt tcc aat gct att gtt gaa ggc gcc aag aag      816
Ser Asp Pro Gly Phe Phe Ser Asn Ala Ile Val Glu Gly Ala Lys Lys
            260                 265                 270 ttt cct aat act gaa ttt gtc aaa gta aaa ggt ctt cat ttt tcg caa      864
Phe Pro Asn Thr Glu Phe Val Lys Val Lys Gly Leu His Phe Ser Gln
        275                 280                 285 gaa gat gca cct gat gaa atg gga aaa tat atc aaa tcg ttc gtt gag      912
Glu Asp Ala Pro Asp Glu Met Gly Lys Tyr Ile Lys Ser Phe Val Glu
    290                 295                 300 cga gtt ctc aaa aat gaa caa taa                                      936
Arg Val Leu Lys Asn Glu Gln
305                 310
```

<210> SEQ ID NO 14
<211> LENGTH: 311
<212> TYPE: PRT
<213> ORGANISM: Renilla reniformis

<400> SEQUENCE: 14

```
Met Thr Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Ala Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Cys Leu Ala Phe His
        115                 120                 125

Tyr Ser Tyr Glu His Gln Asp Lys Ile Lys Ala Ile Val His Ala Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Met Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220
```

```
Leu Val Lys Gly Gly Lys Pro Asp Val Val Gln Ile Val Arg Asn Tyr
225                 230                 235                 240

Asn Ala Tyr Leu Arg Ala Ser Asp Leu Pro Lys Met Phe Ile Glu
            245                 250                 255

Ser Asp Pro Gly Phe Phe Ser Asn Ala Ile Val Glu Gly Ala Lys Lys
        260                 265                 270

Phe Pro Asn Thr Glu Phe Val Lys Val Lys Gly Leu His Phe Ser Gln
        275                 280                 285

Glu Asp Ala Pro Asp Glu Met Gly Lys Tyr Ile Lys Ser Phe Val Glu
        290                 295                 300

Arg Val Leu Lys Asn Glu Gln
305                 310

<210> SEQ ID NO 15
<211> LENGTH: 591
<212> TYPE: DNA
<213> ORGANISM: Oplophorus gracilorostris
<220> FEATURE:
<221> NAME/KEY: CDS
<222> LOCATION: (1)..(591)

<400> SEQUENCE: 15
```

| | | | | | | | | | | | | | | | | |
|---|---|---|---|---|---|---|---|---|---|---|---|---|---|---|---|---|
| atg gcg tac tcc act ctg ttc ata att gca ttg acc gcc gtt gtc act | | | | | | | | | | | | | | | | 48 |
| Met Ala Tyr Ser Thr Leu Phe Ile Ile Ala Leu Thr Ala Val Val Thr | | | | | | | | | | | | | | | | |
| 1               5                   10                  15 | | | | | | | | | | | | | | | | |

```
caa gct tcc tca act caa aaa tct aac cta act ttt acg ttg gca gat   96
Gln Ala Ser Ser Thr Gln Lys Ser Asn Leu Thr Phe Thr Leu Ala Asp
            20                  25                  30 ttc gtt gga gac tgg caa cag aca gct gga tac aac caa gat caa gtg  144
Phe Val Gly Asp Trp Gln Gln Thr Ala Gly Tyr Asn Gln Asp Gln Val
        35                  40                  45 tta gaa caa gga gga ttg tct agt ctg ttc caa gcc ctg gga gtg tca  192
Leu Glu Gln Gly Gly Leu Ser Ser Leu Phe Gln Ala Leu Gly Val Ser
50                  55                  60 gtc acg ccc ata cag aaa gtt gta ctg tct ggg gag aat ggg tta aaa  240
Val Thr Pro Ile Gln Lys Val Val Leu Ser Gly Glu Asn Gly Leu Lys
65                  70                  75                  80 gct gat att cat gtc ata ata cct tac gag gga ctc agt ggt ttt caa  288
Ala Asp Ile His Val Ile Ile Pro Tyr Glu Gly Leu Ser Gly Phe Gln
                85                  90                  95 atg ggt cta att gaa atg atc ttc aaa gtt gtt tac ccc gtg gat gat  336
Met Gly Leu Ile Glu Met Ile Phe Lys Val Val Tyr Pro Val Asp Asp
            100                 105                 110 cat cat ttc aag att att ctc cat tat ggt aca ctc gtt att gac ggt  384
His His Phe Lys Ile Ile Leu His Tyr Gly Thr Leu Val Ile Asp Gly
        115                 120                 125 gta aca ccc aac atg att gac tac ttt gga aga cct tac cct gga att  432
Val Thr Pro Asn Met Ile Asp Tyr Phe Gly Arg Pro Tyr Pro Gly Ile
130                 135                 140 gct gta ttt gac ggc aag cag atc aca gtt act gga act ctg tgg aac  480
Ala Val Phe Asp Gly Lys Gln Ile Thr Val Thr Gly Thr Leu Trp Asn
145                 150                 155                 160 ggc aac aag atc tat gat gag agg cta atc aac cct gat ggt tca ctc  528
Gly Asn Lys Ile Tyr Asp Glu Arg Leu Ile Asn Pro Asp Gly Ser Leu
                165                 170                 175 ctc ttc aga gtt act atc aat gga gtc acg gga tgg agg ctt tgc gag  576
Leu Phe Arg Val Thr Ile Asn Gly Val Thr Gly Trp Arg Leu Cys Glu
            180                 185                 190
```

```
aac att ctt gcc taa                                              591
Asn Ile Leu Ala
        195

<210> SEQ ID NO 16
<211> LENGTH: 196
<212> TYPE: PRT
<213> ORGANISM: Oplophorus gracilorostris

<400> SEQUENCE: 16

Met Ala Tyr Ser Thr Leu Phe Ile Ile Ala Leu Thr Ala Val Val Thr
1               5                   10                  15

Gln Ala Ser Ser Thr Gln Lys Ser Asn Leu Thr Phe Thr Leu Ala Asp
            20                  25                  30

Phe Val Gly Asp Trp Gln Gln Thr Ala Gly Tyr Asn Gln Asp Gln Val
        35                  40                  45

Leu Glu Gln Gly Gly Leu Ser Ser Leu Phe Gln Ala Leu Gly Val Ser
    50                  55                  60

Val Thr Pro Ile Gln Lys Val Val Leu Ser Gly Glu Asn Gly Leu Lys
65                  70                  75                  80

Ala Asp Ile His Val Ile Ile Pro Tyr Glu Gly Leu Ser Gly Phe Gln
                85                  90                  95

Met Gly Leu Ile Glu Met Ile Phe Lys Val Val Tyr Pro Val Asp Asp
            100                 105                 110

His His Phe Lys Ile Ile Leu His Tyr Gly Thr Leu Val Ile Asp Gly
        115                 120                 125

Val Thr Pro Asn Met Ile Asp Tyr Phe Gly Arg Pro Tyr Pro Gly Ile
    130                 135                 140

Ala Val Phe Asp Gly Lys Gln Ile Thr Val Thr Gly Thr Leu Trp Asn
145                 150                 155                 160

Gly Asn Lys Ile Tyr Asp Glu Arg Leu Ile Asn Pro Asp Gly Ser Leu
                165                 170                 175

Leu Phe Arg Val Thr Ile Asn Gly Val Thr Gly Trp Arg Leu Cys Glu
            180                 185                 190

Asn Ile Leu Ala
        195

<210> SEQ ID NO 17
<211> LENGTH: 558
<212> TYPE: DNA
<213> ORGANISM: Gaussia princeps
<220> FEATURE:
<221> NAME/KEY: CDS
<222> LOCATION: (1)..(558)

<400> SEQUENCE: 17 atg gga gtc aaa gtt ctg ttt gcc ctg atc tgc atc gct gtg gcc gag    48
Met Gly Val Lys Val Leu Phe Ala Leu Ile Cys Ile Ala Val Ala Glu
1               5                   10                  15 gcc aag ccc acc gag aac aac gaa gac ttc aac atc gtg gcc gtg gcc    96
Ala Lys Pro Thr Glu Asn Asn Glu Asp Phe Asn Ile Val Ala Val Ala
            20                  25                  30
```

```
agc aac ttc gcg acc acg gat ctc gat gct gac cgc ggg aag ttg ccc    144
Ser Asn Phe Ala Thr Thr Asp Leu Asp Ala Asp Arg Gly Lys Leu Pro
        35                  40                  45 ggc aag aag ctg ccg ctg gag gtg ctc aaa gag atg gaa gcc aat gcc    192
Gly Lys Lys Leu Pro Leu Glu Val Leu Lys Glu Met Glu Ala Asn Ala
 50                  55                  60 cgg aaa gct ggc tgc acc agg ggc tgt ctg atc tgc ctg tcc cac atc    240
Arg Lys Ala Gly Cys Thr Arg Gly Cys Leu Ile Cys Leu Ser His Ile
 65                  70                  75                  80 aag tgc acg ccc aag atg aag aag ttc atc cca gga cgc tgc cac acc    288
Lys Cys Thr Pro Lys Met Lys Lys Phe Ile Pro Gly Arg Cys His Thr
                 85                  90                  95 tac gaa ggc gac aaa gag tcc gca cag ggc ggc ata ggc gag gcg atc    336
Tyr Glu Gly Asp Lys Glu Ser Ala Gln Gly Gly Ile Gly Glu Ala Ile
            100                 105                 110 gtc gac att cct gag att cct ggg ttc aag gac ttg gag ccc atg gag    384
Val Asp Ile Pro Glu Ile Pro Gly Phe Lys Asp Leu Glu Pro Met Glu
        115                 120                 125 cag ttc atc gca cag gtc gat ctg tgt gtg gac tgc aca act ggc tgc    432
Gln Phe Ile Ala Gln Val Asp Leu Cys Val Asp Cys Thr Thr Gly Cys
130                 135                 140 ctc aaa ggg ctt gcc aac gtg cag tgt tct gac ctg ctc aag aag tgg    480
Leu Lys Gly Leu Ala Asn Val Gln Cys Ser Asp Leu Leu Lys Lys Trp
145                 150                 155                 160 ctg ccg caa cgc tgt gcg acc ttt gcc agc aag atc cag ggc cag gtg    528
Leu Pro Gln Arg Cys Ala Thr Phe Ala Ser Lys Ile Gln Gly Gln Val
                165                 170                 175 gac aag atc aag ggg gcc ggt ggt gac taa                            558
Asp Lys Ile Lys Gly Ala Gly Gly Asp
            180                 185

<210> SEQ ID NO 18
<211> LENGTH: 185
<212> TYPE: PRT
<213> ORGANISM: Gaussia princeps

<400> SEQUENCE: 18

Met Gly Val Lys Val Leu Phe Ala Leu Ile Cys Ile Ala Val Ala Glu
 1               5                   10                  15

Ala Lys Pro Thr Glu Asn Asn Glu Asp Phe Asn Ile Val Ala Val Ala
            20                  25                  30

Ser Asn Phe Ala Thr Thr Asp Leu Asp Ala Asp Arg Gly Lys Leu Pro
        35                  40                  45

Gly Lys Lys Leu Pro Leu Glu Val Leu Lys Glu Met Glu Ala Asn Ala
 50                  55                  60

Arg Lys Ala Gly Cys Thr Arg Gly Cys Leu Ile Cys Leu Ser His Ile
 65                  70                  75                  80

Lys Cys Thr Pro Lys Met Lys Lys Phe Ile Pro Gly Arg Cys His Thr
                 85                  90                  95

Tyr Glu Gly Asp Lys Glu Ser Ala Gln Gly Gly Ile Gly Glu Ala Ile
            100                 105                 110

Val Asp Ile Pro Glu Ile Pro Gly Phe Lys Asp Leu Glu Pro Met Glu
        115                 120                 125

Gln Phe Ile Ala Gln Val Asp Leu Cys Val Asp Cys Thr Thr Gly Cys
130                 135                 140

Leu Lys Gly Leu Ala Asn Val Gln Cys Ser Asp Leu Leu Lys Lys Trp
145                 150                 155                 160
```

```
Leu Pro Gln Arg Cys Ala Thr Phe Ala Ser Lys Ile Gln Gly Gln Val
            165                 170                 175

Asp Lys Ile Lys Gly Ala Gly Gly Asp
            180             185
```

COELENTERAZINE ANALOGS AND MANUFACTURING METHOD THEREOF

CROSS-REFERENCE TO RELATED PATENT APPLICATION

This application is a divisional application of U.S. application Ser. No. 13/146,784, filed Oct. 3, 2011, which a National Stage of PCT/JP2010/051807, filed on Feb. 8, 2010, which claims benefit of Japanese Application No. 2009-027921, filed Feb. 9, 2009, the disclosures of which are incorporated herein in their entirety by reference.

TECHNICAL FIELD

The present invention relates to coelenterazine analogs, a method for manufacturing the same, and so on.

BACKGROUND ART

The phenomenon of bioluminescence was observed in some living species, and was based on the chemical reaction of a luciferin (a luminescence substrate) and a luciferase (an enzyme catalyzes the luminescence reaction) in vivo. A number of researches including the researches for identification of luciferin and luciferase and for elucidation of the luminesence mechanism in a molecular level have been performed inside and outside of Japan.

In recent years, bioluminescence is used as a tool for biological research. In addition, the applied researches in the medical field including high through-put screening (HTS) of drugs, intramolecular imaging, etc., have been intensively developed on the basis of the principle of bioluminescence.

Fireflies, sea pansies *Renilla*, sea fireflies *Cypridina*, deep-sea shrimps *Oplophorus*, luminescent microorganisms, etc. are known as representative bioluminescent organisms that produce bioluminescence. The jellyfish *Aequorea victoria* is also a bioluminescent animal, but the bioluminescence of the jellyfish is not produced by the luciferase reaction. The luminescence is produced by the $Ca^{2+}$-triggered reaction of the photoprotein of aequorin, the complex of substrate-enzyme-molecular oxygen. It is known that many organisms utilize the compound having an imidazopyrazinone skeleton as a luminescence substrate in the bioluminescence system.

Among them, coelenterazine (CTZ) is a compound commonly used as a luminescence substrate (luciferin) for aequorin which is a photoprotein from jellyfish, or for luciferases from some bioluminescent organisms such as sea pansies *Renilla*, etc. Therefore, many findings of CTZ have been accumulated.

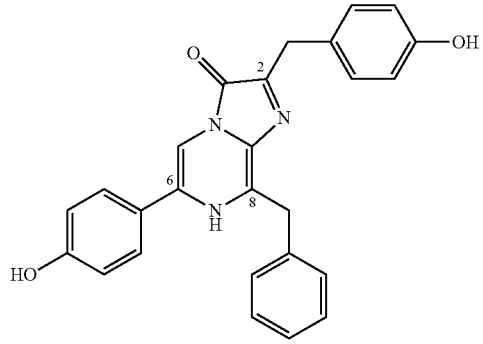

Coelenterazine (CTZ)

In fact, approximately 50 types of coelenterazine analog (CTZ analog) have been synthesized heretofore, and the substrate specificity for some of them has been examined in several bioluminescence systems (cf., e.g., Non-Patent Literatures 1 to 5).

CITATION LIST

Non-Patent Literature

[Non-Patent Literature 1] Shimomura O. et al., Biochem. J. 251, 405-410 (1988)
[Non-Patent Literature 2] Shimomura O. et al., Biochem. J. 261, 913-920 (1989)
[Non-Patent Literature 3] Inouye S. & Shimomura O., Biochem. Biophys. Res. Commun. 233, 349-353 (1997)
[Non-Patent Literature 4] Inouye S. & Sasaki S., Protein Express. Purif. 56, 261-268 (2007)
[Non-Patent Literature 5] Inouye S. & Sahara Y., Biochem. Biophys. Res. Commun. 265, 96-101 (2008)

SUMMARY OF THE INVENTION

Problems to be Solved by the Invention

Under the foregoing situations, coelenterazine analogs having different luminescence properties from those of known coelenterazine analogs have been sought.

Means of Solving the Problems

The present inventors have conducted extensive investigations to solve the foregoing problems. As a result, the inventors have found that coelenterazine analogs having methyl, trifluoromethyl, methoxy or ethyl in place of hydroxy on the benzene ring at the position 2 of coelenterazine possess luminescence properties, which are different from those of known coelenterazine analogs, and have come to attain the present invention.

That is, the present invention provides coelenterazine analogs, methods for producing coelenterazine analogs, and so on, which are shown below.

(1) A compound represented by general formula (1) below:

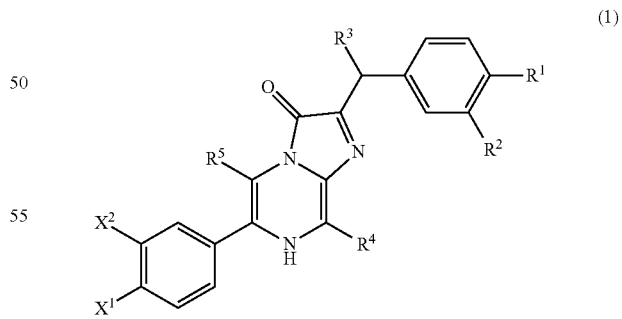

wherein:
$R^1$ is hydrogen, hydroxy, an alkyl having 1 to 4 carbon atoms which may optionally be substituted with an alicyclic group, trifluoromethyl or an alkoxyl;
$R^2$ is hydrogen, hydroxy, a halogen, an alkyl having 1 to 4 carbon atoms which may optionally be substituted with an alicyclic group, trifluoromethyl or an alkoxyl;

$R^3$ is hydrogen, an alkyl having 1 to 4 carbon atoms which may optionally be substituted with an alicyclic group, or an alkoxyl;

$R^4$ is a substituted or unsubstituted aryl, a substituted or unsubstituted arylalkyl, a substituted or unsubstituted arylalkenyl, an alkyl which may optionally be substituted with an alicyclic group, an alkenyl which may optionally be substituted with an alicyclic group, an alicyclic group, or a heterocyclic group;

$R^5$ is hydrogen or a substituted or unsubstituted alkyl;

$X^1$ is hydrogen, hydroxy, a halogen, an alkoxyl or amino; and, $X^2$ is hydrogen or hydroxy;

with the proviso that when $R^2$ and $R^3$ are hydrogen, $R^1$ is an alkyl having 1 to 4 carbon atoms which may optionally be substituted with an alicyclic group, trifluoromethyl, or an alkoxyl, when $R^1$ and $R^3$ are hydrogen, $R^2$ is hydroxy, an alkyl having 1 to 4 carbon atoms which may optionally be substituted with an alicyclic group, trifluoromethyl, or an alkoxyl, or, when $R^1$ and $R^2$ are hydrogen, $R^3$ is an alkyl having 1 to 4 carbon atoms which may optionally be substituted with an alicyclic group, or an alkoxyl.

(2) The compound according to (1) above, wherein $R^1$ is hydrogen, hydroxy, methyl, ethyl, propyl, adamantylmethyl, cyclopentylmethyl, cyclohexylmethyl, cyclohexylethyl, trifluoromethyl, methoxy, ethoxy, n-propoxy, iso-propoxy, sec-propoxy, n-butoxy, iso-butoxy, sec-butoxy or tert-butoxy, in the general formula (1).

(3) The compound according to (1) or (2) above, wherein $R^2$ is hydrogen, hydroxy, fluorine, methyl, ethyl, propyl, adamantylmethyl, cyclopentylmethyl, cyclohexylmethyl, cyclohexylethyl, trifluoromethyl, methoxy, ethoxy, n-propoxy, iso-propoxy, sec-propoxy, n-butoxy, iso-butoxy, sec-butoxy or tert-butoxy, in the general formula (1).

(4) The compound according to any one of (1) to (3) above, wherein $R^3$ is hydrogen, methyl, ethyl, propyl, adamantylmethyl, cyclopentylmethyl, cyclohexylmethyl, cyclohexylethyl, methoxy, ethoxy, n-propoxy, iso-propoxy, sec-propoxy, n-butoxy, iso-butoxy, sec-butoxy or tert-butoxy, in the general formula (1).

(5) The compound according to any one of (1) to (4) above, wherein $R^4$ is phenyl, p-hydroxyphenyl, benzyl, α-hydroxybenzyl, phenylethyl, phenylvinyl, cyclohexyl, cyclohexylmethyl, cyclohexylethyl, methyl, ethyl, propyl, 2-methylpropyl, 2-methylpropenyl, adamantylmethyl, cyclopentylmethyl or thiophen-2-yl, in the general formula (1).

(6) The compound according to any one of (1) to (5) above, wherein, in the general formula (1):
$R^1$ is hydrogen, methyl, ethyl, trifluoromethyl or methoxy;
$R^2$ is hydrogen, hydroxy, methyl or methoxy;
$R^3$ is hydrogen or methyl;
$R^4$ is benzyl;
$R^5$ is hydrogen;
$X^1$ is hydroxy; and,
$X^2$ is hydrogen;
with the proviso that when $R^2$ and $R^3$ are hydrogen, $R^1$ is methyl, ethyl, trifluoromethyl or methoxy,
when $R^1$ and $R^3$ are hydrogen, $R^2$ is hydroxy, methyl or methoxy, or,
when $R^1$ and $R^2$ are hydrogen, $R^3$ is methyl.

(7) The compound according to (6) above, which is represented by formula below.

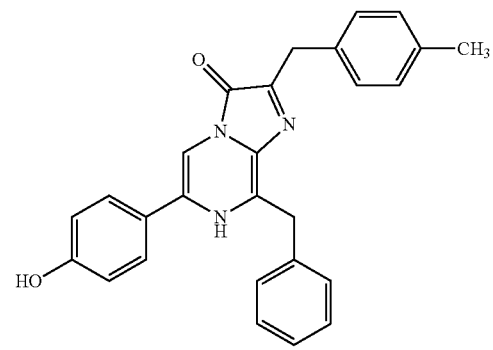 [SMILES: Cc1ccc(Cc2nc3c(Cc4ccccc4)[nH]c(-c4ccc(O)cc4)cn-3c2=O)cc1]

(8) The compound according to (6) above, which is represented by formula below.

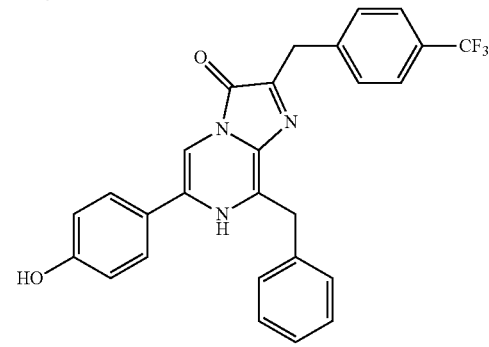 [SMILES: O=c1c(Cc2ccc(C(F)(F)F)cc2)nc2c(Cc3ccccc3)[nH]c(-c3ccc(O)cc3)cn1-2]

(9) The compound according to (6) above, which is represented by formula below.

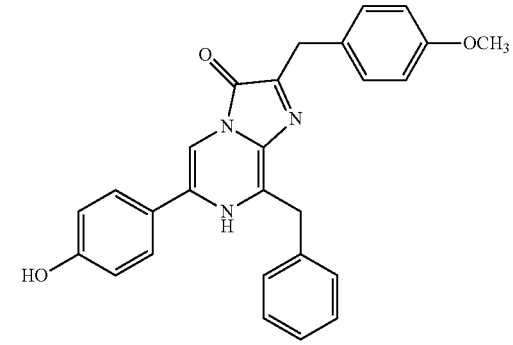 [SMILES: COc1ccc(Cc2nc3c(Cc4ccccc4)[nH]c(-c4ccc(O)cc4)cn-3c2=O)cc1]

(10) The compound according to (6) above, which is represented by formula below.

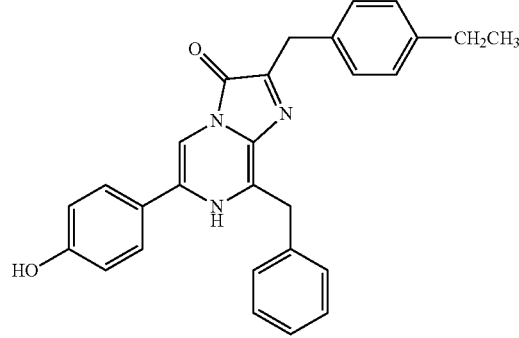 [SMILES: CCc1ccc(Cc2nc3c(Cc4ccccc4)[nH]c(-c4ccc(O)cc4)cn-3c2=O)cc1]

(11) The compound according to (6) above, which is represented by formula below.

(12) The compound according to (6) above, which is represented by formula below.

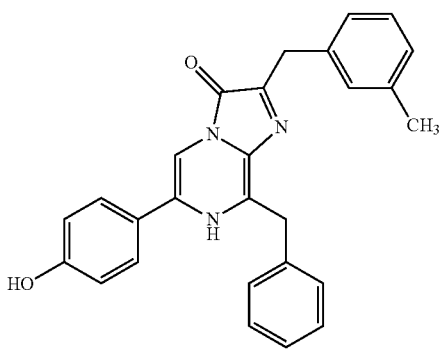 [SMILES: Cc1cccc(Cc2nc3c(Cc4ccccc4)[nH]c(-c4ccc(O)cc4)cn-3c2=O)c1]

(13) The compound according to (6) above, which is represented by formula below.

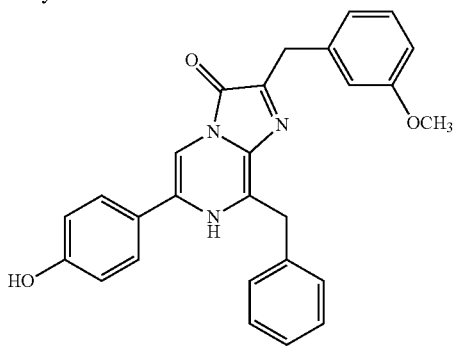

(14) The compound according to (6) above, which is represented by formula below.

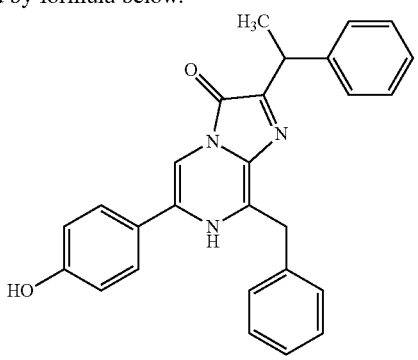

(15) A process for producing a compound represented by general formula (1) below:

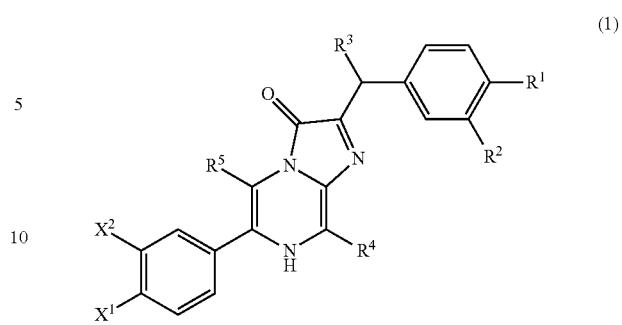

wherein $R^1$, $R^2$, $R^3$, $R^4$, $R^5$, $X^1$ and $X^2$ are the same as defined below, which comprises reacting a compound represented by general formula (2) below:

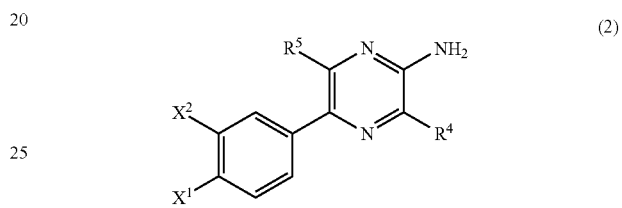

wherein:
$R^4$ is a substituted or unsubstituted aryl, a substituted or unsubstituted arylalkyl, a substituted or unsubstituted arylalkenyl, an alkyl which may optionally be substituted with an alicyclic group, an alkenyl which may optionally be substituted with an alicyclic group, an alicyclic group, or a heterocyclic group:
$R^5$ is hydrogen or a substituted or unsubstituted alkyl;
$X^1$ is hydrogen, hydroxy, a halogen, an alkoxyl or amino; and,
$X^2$ is hydrogen or hydroxy;
with a compound represented by general formula (3) below:

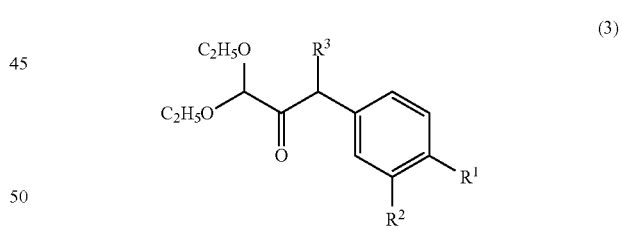

wherein:
$R^1$ is hydrogen, hydroxy, an alkyl having 1 to 4 carbon atoms which may optionally be substituted with an alicyclic group, trifluoromethyl or an alkoxyl;
$R^2$ is hydrogen, hydroxy, a halogen, an alkyl having 1 to 4 carbon atoms which may optionally be substituted with an alicyclic group, trifluoromethyl or an alkoxyl; and,
$R^3$ is hydrogen, an alkyl having 1 to 4 carbon atoms which may optionally be substituted with an alicyclic group, or an alkoxy;
with the proviso that when $R^2$ and $R^3$ are hydrogen, $R^1$ is an alkyl having 1 to 4 carbon atoms which may optionally be substituted with an alicyclic group, trifluoromethyl, or an alkoxyl, when R¹ and R³ are hydrogen, R² is hydroxy, an alkyl having 1 to 4 carbon atoms which may optionally be substituted with an alicyclic group, trifluoromethyl, or an alkoxyl, and, when R¹ and R² are hydrogen, R³ is an alkyl having 1 to 4 carbon atoms which may optionally be substituted with an alicyclic group, or an alkoxyl.

(16) The process according to (15) above, wherein R¹ is hydrogen, hydroxy, methyl, ethyl, propyl, adamantylmethyl, cyclopentylmethyl, cyclohexylmethyl, cyclohexylethyl, trifluoromethyl, methoxy, ethoxy, n-propoxy, iso-propoxy, sec-propoxy, n-butoxy, iso-butoxy, sec-butoxy or tert-butoxy, in the general formula (1).

(17) The process according to (15) or (16) above, wherein R² is hydrogen, hydroxy, fluorine, methyl, ethyl, propyl, adamantylmethyl, cyclopentylmethyl, cyclohexylmethyl, cyclohexylethyl, trifluoromethyl, methoxy, ethoxy, n-propoxy, iso-propoxy, sec-propoxy, n-butoxy, iso-butoxy, sec-butoxy or tert-butoxy, in the general formula (1).

(18) The process according to any one of (15) to (17) above, wherein R³ is hydrogen, methyl, ethyl, propyl, adamantylmethyl, cyclopentylmethyl, cyclohexylmethyl, cyclohexylethyl, methoxy, ethoxy, n-propoxy, iso-propoxy, sec-propoxy, n-butoxy, iso-butoxy, sec-butoxy or tert-butoxy, in the general formula (1).

(19) The process according to any one of (15) to (18) above, wherein R⁴ is phenyl, p-hydroxyphenyl, benzyl, t-hydroxybenzyl, phenylethyl, phenylvinyl, cyclohexyl, cyclohexylmethyl, cyclohexylethyl, methyl, ethyl, propyl, 2-methylpropyl, 2-methylpropenyl, adamantylmethyl, cyclopentylmethyl or thiophen-2-yl, in the general formula (1).

(20) The process according to any one of (15) to (19) above, wherein, in the general formula (1):
R¹ is hydrogen, methyl, ethyl, trifluoromethyl or methoxy,
R² is hydrogen, hydroxy, methyl or methoxy,
R³ is hydrogen or methyl,
R⁴ is benzyl,
R⁵ is hydrogen,
X¹ is hydroxy, and,
X² is hydrogen,
with the proviso that when R² and R³ are hydrogen, R¹ is methyl, ethyl, trifluoromethyl or methoxy,
when R¹ and R³ are hydrogen, R² is hydroxy, methyl or methoxy, and,
when R¹ and R² are hydrogen, R³ is methyl.

(21) A method for producing a calcium-binding photoprotein, which comprises contacting the compound according to any one of (1) to (14) above with an apoprotein of the calcium-binding photoprotein to obtain the calcium-binding photoprotein.

(22) A method for detecting or quantifying a calcium ion, which comprises using the calcium-binding photoprotein produced by the method according to (21) above.

(23) A method for analyzing a physiological function or enzyme activity, which comprises performing a bioluminescence resonance energy transfer (BRET) assay using as a donor protein the calcium-binding photoprotein produced by the method according to (21) above.

(24) A method for measuring a transcription activity or detecting an analyte, which comprises using the compound according to any one of (1) to (14) above, and a luciferase derived from *Renilla* sp., *Oplophorus* sp. or *Gaussia* sp.

(25) A method for analyzing a physiological function or enzyme activity, which comprises performing a bioluminescence resonance energy transfer (BRET) assay using the compound according to any one of (1) to (14) above and a luciferase derived from *Renilla* sp., *Oplophorus* sp. or *Gaussia* sp. as a donor protein.

(26) The method according to (24) or (25) above, wherein *Renilla* sp. is *Renilla reniformis*.

(27) The method according to (26) above, wherein the luciferase derived from *Renilla reniformis* comprises a polypeptide consisting of the amino acid sequence of SEQ ID NO: 14.

(28) The method according to (24) or (25) above, wherein *Oplophorus* sp. is *Oplophorus grachlorostris*.

(29) The method according to (28) above, wherein the luciferase derived from *Oplophorus grachlorostris* comprises a polypeptide consisting of the amino acid sequence of SEQ ID NO: 16.

(30) The method according to (24) or (25) above, wherein *Gaussia* sp. is *Gaussia princeps*.

(31) The method according to (30) above, wherein the luciferase derived from *Gaussia princeps* comprises a polypeptide consisting of the amino acid sequence of SEQ ID NO: 18.

(32) A kit for measuring a transcription activity or detecting an analyte, comprising the compound according to any one of (1) to (14) above and a luciferase derived from at least one organism selected from the group consisting of *Renilla* sp., *Oplophorus* sp. and *Gaussia* sp.

(33) A kit for analyzing a physiological function or enzyme activity, comprising the compound according to any one of (1) to (14) above, a luciferase derived from at least one organism selected from the group consisting of *Renilla* sp., *Oplophorus* sp. and *Gaussia* sp. and at least one selected from the group consisting of an organic compound and a fluorescent protein, utilizing the principle of intermolecular interaction by a bioluminescence resonance energy transfer (BRET) assay.

Effect of the Invention

The present invention provides novel coelenterazine analogs. Coelenterazine analogs in a preferred embodiment of the present invention exhibit the luminescence properties which are different from those of known coelenterazine analogs.

MODE FOR CARRYING OUT THE INVENTION

Figure 1:
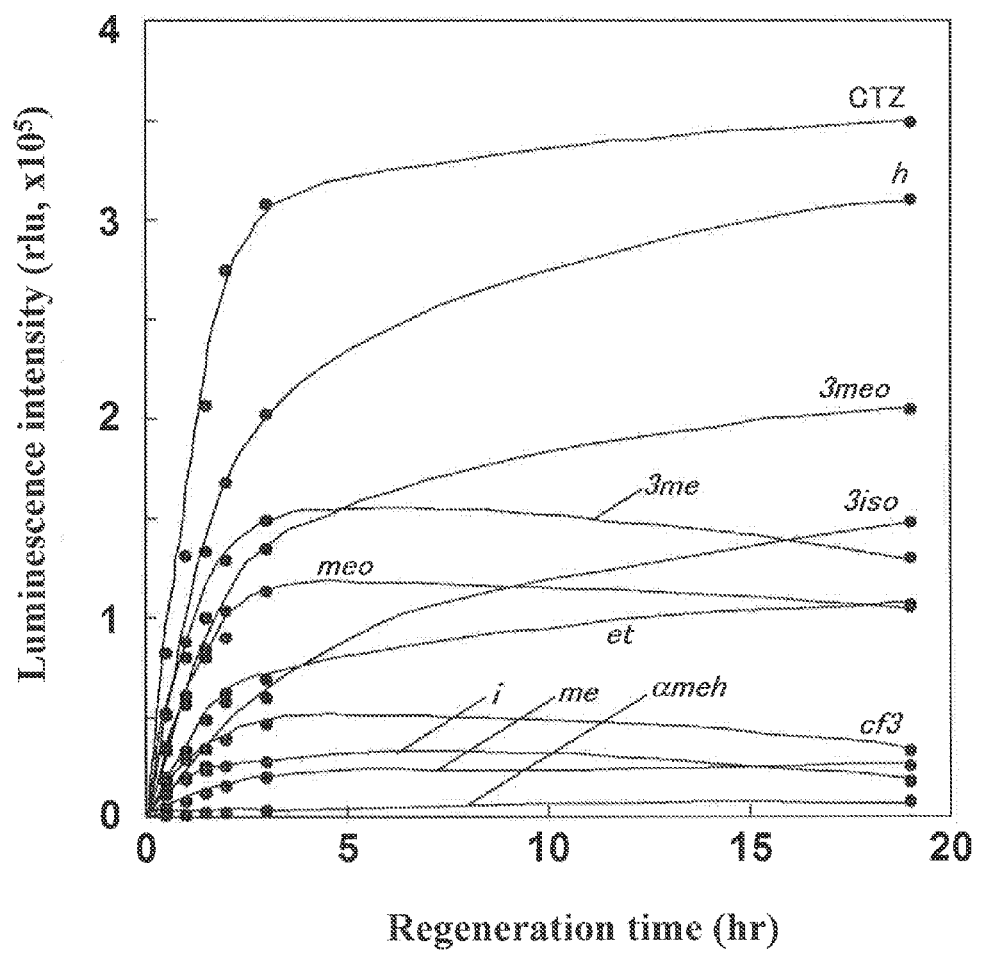
FIG. 1 shows the relationship between the regeneration time and luminescence intensity of semi-synthetic aequorins.

Hereinafter, the present invention is described in detail.
1. Coelenterazine Analog of the Invention The present invention provides the following compound (coelenterazine analog of the present invention) represented by general formula (1) below.

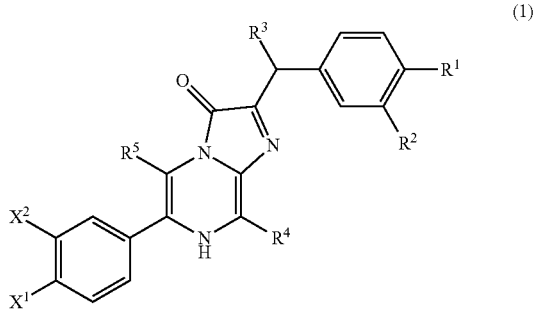

wherein:
R$^1$ is hydrogen, hydroxy, an alkyl having 1 to 4 carbon atoms which may optionally be substituted with an alicyclic group, trifluoromethyl or an alkoxyl;
R$^2$ is hydrogen, hydroxy, a halogen, an alkyl having 1 to 4 carbon atoms which may optionally be substituted with an alicyclic group, trifluoromethyl or an alkoxyl;
R$^3$ is hydrogen, an alkyl having 1 to 4 carbon atoms which may optionally be substituted with an alicyclic group, or an alkoxyl;
R$^4$ is a substituted or unsubstituted aryl, a substituted or unsubstituted arylalkyl, a substituted or unsubstituted arylalkenyl, an alkyl which may optionally be substituted with an alicyclic group, an alkenyl which may optionally be substituted with an alicyclic group, an alicyclic group, or a heterocyclic group;
R$^5$ is hydrogen or a substituted or unsubstituted alkyl;
X$^1$ is hydrogen, hydroxy, a halogen, an alkoxyl or amino; and,
X$^2$ is hydrogen or hydroxy;
with the proviso that when R$^2$ and R$^3$ are hydrogen, R$^1$ is an alkyl having 1 to 4 carbon atoms which may optionally be substituted with an alicyclic group, trifluoromethyl, or an alkoxyl;
when R$^1$ and R$^3$ are hydrogen, R$^2$ is hydroxy, an alkyl having 1 to 4 carbon atoms which may optionally be substituted with an alicyclic group, trifluoromethyl, or an alkoxyl; and,
when R$^1$ and R$^2$ are hydrogen, R$^3$ is an alkyl having 1 to 4 carbon atoms which may optionally be substituted with an alicyclic group, or an alkoxyl.

The "alkyl having 1 to 4 carbon atoms which may optionally be substituted with an alicyclic group" in R$^1$ is, for example, an unsubstituted straight or branched alkyl having 1 to 4 carbon atoms, or a straight or branched alkyl having 1 to 4 carbon atoms which is substituted with, e.g., 1 to 10 alicyclic groups. Examples of the alicyclic group include cyclohexyl, cyclopentyl, adamantyl, cyclobutyl, cyclopropyl, etc. Preferably, the alicyclic group is cyclohexyl, cyclopentyl, adamantyl, etc. The "alkyl which may optionally be substituted with an alicyclic group" is, for example, methyl, ethyl, propyl, 2-methylpropyl, adamantylmethyl, cyclopentylmethyl, cyclohexylmethyl, cyclohexylethyl, cyclobutylmethyl, cyclopropylmethyl, etc., preferably, methyl, ethyl, propyl, 2-methylpropyl, adamantylmethyl, cyclopentylmethyl, cyclohexylmethyl, cyclohexylethyl, and the like. In some embodiments of the present invention, the "alkyl which may optionally be substituted with an alicyclic group" is a straight alkyl which may optionally be substituted with an alicyclic group and examples are methyl, ethyl, propyl, adamantylmethyl, cyclopentylmethyl, cyclohexylmethyl, cyclohexylethyl, etc.

The "alkoxyl" in R$^1$ is, for example, a straight or branched alkoxy having 1 to 6 carbon atoms. Examples of the "alkoxy" are methoxy, ethoxy, n-propoxy, iso-propoxy, sec-propoxy, n-butoxy, iso-butoxy, sec-butoxy, tert-butoxy, n-pentyloxy, iso-pentyloxy, sec-pentyloxy, 1,1-dimethylpropyloxy, 1,2-dimethylpropoxy, 2,2-dimethylpropyloxy, n-hexoxy, 1-ethylpropoxy, 2-ethylpropoxy, 1-methylbutoxy, 2-methylbutoxy, iso-hexoxy, 1-methyl-2-ethylpropoxy, 1-ethyl-2-methylpropoxy, 1,1,2-trimethylpropoxy, 1,1,2-trimethylpropoxy, 1-propylpropoxy, 1,1-dimethylbutoxy, 1,2-dimethylbutoxy, 2,2-dimethylbutoxy, 2,3-dimethylbutyloxy, 1,3-dimethylbutyloxy, 2-ethylbutoxy, 1,3-dimethylbutoxy, 2-methylpentoxy, 3-methylpentoxy, hexyloxy, etc. In some embodiments of the invention, the "alkoxy" is methoxy, ethoxy, n-propoxy, iso-propoxy, sec-propoxy, n-butoxy, iso-butoxy, sec-butoxy or tert-butoxy, preferably, methoxy.

In a preferred embodiment of the invention, R$^1$ is hydrogen, hydroxy, methyl, ethyl, propyl, adamantylmethyl, cyclopentylmethyl, cyclohexylmethyl, cyclohexylethyl, trifluoromethyl, methoxy, ethoxy, n-propoxy, iso-propoxy, sec-propoxy, n-butoxy, iso-butoxy, sec-butoxy or tert-butoxy. In a more preferred embodiment of the invention, R$^1$ is hydrogen, methyl, ethyl, trifluoromethyl or methoxy.

The "halogen" in R$^2$ is, for example, fluorine, chlorine, bromine or iodine. In a preferred embodiment of the present invention, the "halogen" is fluorine.

The "alkyl having 1 to 4 carbon atoms which may optionally be substituted with an alicyclic group" in R$^2$ is, for example, an unsubstituted straight or branched alkyl having 1 to 4 carbon atoms, or a straight or branched alkyl having 1 to 4 carbon atoms which is substituted with, e.g., 1 to 10 alicyclic groups. Examples of the alicyclic group include cyclohexyl, cyclopentyl, adamantyl, cyclobutyl, cyclopropyl, etc. Preferably, the alicyclic group is cyclohexyl, cyclopentyl, adamantyl, etc. The "alkyl which may optionally be substituted with an alicyclic group" is, for example, methyl, ethyl, propyl, 2-methylpropyl, adamantylmethyl, cyclopentylmethyl, cyclohexylmethyl, cyclohexylethyl, cyclobutylmethyl, cyclopropylmethyl, etc., preferably, methyl, ethyl, propyl, 2-methylpropyl, adamantylmethyl, cyclopentylmethyl, cyclohexylmethyl, cyclohexylethyl, etc. In some embodiments of the present invention, the "alkyl which may optionally be substituted with an alicyclic group" is a straight alkyl which may optionally be substituted with an alicyclic group and examples are methyl, ethyl, propyl, adamantylmethyl, cyclopentylmethyl, cyclohexylmethyl, cyclohexylethyl, etc.

The "alkoxyl" in R$^2$ is, for example, a straight or branched alkoxy having 1 to 6 carbon atoms, and examples are methoxy, ethoxy, n-propoxy, iso-propoxy, sec-propoxy, n-butoxy, iso-butoxy, sec-butoxy, tert-butoxy, n-pentyloxy, iso-pentyloxy, sec-pentyloxy, 1,1-dimethylpropyloxy, 1,2-dimethylpropoxy, 2,2-dimethylpropyloxy, n-hexoxy, 1-ethylpropoxy, 2-ethylpropoxy, 1-methylbutoxy, 2-methylbutoxy, iso-hexoxy, 1-methyl-2-ethylpropoxy, 1-ethyl-2-methylpropoxy, 1,1,2-trimethylpropoxy, 1,1,2-trimethylpropoxy, 1-propylpropoxy, 1,1-dimethylbutoxy, 1,2-dimethylbutoxy, 2,2-dimethylbutoxy, 2,3-dimethylbutyloxy, 1,3-dimethylbutyloxy, 2-ethylbutoxy, 1,3-dimethylbutoxy, 2-methylpentoxy, 3-methylpentoxy, hexyloxy, etc. In some embodiments of the invention, the "alkoxy" is methoxy, ethoxy, n-propoxy, iso-propoxy, sec-propoxy, n-butoxy, iso-butoxy, sec-butoxy or tert-butoxy, preferably, methoxy.

In a preferred embodiment of the invention, $R^2$ is hydrogen, hydroxy, fluorine, methyl, ethyl, propyl, adamantylmethyl, cyclopentylmethyl, cyclohexylmethyl, cyclohexylethyl, trifluoromethyl, methoxy, ethoxy, n-propoxy, iso-propoxy, sec-propoxy, n-butoxy, iso-butoxy, sec-butoxy or tert-butoxy. In a more preferred embodiment of the invention, $R^2$ is hydrogen, hydroxy, methyl or methoxy.

The "alkyl having 1 to 4 carbon atoms which may optionally be substituted with an alicyclic group" in $R^3$ is, for example, an unsubstituted straight or branched alkyl having 1 to 4 carbon atoms, or a straight or branched alkyl having 1 to 4 carbon atoms which is substituted with, e.g., 1 to 10 alicyclic groups. Examples of the alicyclic group include cyclohexyl, cyclopentyl, adamantyl, cyclobutyl, cyclopropyl, etc. Preferably, the alicyclic group is cyclohexyl, cyclopentyl, adamantyl, etc. The "alkyl which may optionally be substituted with an alicyclic group" is, for example, methyl, ethyl, propyl, 2-methylpropyl, adamantylmethyl, cyclopentylmethyl, cyclohexylmethyl, cyclohexylethyl, cyclobutylmethyl, cyclopropylmethyl, etc., preferably, methyl, ethyl, propyl, 2-methylpropyl, adamantylmethyl, cyclopentylmethyl, cyclohexylmethyl, cyclohexylethyl, etc. In some embodiments of the invention, the "alkyl which may optionally be substituted with an alicyclic group" is a straight alkyl which may optionally be substituted with an alicyclic group, and examples include methyl, ethyl, propyl, adamantylmethyl, cyclopentylmethyl, cyclohexylmethyl, cyclohexylethyl, etc.

The "alkoxyl" in $R^3$ is, for example, a straight or branched alkoxy having 1 to 6 carbon atoms. Examples of the "alkoxy" are methoxy, ethoxy, n-propoxy, iso-propoxy, sec-propoxy, n-butoxy, iso-butoxy, sec-butoxy, tert-butoxy, n-pentyloxy, iso-pentyloxy, sec-pentyloxy, 1,1-dimethylpropyloxy, 1,2-dimethylpropyloxy, 2,2-dimethylpropyloxy, n-hexoxy, 1-ethylpropoxy, 2-ethylpropoxy, 1-methylbutoxy, 2-methylbutoxy, iso-hexoxy, 1-methyl-2-ethylpropoxy, 1-ethyl-2-methylpropoxy, 1,1,2-trimethylpropoxy, 1,1,2-trimethylpropoxy, 1-propylpropoxy, 1,1-dimethylbutoxy, 1,2-dimethylbutoxy, 2,2-dimethylbutoxy, 2,3-dimethylbutyloxy, 1,3-dimethylbutyloxy, 2-ethylbutoxy, 1,3-dimethylbutoxy, 2-methylpentoxy, 3-methylpentoxy, hexyloxy, etc. In some embodiments of the invention, the "alkoxy" is methoxy, ethoxy, n-propoxy, iso-propoxy, sec-propoxy, n-butoxy, iso-butoxy, sec-butoxy or tert-butoxy, preferably, methoxy.

In a preferred embodiment of the invention, $R^3$ is hydrogen, methyl, ethyl, propyl, adamantylmethyl, cyclopentylmethyl, cyclohexylmethyl, cyclohexylethyl, methoxy, ethoxy, n-propoxy, iso-propoxy, sec-propoxy, n-butoxy, iso-butoxy, sec-butoxy or tert-butoxy. In a more preferred embodiment of the invention, $R^3$ is hydrogen or methyl.

The "substituted or unsubstituted aryl" in $R^4$ is, for example, an aryl having 1 to 5 substituents or an unsubstituted aryl. The substituent is, for example, at least one selected from the group consisting of a halogen (fluorine, chlorine, bromine or iodine, etc.), hydroxy, an alkyl having 1 to 6 carbon atoms, an alkoxyl having 1 to 6 carbon atoms, amino and a dialkylamino having 1 to 6 carbon atoms. In some embodiments of the invention, the substituent is hydroxy. Specific examples of the "substituted or unsubstituted aryl" are phenyl, p-hydroxyphenyl, p-aminophenyl, p-dimethylaminophenyl, etc., preferably, phenyl, p-hydroxyphenyl, etc. In some embodiments of the invention, the "substituted or unsubstituted aryl" is an unsubstituted aryl, e.g., phenyl, etc.

The "substituted or unsubstituted arylalkyl" in $R^4$ is, for example, an arylalkyl having 7 to 10 carbon atoms, which is substituted with 1 to 5 substituents, or an unsubstituted arylalkyl having 7 to 10 carbon atoms. The substituent includes, for example, a halogen (fluorine, chlorine, bromine or iodine, etc.), hydroxy, an alkyl having 1 to 6 carbon atoms, an alkoxyl having 1 to 6 carbon atoms, amino, a dialkylamino having 1 to 6 carbon atoms, etc. Examples of the "substituted or unsubstituted arylalkyl" are benzyl, α-hydroxybenzyl, phenylethyl, p-hydroxybenzyl, p-dimethylaminobenzyl, etc., preferably, benzyl, α-hydroxybenzyl, phenylethyl, etc. In some embodiments of the invention, the "substituted or unsubstituted arylalkyl" is benzyl.

The "substituted or unsubstituted arylalkenyl" in $R^4$ is, for example, an arylalkenyl of 8 to 10 carbon atoms having 1 to 5 substituents, or an unsubstituted arylalkenyl having 8 to 10 carbon atoms. The substituent includes, for example, a halogen (fluorine, chlorine, bromine or iodine, etc.), hydroxy, an alkyl having 1 to 6 carbon atoms, an alkoxyl having 1 to 6 carbon atoms, amino, a dialkylamino having 1 to 6 carbon atoms, etc. Examples of the substituted or unsubstituted arylalkenyl" are phenylvinyl, p-hydroxyphenylvinyl, p-dimethylaminophenylvinyl, etc. In some embodiments of the present invention, the "substituted or unsubstituted arylalkenyl" is an unsubstituted arylalkenyl, e.g., phenylvinyl, etc.

The "alkyl which may optionally be substituted with an alicyclic group" in $R^4$ is, for example, an unsubstituted straight or branched alkyl having 1 to 4 carbon atoms, or a straight or branched alkyl having 1 to 4 carbon atoms which is substituted with, e.g., 1 to 10 alicyclic groups. Examples of the alicyclic group include cyclohexyl, cyclopentyl, adamantyl, cyclobutyl, cyclopropyl, etc. Preferably, the alicyclic group is cyclohexyl, cyclopentyl, adamantyl, etc. Examples of the "alkyl which may optionally be substituted with an alicyclic group" are methyl, ethyl, propyl, 2-methylpropyl, adamantylmethyl, cyclopentylmethyl, cyclohexylmethyl, cyclohexylethyl, cyclobutylmethyl, cyclopropylmethyl, etc., preferably, methyl, ethyl, propyl, 2-methylpropyl, adamantylmethyl, cyclopentylmethyl, cyclohexylmethyl, cyclohexylethyl, etc. In some embodiments of the present invention, the "alkyl which may optionally be substituted with an alicyclic group" is a straight alkyl which may optionally be substituted with an alicyclic group, and examples include methyl, ethyl, propyl, adamantylmethyl, cyclopentylmethyl, cyclohexylmethyl, cyclohexylethyl, etc.

The "alkenyl which may optionally be substituted with an alicyclic group" in $R^4$ is, for example, an unsubstituted straight or branched alkenyl having 2 to 6 carbon atoms, or a straight or branched alkenyl having 2 to 6 carbon atoms which is substituted with, e.g., 1 to 10 alicyclic groups. Examples of the alicyclic group include cyclohexyl, cyclopentyl, adamantyl, cyclobutyl, cyclopropyl, etc. Preferably, the alicyclic group is cyclohexyl, cyclopentyl, adamantyl, etc. Examples of the "alkenyl which may optionally be substituted with an alicyclic group" include vinyl, 1-propenyl, 2-propenyl, 1-butenyl, 2-butenyl, 3-butenyl, 2-methylpropenyl, etc., preferably, 2-methylpropenyl, etc.

The "alicyclic group" in $R^4$ includes, for example, cyclohexyl, cyclopentyl, adamantyl, cyclobutyl, cyclopropyl, etc. Preferably, the alicyclic group is cyclohexyl, etc.

The "heterocyclic group" in $R^4$ includes, for example, a group derived from a 5- to 7-membered ring containing, in addition to carbon atoms, 1 to 3 atoms selected from the group consisting of N, O and S as the atoms constituting the ring and bonded via carbon atoms, a group formed by fusing 2 or more of such rings and bonded via carbon, or a group formed by fusing such a ring to a benzene ring and bonding via carbon atoms. Examples of the "heterocyclic group" are thiophen-2-yl, 2-furanyl, 4-pyridyl, etc. In some embodiments of the present invention, the "heterocyclic group" is a heterocyclic group containing sulfur, e.g., thiophen-2-yl.

In a preferred embodiment of the present invention, $R^4$ is phenyl, p-hydroxyphenyl, benzyl, α-hydroxybenzyl, phenylethyl, phenylvinyl, cyclohexyl, cyclohexylmethyl, cyclohexylethyl, methyl, ethyl, propyl, 2-methylpropyl, 2-methylpropenyl, adamantylmethyl, cyclopentylmethyl or thiophen-2-yl. In a more preferred embodiment of the present invention, $R^4$ is benzyl.

The "substituted or unsubstituted alkyl" in $R^5$ is, for example, an alkyl of 1 to 6 carbon atoms having, e.g., 1 to 6 substituents, or an unsubstituted alkyl having 1 to 6 carbon atoms. The substituent is, for example, at least one selected from the group consisting of a halogen (fluorine, chlorine, bromine or iodine, etc.), hydroxy, carboxyl, an alkyl having 1 to 6 carbon atoms, an alkoxyl having 1 to 6 carbon atoms, amino and a dialkylamino having 1 to 6 carbon atoms. In some embodiments of the invention, the substituent is hydroxy. Specific examples of the "substituted or unsubstituted alkyl" are methyl, 2-hydroxyethyl, carboxymethyl, 3-hydroxypropyl, etc., preferably, methyl, 2-hydroxyethyl, etc.

In a preferred embodiment of the present invention, $R^5$ is hydrogen, methyl or 2-hydroxyethyl. In a more preferred embodiment of the present invention, $R^5$ is hydrogen.

The "halogen" in $X^1$ is, for example, fluorine, chlorine, bromine or iodine. In a preferred embodiment of the present invention, the "halogen" is fluorine.

The "alkoxyl" in $X^1$ is an alkoxyl having, e.g., 1 to 6 carbon atoms, and examples include methoxy, ethoxy, propoxy, isopropoxy, cyclopropoxy, tert-butyloxy, etc. In a preferred embodiment of the present invention, the "alkoxyl" is methoxy.

In a preferred embodiment of the present invention, $X^1$ is hydrogen, hydroxy, fluorine, methoxy or amino. In a more preferred embodiment of the present invention, $X^1$ is hydroxy.

In a preferred embodiment of the present invention, $X^2$ is hydrogen.

In some embodiments of the present invention, the following symbols represent as follows in the general formula (1):
$R^1$ is hydrogen, methyl, ethyl, trifluoromethyl or methoxy;
$R^2$ is hydrogen, hydroxy, methyl or methoxy;
$R^3$ is hydrogen or methyl;
$R^4$ is benzyl;
$R^5$ is hydrogen;
$X^1$ is hydroxy; and,
$X^2$ is hydrogen;

with the proviso that when $R^2$ and $R^3$ are hydrogen, $R^1$ is methyl, ethyl, trifluoromethyl or methoxy;
when $R^1$ and $R^3$ are hydrogen, $R^2$ is hydroxy, methyl or methoxy; and,
when $R^1$ and $R^2$ are hydrogen, $R^3$ is methyl.

In an embodiment of the present invention, the compound represented by general formula (1) is a compound represented by the formula below.

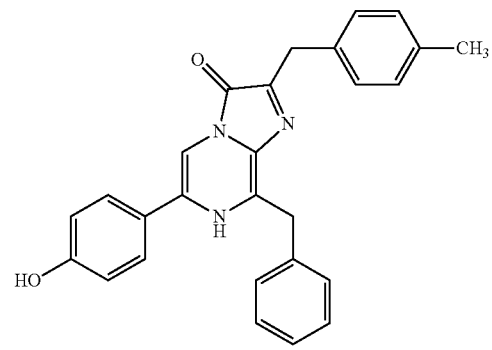

In another embodiment of the present invention, the compound represented by general formula (1) is a compound represented by the formula below.

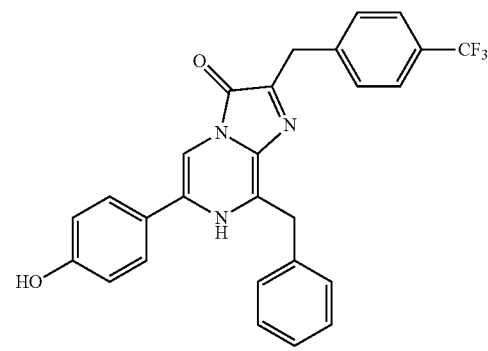

In a still another embodiment of the present invention, the compound represented by general formula (1) is a compound represented by the formula below.

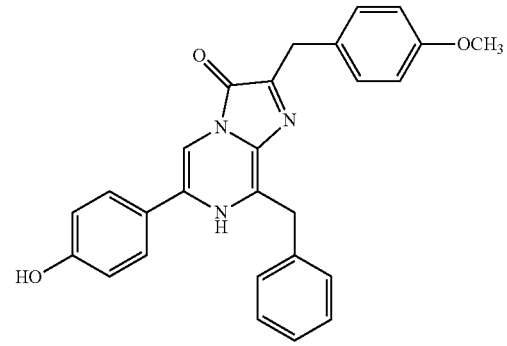

In a still another embodiment of the present invention, the compound represented by general formula (1) is a compound represented by the formula below.

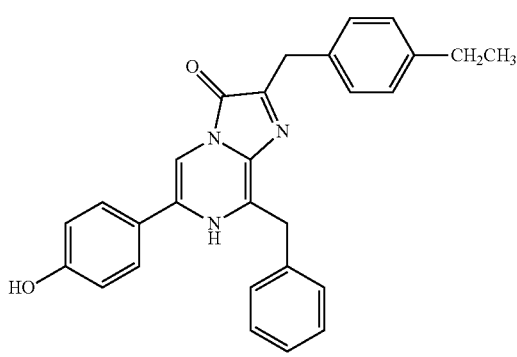

In a still another embodiment of the present invention, the compound represented by general formula (1) is a compound represented by the formula below.

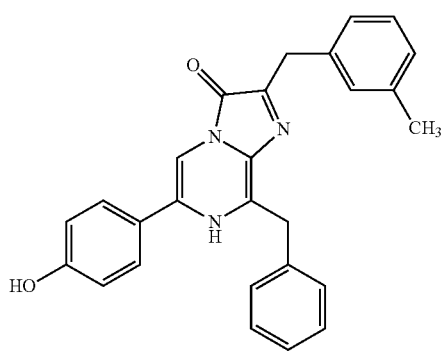

In a still another embodiment of the present invention, the compound represented by general formula (1) is a compound represented by the formula below.

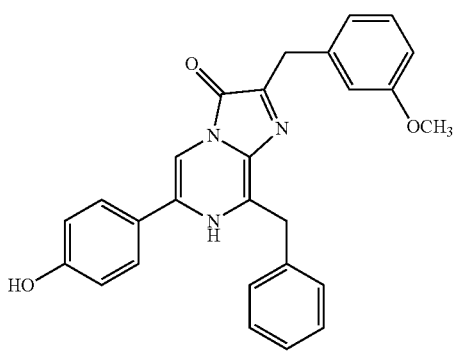

In a still another embodiment of the present invention, the compound represented by general formula (1) is a compound represented by the formula below.

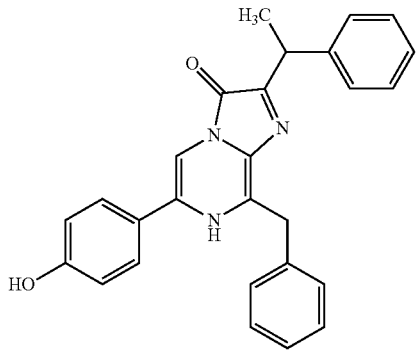

In a still another embodiment of the present invention, the compound represented by general formula (1) is a compound represented by the formula below.

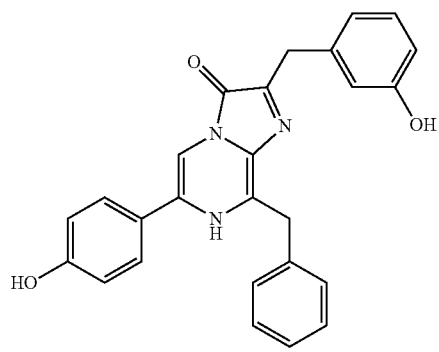

Coelenterazine analogs in an embodiment of the present invention exhibit the luminescence properties, which are different from those of known coelenterazine analogs (e.g., h-coelenterazine, n-coelenterazine, i-coelenterazine, etc.). Coelenterazine analogs in some embodiments of the present invention become relatively good luminescence substrates for at least one luciferase selected from the group consisting of *Oplophorus* luciferase, *Renilla* luciferase and *Gaussia* luciferase. Coelenterazine analogs in a preferred embodiment of the present invention become relatively good luminescence substrates for *Oplophorus* luciferase, *Renilla* luciferase and *Gaussia* luciferase.

2. Process for Producing Coelenterazine Analog of the Invention

The compound represented by general formula (1) (co-elenterazine analog of the invention) can be produced as follows.

That is, the compound represented by general formula (1) can be produced by reacting the compound represented by general formula (2) below:

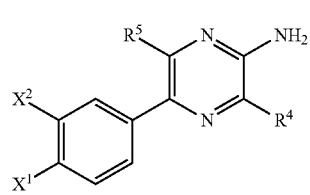

(2)

(wherein $R^4$, $R^5$, $X^1$ and $X^2$ are as defined above) with the compound represented by general formula (3) below:

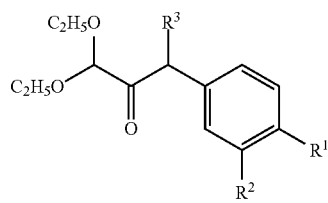

(wherein $R^1$, $R^2$ and $R^3$ are as defined above), whereby the compound represented by general formula (1) can be obtained.

The compound represented by general formula (2) can be prepared by known processes. For example, the compound represented by general formula (2) can be prepared, e.g., by the process described in Kishi, Y. et al., *Tetrahedron Let.*, 13, 2747-2748 (1972), or Adamczyk, M. et al., *Org. Prep. Proced Int.*, 33, 477-485 (2001), or their modifications. More specifically, the compound represented by general formula (2) can be prepared as follows. That is, first, cyclization of a substituted phenylglyoxal aldoxime and a glycinonitrile derivative is carried out using a Lewis acid catalyst to form the pyrazine oxide. Subsequently, the pyrazine oxide is subjected to catalytic hydrogenation using Raney Ni, etc. as a catalyst to prepare the compound. Alternatively, the compound represented by general formula (2) can be prepared by conducting the Suzuki-Miyaura coupling reaction between a 2-amino-5-bromopyrazine derivative and a substituted phenylboronic acid pinacol ester.

The compound represented by general formula (3) can be prepared by known processes. For example, the compound represented by general formula (3) can be prepared, e.g., by the processes described in Adamczyk, M. et al., *Synth. Commun.*, 32, 3199-3205 (2002), or Baganz, H. & May, H.-J. *Chem. Ber.*, 99, 3766-3770 (1966) and Baganz, H. & May, H.-J. Angew. *Chem., Int. Ed. Eng.*, 5, 420 (1966), or their modifications. More specifically, the compound represented by general formula (3) can be prepared as follows. That is, the compound represented by general formula (3) can be prepared either by reacting a substituted benzyl Grignard reagent with ethyl diethoxyacetate at a low temperature (−78° C.), or by reacting an α-diazo-α'-substituted phenyl ketone with tert-butyl hypochlorite in ethanol.

Herein, the solvent used for the process for producing the compound of the present invention represented by general formula (1) is not particularly limited and various solvents can be used. Examples of the solvent include dioxane, tetrahydrofuran, ether, methanol, ethanol, water, etc. These solvents can be used alone or as an admixture thereof.

In the process of producing the compound of the present invention represented by general formula (1), the reaction temperature and reaction time are not particularly limited and are, for example, 0° C. to 200° C. for 1 to 96 hours, room temperature to 150° C. for 3 to 72 hours, or 60° C. to 120° C. for 6 to 24 hours.

3. Method for Producing Calcium-Binding Photoprotein

The calcium-binding photoprotein of the invention can be produced or regenerated by contacting the compound represented by general formula (1) (coelenterazine analog of the invention) with the apoprotein of the calcium-binding photoprotein thereby to obtain the calcium-binding photoprotein.

As used herein, the term "contact" means that coelenterazine analog of the invention and the apoprotein of the calcium-binding photoprotein are allowed to be present in the same reaction system, and includes, for example, the apoprotein of the calcium-binding photoprotein being added to a container charged with coelenterazine analog of the invention, coelenterazine analog of the invention being added to a container charged with the apoprotein of the calcium-binding photoprotein, coelenterazine analog of the invention being mixed with the apoprotein of the calcium-binding photoprotein, and the like. In one embodiment of the present invention, the contact is carried out at a low temperature in the presence of a reducing agent (e.g., mercaptoethanol, dithiothreitol, etc.) and oxygen. More specifically, the photoprotein of the present invention can be produced or regenerated by the methods described in, e.g., Shimomura, O. et al. Biochem. J. 251, 405-410 (1988), Shimomura, O. et al. Biochem. J. 261, 913-920 (1989), and the like. The calcium-binding photoprotein of the present invention is present in such a state that a complex is formed between the peroxide of coelenterazine analog generated from coelenterazine analog of the invention and molecular oxygen and the apoprotein. Calcium ions are bound to the complex above to generate instantaneous luminescence and form coelenteramide analog, which is the oxide of coelenterazine analog, and carbon dioxide. The complex above is sometimes referred to as "the photoprotein of the present invention."

The apoprotein used to produce the photoprotein of the present invention includes, for example, apoaequorin, apoclytin-I, apoclytin-II, apobelin, apomitrocomin, apomineopsin, apobervoin, and the like. In some embodiments of the present invention, the apoprotein is apoaequorin, apobelin, apoclytin-I, apoclytin-II, apomitrocomin, etc., e.g., apoaequorin. These apoproteins may be obtained from natural sources or genetically engineered. Furthermore, the amino acid sequence may be mutated from the natural sequence by gene recombination technology, so long as the apoproteins are capable of producing the calcium-binding photoprotein.

The nucleotide sequences and amino acid sequences of the apoproteins of photoproteins obtained from the nature (natural apoproteins) are as follows. That is, the nucleotide sequence and amino acid sequence of natural apoaequorin are represented by SEQ ID NO: 1 and SEQ ID NO: 2. The nucleotide sequence and amino acid sequence of natural apoclytin-1 are represented by SEQ ID NO: 3 and SEQ ID NO: 4. The nucleotide sequence and amino acid sequence of natural apoclytin-II are represented by SEQ ID NO: 5 and SEQ ID NO: 6. The nucleotide sequence and amino acid sequence of natural apomitrocomin are represented by SEQ ID NO: 7 and SEQ ID NO: 8. The nucleotide sequence and amino acid sequence of natural apobelin are represented by SEQ ID NO: 9 and SEQ ID NO: 10. The nucleotide sequence and amino acid sequence of natural apobervoin are represented by SEQ ID NO: 11 and SEQ ID NO: 12.

The apoprotein mutated by recombinant technology is a protein selected from the group consisting of (a) to (c) below:

(a) a protein comprising the amino acid sequence of natural apoprotein in which 1 or more amino acids are deleted, substituted, inserted and/or added, and having the apoprotein activity or function of the calcium-binding photoprotein;

(b) a protein comprising an amino acid sequence which is 90% or more homologous to the amino acid sequence of natural apoprotein, and having the apoprotein activity or function of the calcium-binding photoprotein; and, (c) a protein comprising an amino acid sequence encoded by a polynucleotide that hybridizes under stringent conditions to a polynucleotide consisting of a nucleotide sequence complementary to the nucleotide sequence of natural apoprotein, and having the apoprotein activity or function of the calcium-binding photoprotein.

Examples of the "natural apoprotein" described above are apoaequorin, apoclytin-I, apoclytin-II, apobelin, apomitrocomin, apomineopsin, apobervoin, etc. In an embodiment of the present invention, the apoprotein is apoaequorin, apoclytin-I, apoclytin-II, apobelin, apomitrocomin, etc., preferably apoaequorin. The amino acid sequences and nucleotide sequences of these natural apoproteins are as described above.

The "apoprotein activity or function of the calcium-binding photoprotein" means the activity or function that, e.g., the apoprotein binds to the peroxide of coelenterazine or the peroxide of a coelenterazine analog to produce the calcium-binding photoprotein. Specifically, "the protein binds to the peroxide of coelenterazine or the peroxide of a coelenterazine analog to produce the calcium-binding photoprotein" not only means that (1) the protein binds to the peroxide of coelenterazine or the peroxide of a coelenterazine analog to produce the photoprotein, but also means that (2) the protein is brought into contact with coelenterazine or its derivative in the presence of oxygen to produce a photoprotein (complex) comprising the protein and the peroxide of coelenterazine or the peroxide of a coelenterazine analog. As used herein, the term "contact" means that the protein and coelenterazine or its analog are allowed to be present in the same reaction system, and includes, for example, the protein being added to a container charged with coelenterazine or its analog, coelenterazine or its analog being added to a container charged with the protein, the protein being mixed with coelenterazine or its analog, and the like. The "coelenterazine analog" refers to a compound which is capable of constituting a calcium-binding photoprotein such as aequorin, etc., together with the apoprotein in the same manner as in coelenterazine. Examples of coelenterazine or its analog include, in addition to coelenterazine analogs of the present invention, coelenterazine, h-coelenterazine, f-coelenterazine, cl-coelenterazine, n-coelenterazine, cp-coelenterazine, ch-coelenterazine, hch-coelenterazine, fch-coelenterazine, e-coelenterazin, ef-coelenterazine, ech-coelenterazine, hcp-coelenterazine, and the like. Coelenterazine analogs of the present invention can be produced, e.g., by the processes described above or their modifications. The other coelenterazines or their analogs can be produced by the processes described in, e.g., Shimomura et al. (1988) Biochem. J. 251, 405-410, Shimomura et al. (1989) Biochem. J., 261, 913-920, Shimomura et al. (1990) Biochem. J., 270, 309-312, or their modifications. Alternatively, various types of coelenterazine analogs are commercially available from Chisso Corporation, Wako Pure Chemical Industry Co., Ltd. and Promega Inc., and these commercial products may also be used.

The range of "1 or more" in "the amino acid sequence in which 1 or more amino acids are deleted, substituted, inserted and/or added" described above is, for example, 1 to 20, 1 to 15, 1 to 10, 1 to 9, 1 to 8, 1 to 7, 1 to 6 (1 to several), 1 to 5, 1 to 4, 1 to 3, 1 to 2, and 1. In general, the less the number of amino acids deleted, substituted, inserted or added, the more preferable. In the deletion, substitution, insertion and addition of the amino acid residues described above, two or more may occur concurrently. Such regions can be acquired using site-directed mutagenesis described in "Sambrook J. et al., Molecular Cloning: A Laboratory Manual, Third Edition, Cold Spring Harbor Laboratory Press (2001)," "Ausbel F. M. et al., Current Protocols in Molecular Biology, Supplement 1-38, John Wiley and Sons (1987-1997)," "Nuc. Acids. Res., 10, 6487 (1982)," "Proc. Natl. Acad. Sci. USA, 79, 6409 (1982)," "Gene, 34, 315 (1985)," "Nuc. Acids. Res., 13, 4431 (1985)," "Proc. Natl. Acad. Sci. USA, 82, 488 (1985)," etc.

The range of "90% or more" in the "amino acid sequence which is 90% or more homologous" described above is, for example, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more. It is generally preferred for the numerical value indicating the degree of homology to be higher. The homology between amino acid sequences or nucleotide sequences can be determined using a sequencing program such as BLAST (see, e.g., Altzchul, S. F. et al., J. Mol. Biol., 215, 403 (1990), etc.) or the like. When BLAST is used, the default parameters for the respective programs are employed.

The "polynucleotide that hybridizes under stringent conditions" described above refers to a polynucleotide (e.g., DNA) which is obtained by, for example, colony hybridization, plaque hybridization or Southern hybridization using as the probe a polynucleotide consisting of a nucleotide sequence complementary to the nucleotide sequence of natural apoprotein or all or part of the polynucleotide encoding the amino acid sequence of natural apoprotein. Specific examples include a polynucleotide which can be identified by performing hybridization at 65° C. in the presence of 0.7 to 1.0 mol/L NaCl using a filter on which the polynucleotide from the colony or plaque is immobilized, then washing the filter at 65° C. with 0.1- to 2-fold SSC (saline-sodium citrate) solution (a 1-fold SSC solution is composed of 150 mmol/L sodium chloride and 15 mmol/L sodium citrate).

Hybridization may be performed in accordance with modifications of the methods described in manuals, e.g., Sambrook, J. et al.: Molecular Cloning: A Laboratory Manual, Third Edition, Cold Spring Harbor Laboratory Press (2001), Ausbel F. M. et al., Current Protocols in Molecular Biology, Supplement 1-38, John Wiley and Sons (1987-1997), Glover D. M. and Hames B. D., DNA Cloning 1: Core Techniques, A practical Approach, Second Edition, Oxford University Press (1995), etc.

As used herein, "stringent conditions" may refer to less stringent conditions, moderately stringent conditions and highly stringent conditions. The "less stringent conditions" are, for example, the conditions under 5×SSC, 5×Denhardt's solution, 0.5% (w/v) SDS and 50% (v/v) formamide at 32° C. The "moderately stringent conditions" are, for example, the conditions under 5×SSC, 5×Denhardt's solution, 0.5% (w/v) SDS and 50% (v/v) formamide at 42° C. The "highly stringent conditions" are, for example, the conditions under 5×SSC, 5×Denhardt's solution, 0.5% (w/v) SDS and 50% (v/v) formamide at 50° C. The more stringent the conditions are, the higher the complementarity required for double strand formation. Specifically, for example, under these conditions, a polynucleotide (e.g., DNA) of higher homology is expected to be obtained efficiently at higher temperatures, although multiple factors are involved in hybridization stringency, including temperature, probe concentration, probe length, ionic strength, time and salt concentration; those skilled in the art may appropriately choose these factors to realize a similar stringency.

Where a kit commercially available is used for the hybridization, for example, Alkphos Direct Labeling Reagents (manufactured by Amersham Pharmacia) may be used. In this case, incubation with a labeled probe is performed overnight in accordance with the protocol attached to the kit, the membrane is then washed with a primary wash buffer containing 0.1% (w/v) SDS at 55° C., and finally the hybridized DNA can be detected.

Other hybridizable polynucleotides include, as calculated by a sequencing program such as BLAST or the like using the default parameters, DNAs having a homology of approximately 60% or more, 65% or more, 70% or more, 75% or more, 80% or more, 85% or more, 88% or more, 90% or more, 92% or more, 95% or more, 97% or more, 98% or more, 99% or more, 99.3% or more, 99.5% or more, 99.7% or more, 99.8% or more, or 99.9% or more, to the polynucleotide encoding the amino acid sequence of the apoprotein. The homology of amino acid sequences or nucleotide sequences can be determined using the method described above.

The recombinant apoprotein which can be used in the present invention includes, for example, recombinant aequorin described in Shimomura, O. and Inouye, S. Protein Express. Purif. (1999) 16: 91-95, recombinant clytin-I described in Inouye, S. and Sahara, Y. Protein Express. Purif. (2007) 53: 384-389, recombinant clytin-II described in Inouye, S. J. Biochem. (2008) 143: 711-717, and the like.

The calcium-binding photoprotein thus obtained may be further purified. Purification of the calcium-binding photoprotein may be performed in a conventional manner of separation/purification. The separation/purification includes, for example, precipitation with ammonium sulfate, gel filtration chromatography, ion exchange chromatography, affinity chromatography, reversed phase high performance liquid chromatography, dialysis, ultrafiltration, etc., alone or in an appropriate combination thereof.

The photoprotein in an embodiment of the present invention exhibits the luminescence properties which are different from those of known photoproteins. The photoprotein in some embodiments of the present invention show less $Ca^{2+}$ sensitivity when compared to the photoprotein containing natural coelenterazine, and are well suited for applications to a high-precision assay system in which $Ca^{2+}$ level change in the system is used as an indicator, in the same manner as in the photoprotein containing i-CTZ or n-CTZ.

4. Application of Coelenterazine Analog of the Invention or the Photoprotein of the Invention (1) Use as Luminescence Substrate Coelenterazine analog in some embodiments of the present invention emits light by the action of a luminescent catalyst and can thus be used as a luminescence substrate. Accordingly, the present invention provides a light-emitting method, which comprises contacting coelenterazine analog of the present invention with a luminescent catalyst. As used herein, the term "contact" means that coelenterazine analog of the invention and the luminescent catalyst are allowed to be present in the same reaction system, and includes, for example, the luminescent catalyst being added to a container charged with coelenterazine analog, coelenterazine analog being added to a container charged with the luminescent catalyst, coelenterazine analog being mixed with the luminescent catalyst, and the like.

The luminescent catalyst used for the light-emitting method of the present invention includes, for example, a luciferase derived from *Oplophorus* sp. (e.g., *Oplophorus grachlorostris*) (*Oplophorus* luciferase), a luciferase derived from *Gaussia* sp. (e.g., *Gaussia princeps*) (*Gaussia* luciferase), a luciferase derived from *Renilla* sp. (e.g., *Renilla reniformis* or *Renilla muelleri*) (*Renilla* luciferase), a luciferase derived from *Pleuromamma* sp. (*Pleuromamma* luciferase), or a luciferase derived from *Metridia longa* (*Metridia* luciferase). Coelenterazine analog in some embodiments of the present invention acts as a luminescence substrate for *Oplophorus* luciferase, *Gaussia* luciferase or *Renilla* luciferase. Coelenterazine analog in an embodiment of the present invention acts as a luminescence substrate for *Oplophorus* luciferase. Coelenterazine analog in another embodiment of the present invention acts as a luminescence substrate for *Oplophorus* luciferase, *Gaussia* luciferase and *Renilla* luciferase. These luminescent catalysts can be produced by the method described in, e.g., Shimomura et al. (1988) Biochem. J. 251, 405-410, Shimomura et al. (1989) Biochem. J. 261, 913-920, or Shimomura et al. (1990) Biochem. J. 270, 309-312, or modifications thereof. Alternatively, various products are commercially available from Chisso Corporation, Wako Pure Chemical Industry Co., Ltd. and Promega Inc., and these commercial products may also be used for the light-emitting method of the present invention.

Now, of *Renilla* luciferase, the nucleotide sequence and amino acid sequence of the luciferase derived from *Renilla reniformis* are represented by SEQ ID NO: 13 and SEQ ID NO: 14. Of *Oplophorus* luciferase, the nucleotide sequence and amino acid sequence of the luciferase derived from *Oplophorus grachlorostris* are represented by represented by SEQ ID NO: 15 and SEQ ID NO: 16. Furthermore, of *Gaussia* luciferase, the nucleotide sequence and amino acid sequence of the luciferase derived from *Gaussia princeps* are represented by SEQ ID NO: 17 and SEQ ID NO: 18.

In an embodiment of the present invention, *Renilla* luciferase is the luciferase derived from *Renilla reniformis* and comprises a polypeptide consisting of the amino acid sequence of, e.g., SEQ ID NO: 14. In another embodiment of the present invention, *Oplophorus* luciferase is the luciferase derived from *Oplophorus grachlorostris* and comprises a polypeptide consisting of the amino acid sequence of, e.g., SEQ ID NO: 16. In still another embodiment of the present invention, *Gaussia* luciferase is the luciferase derived from *Gaussia princeps* and comprises a polypeptide consisting of the amino acid sequence of, e.g., SEQ ID NO: 18.

When these luminescent catalysts are brought into contact with coelenterazine analog in some embodiments of the present invention, light is produced. The emission time is generally 0.01 to 1 hour. However, the emission time can be more prolonged or the emission time can be further shortened, depending upon conditions chosen.

(2) Detection or Quantification of Calcium Ions

The photoprotein of the present invention obtained as above is a photoprotein (holoprotein) that non-covalent bond is formed between the apoprotein and the peroxide of coelenterazine analog produced from coelenterazine analog and molecular oxygen and emits light by the action of calcium ions. Thus, the photoprotein of the invention can be used for the detection or quantification of calcium ions.

The detection or quantification of calcium ions may be performed by adding a sample solution directly to a solution of the photoprotein and measuring the luminescence generated. Alternatively, calcium ions may also be detected or quantified by adding a solution of the photoprotein to a sample solution and measuring the luminescence generated. The photoprotein described above may also be previously produced, before addition to the assay system for the detection or quantification of calcium ions, by contacting an aqueous solution of the apoprotein with coelenterazine analog of the present invention, which is provided for use. Alternatively, the photoprotein composed of the apoprotein and the peroxide of coelenterazine analog may be formed by contacting the apoprotein with coelenterazine analog in the assay system. The photoprotein formed is a complex (photoprotein) of the apoprotein and the peroxide of coelenterazine analog of the invention. The complex (i.e., the photoprotein of the present invention) described above emits light dependently on the calcium ion level.

The detection or quantification of calcium ions can be performed by measuring on a luminometer the luminescence of the photoprotein of the invention induced by calcium ions. Luminometers which can be used include commercially available instruments such as Centro LB 960 (manufactured by Berthold), etc. The calcium ion level can be quantified by preparing a luminescence standard curve for known calcium ion levels using the photoprotein.

Coelenterazine analog of the present invention may also be used to detect changes in intracellular calcium ion levels under physiological conditions, by preparing the photoprotein composed of the apoprotein and the peroxide of coelenterazine analog and directly introducing the photoprotein into the cell by means of microinjection, etc.

In addition to the introduction into a cell by means of microinjection, etc., coelenterazine analog of the present invention may also be used to form the photoprotein by intracellularly expressing an apoprotein gene (a polynucleotide encoding the apoprotein) to form the apoprotein within a cell and then adding coelenterazine analog of the present invention to the apoprotein thus formed from outside the cell.

Using the photoprotein of the invention thus introduced into or formed within the cell, changes in intracellular calcium ion levels in response to external stimuli (e.g., stimuli with a drug which is associated with a receptor) can also be measured.

(3) Use as Reporter Protein, etc. by Luminescence

The photoprotein of the present invention may also be used as a reporter protein to determine the transcription activity of a promoter, etc. A polynucleotide encoding the apoprotein is fused to a target promoter or other expression control sequence (e.g., an enhancer, etc.) to construct a vector. The vector is transformed to a host cell. Coelenterazine or its analog is brought into contact with the transformant. By detecting the luminescence from the photoprotein of the present invention, the activity of the target promoter or other expression control sequence can be determined. As used herein, the term "contact" means that a host cell and coelenterazine or its analog are allowed to be present in the same culture system or reaction system, and includes, for example, coelenterazine or its analog being added to a culture container charged with a host cell, a host cell being mixed with coelenterazine or its analog, a host cell being cultured in the presence of coelenterazine or its analog, and the like. Coelenterazine or its analog includes those described above, in addition to coelenterazine analog of the present invention.

Coelenterazine analog of the present invention may be used to determine the transcription activity of a promoter, etc. For example, a polynucleotide encoding a luminescent catalyst is fused to a target promoter or other expression control sequence (e.g., an enhancer, etc.) to construct a vector. The vector is transformed to a host cell. Coelenterazine analog of the present invention is brought into contact with the transformant. By detecting the luminescence from coelenterazine analog of the present invention, the activity of the target promoter or other expression control sequence can be determined. As used herein, the term "contact" means that a host cell and coelenterazine analog of the present invention are allowed to be present in the same culture system or reaction system, and includes, for example, coelenterazine analog being added to a culture container charged with a host cell, a host cell being mixed with coelenterazine analog, a host cell being cultured in the presence of coelenterazine analog, and the like. The luminescent catalyst includes those described above and is at least one selected from the group consisting of *Renilla* luciferase, *Oplophorus* luciferase and *Gaussia* luciferase.

The present invention further provides a kit used for measuring the transcription activity of a promoter, etc. The kit in some embodiments of the present invention comprises coelenterazine analog of the present invention and the luminescent catalyst. The kit in another embodiment of the present invention comprises the photoprotein of the present invention and coelenterazine or its analog. Reagents including coelenterazine or its analog, the luminescent catalyst, etc. may be dissolved in a suitable solvent and prepared into a form suitable for storage. At least one selected from the group consisting of water, ethanol, various buffer solutions and the like may be used as the solvent. The kit may additionally contain, if necessary, at least one selected from the group consisting of exclusive containers, other necessary accessories, instruction manuals, etc.

(4) Use as Detection Marker, etc. by Luminescence

The photoprotein of the present invention can be used as a detection marker by luminescence. The detection marker of the present invention can be used to detect an analyte in, e.g., immunoassay, hybridization assay, etc. The photoprotein of the present invention can be used in the form bound to an analyte (protein, nucleic acid, etc.) by methods conventionally used, such as chemical modification. Detection using such a detection marker can be carried out in a conventional manner. The detection marker of the invention may also be used, for example, by expressing as a fusion protein of the apoprotein and an analyte, inserting the fusion protein into a cell by means of microinjection, etc. and contacting the protein with coelenterazine analog of the invention to produce the photoprotein of the present invention, and then contacting the photoprotein with coelenterazine or its analog, thereby to determine distribution of the analyte described above. As used herein, the term "contact" means that a cell and coelenterazine analog, etc. of the present invention are allowed to be present in the same culture system or reaction system, and includes, for example, coelenterazine analog, etc. of the present invention being added to a culture container charged with a cell, a cell being mixed with coelenterazine analog, etc. of the present invention, a host cell being cultured in the presence of coelenterazine analog, etc. of the present invention, and the like. Examples of the "coelenterazine or its analog" are those described above, in addition to coelenterazine analog of the present invention.

The present invention provides a method for detecting an analyte in immunoassay, hybridization assay, etc., which comprises using coelenterazine analog and the luminescent catalyst. In this case, the luminescent catalyst can be used in the form bound to an analyte (protein, nucleic acid, etc.) by methods conventionally used, such as chemical modification. Detection using such a detection marker can be carried out in a conventional manner. The detection marker may also be used, for example, by expressing as a fusion protein of the luminescent catalyst and an analyte, inserting the fusion protein into a cell by means of microinjection, etc. and contacting the protein with coelenterazine analog of the invention, thus to determine distribution of the analyte described above. As used herein, the term "contact" means that a cell and coelenterazine analog of the present invention are allowed to be present in the same culture system or reaction system, and includes, for example, coelenterazine analog of the present invention being added to a culture container charged with a cell, a cell being mixed with coelenterazine analog of the present invention, a host cell being cultured in the presence of coelenterazine analog of the present invention, and the like.

The luminescent catalyst includes those described above and is at least one selected from the group consisting of *Renilla* luciferase, *Oplophorus* luciferase and *Gaussia* luciferase.

Measurement of the distribution of such an analyte may be carried out using a detection method such as luminescence imaging, etc. Aside from the introduction into a cell by means of microinjection, etc., it is also possible to use the apoprotein by expressing the same within a cell.

The invention also provides a kit used for detecting an analyte in, e.g., immunoassay, hybridization assay, etc. The kit in some embodiments of the present invention comprises the photoprotein of the invention and coelenterazine or its analog. The kit in another embodiment of the present invention comprises coelenterazine analog of the invention and the luminescent catalyst. Reagents including coelenterazine or its analog, the luminescent catalyst, etc. may be dissolved in a suitable solvent and prepared into a form suitable for storage. At least one selected from the group consisting of water, ethanol, various buffer solutions and the like may be used as the solvent. The kit may additionally contain, if necessary, at least one selected from the group consisting of exclusive containers, other necessary accessories, instruction manuals, etc.

(5) Material for Amusement Supplies

The complex (photoprotein of the present invention) composed of the apoprotein and the peroxide of coelenterazine analog of the present invention emits light merely by binding to a trace amount of calcium ions. Therefore, the photoprotein of the invention can be advantageously used as a luminescence substrate in materials for amusement supplies. Examples of amusement supplies include luminescent bubble soap, luminescent ice, luminescent candies, luminescent paints, etc. The amusement supplies of the invention can be prepared in a conventional manner.

(6) Bioluminescence Resonance Energy Transfer (BRET) Method

Coelenterazine analog in some embodiments of the present invention emits light by the action of the luminescent catalyst as described above and can thus be used for the method of analyses, including an analysis of biological functions, an analysis (or measurement) of enzyme activities, etc., based on the principle of intermolecular interactions by the bioluminescence resonance energy transfer (BRET) method. In addition, the photoprotein of the present invention can also be used for the method of analyses such as an analysis of biological functions, measurement of enzyme activities, etc., based on the principle of intermolecular interactions by the bioluminescence resonance energy transfer (BRET) method.

For example, using coelenterazine analog of the present invention in some embodiments of the invention and the luminescent catalyst as donor proteins and an organic compound or a fluorescent protein as an acceptor, the interactions between the proteins can be detected by causing bioluminescence resonance energy transfer (BRET) between them. Herein, the luminescent catalyst includes those described above and is at least one selected from the group consisting of *Renilla* luciferase, *Oplophorus* luciferase and *Gaussia* luciferase. Alternatively, using the photoprotein of the invention as a donor protein and an organic compound or fluorescent protein an acceptor, the interactions between the proteins can be detected by causing bioluminescence resonance energy transfer (BRET) between them. In an embodiment of the present invention, the organic compound used as an acceptor is Hoechst 3342, Indo-1, DAPI, etc. In another embodiment of the present invention, the fluorescent protein used as an acceptor is a green fluorescent protein (GFP), a blue fluorescent protein (BFP), a mutant GFP fluorescent protein, phycobilin, etc. In a preferred embodiment of the present invention, the physiological functions to be analyzed include an orphan receptor (in particular, a G-protein coupled receptor), apoptosis, transcription regulation by gene expression, etc. In a preferred embodiment of the present invention, the enzyme to be analyzed is protease, esterase, kinase, or the like.

Analysis of the physiological functions by the BRET method may be performed by publicly known methods, for example, by modifications of the methods described in Biochem. J. 2005, 385, 625-637, Expert Opin. Ther Tarets, 2007 11: 541-556, etc. Assay for the enzyme activity may also be performed by publicly known methods, for example, by modifications of the methods described in Nat Methods 2006, 3:165-174, Biotechnol J. 2008, 3:311-324, etc.

Furthermore, the present invention provides a kit used for the method of analysis described above. The kit comprises coelenterazine analog of the present invention, the luminescent catalyst, and the organic compound and/or fluorescent protein. Alternatively, the kit comprises the photoprotein of the present invention and the organic compound and/or fluorescent protein. Reagents including coelenterazine analog, the luminescent catalyst, the photoprotein of the invention, the organic compound, the fluorescent protein, etc. may be dissolved in a suitable solvent and prepared into a form suitable for storage. At least one selected from the group consisting of water, ethanol, various buffer solutions and the like may be used as the solvent. The kit may additionally contain, if necessary, at least one selected from the group consisting of exclusive containers, other necessary accessories, instruction manuals, etc.

All literatures and publications mentioned in this specification are herein incorporated in their entirety by reference into the specification, irrespective of their purposes. The specification includes all of the contents as disclosed in the claims, specification and drawings of Japanese Patent Application No. 2009-27921 (filed Feb. 9, 2009), based on which the priority of the present application is enjoyed.

The objects, characteristics, and advantages of the present invention as well as the idea thereof are apparent to those skilled in the art from the descriptions given herein, and those skilled in the art can easily implement the present invention. It is to be understood that the best mode to carry out the invention and specific examples are to be taken as preferred embodiments of the present invention. These descriptions are only for illustrative and explanatory purposes and are not intended to restrict the invention thereto. It is further apparent to those skilled in the art that various modifications may be made based on the descriptions given herein within the intent and scope of the present invention disclosed herein.

In the following EXAMPLES, the ratios of solvent mixtures for chromatography are all by v/v unless otherwise indicated.

EXAMPLES

Synthesis Examples

Outline of Synthesis of Coelenterazine Analog (CTZ Analog)

The outline of synthesis for i-coelenterazine (i-CTZ ($R^1$=I, $R^2$=H, $R^3$=H)), n-coelenterazine (n-CTZ ($R^1$, $R^2$=benzo, $R^3$=H)), me-coelenterazine (me-CTZ ($R^1=CH_3$, $R^2=H$, $R^3=H$)), et-coelenterazine (et-CTZ ($R^1=C_2H_5$, $R^2=H$, $R^3=H$)), cf3-coelenterazine (cf3-CTZ ($R^1=CF_3$, $R^2=H$, $R^3=H$), meo-coelenterazine (meo-CTZ ($R^1=OCH_3$, $R^2=H$, $R^3=H$)), 3me-coelenterazine (3me-CTZ ($R^1=H$, $R^2=CH_3$, $R^3=H$)), 3meo-coelenterazine (3meo-CTZ ($R^1=H$, $R^2=OCH_3$, $R^3=H$)), αmeh-coelenterazine (αmeh-CTZ ($R^1=H$, $R^2=H$, $R^3=CH_3$)) and 3-isocoelenterazine (3iso-CTZ ($R^1=H$, $R^2=OH$, $R^3=H$)) using a keto acetal is as shown below.

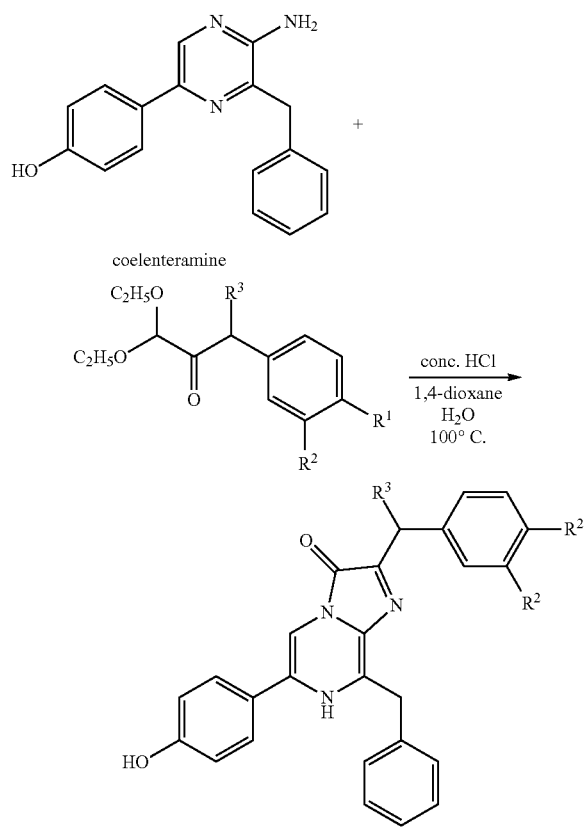

The outline of synthesis for i-coelenterazine (i-CTZ) using a ketoaldehyde is as shown below.

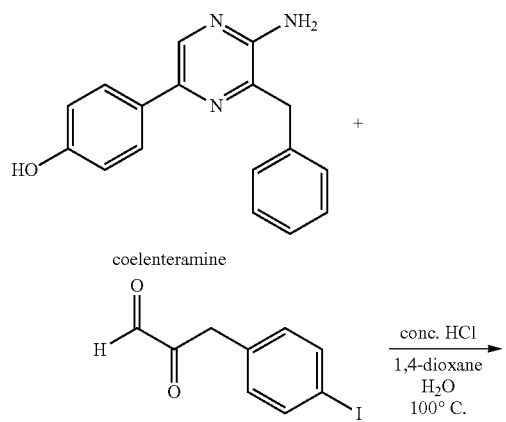

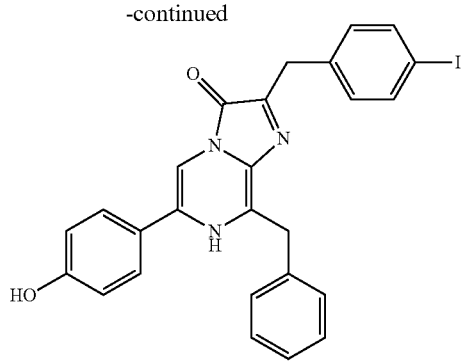

Process

In the synthesis of CTZ analogs, flash column chromatography was performed using silica gel (37563-85 manufactured by Kanto Chemical Co., Inc., Silica Gel 60N (spherical, neutral), and particle size of 40-50 μm), except that acidic silica gel (37562-79 manufactured by Kanto Chemical Co., Inc., Silica Gel 60 (spherical), and particle size of 40-50 μm) was used for the purification of CTZ analogs.

Thin layer chromatography (TLC) was performed using a glass plate (1.05715 manufactured by MERCK Inc., Silica Gel 60 $F_{24}$) precoated with silica gel.

The purity of CTZ analogs was confirmed using high performance liquid chromatography (HPLC): 1100 Series HPLC System manufactured by Agilent Inc.: measurement conditions, column: Lichrosorb (registered trademark) RP-18 (5 μm, 4.0 mm i.d.×125 mm, manufactured by Merck Chemicals); moving phase: gradient 60-100% methanol/ 0.1% aqueous TFA for 40 min; flow rate: 0.45 mL/min; detection: UV 225 nm; volume of injection sample: 0.5 mg/5 mL in methanol/0.1% aqueous TFA=6/4.

Melting point (Mp) was measured on a micro melting point determination apparatus MP-J3 manufactured by YANACO, Inc. (uncorrected data)

Ultraviolet absorption spectra (UV) of CTZ analogs (20 μM methanol solution) were measured at 25° C. in quartz cells (optical path length of 10 mm) with UV-3100 UV-Visible-Near-Infrared Spectrophotometer manufactured by SHIMADZU Corporation under the conditions of high speed at scan speed.

Fluorescence spectra (FL) of CTZ analogs (8 μg/mL methanol) were measured at 25° C. in quartz cells (optical path length of 10 mm) with FP-6500 spectrofluorimeter manufactured by JASCO, under the conditions for excitation wavelength of 330 nm, excitation side bandwidth of 3 nm, fluorescence emission side of 3 nm, response of 0.5 second, sensitivity of medium and scan speed of 100 nm/min.

$^1$H NMR spectra were obtained with a Unity Plus 400 nuclear magnetic resonance spectrometer manufactured by Varian Corp. $^{13}$C NMR spectra were obtained with a JNM-EX270 nuclear magnetic resonance spectrometer manufactured by JEOL Co., Ltd. $^{19}$F NMR spectra were obtained with a Mercury 300 spectrometer manufactured by Varian Corp. $CDCl_3$ or $CD_3OD$ (both manufactured by CIL Inc.) was used as a solvent for the measurement of NMR spectra.

Chemical shifts (δ) were expressed in terms of relative values using, as an internal standard, tetramethylsilane (($CH_3)_4Si$) (measurements of $^1$H NMR in $CDCl_3$; δ 0 ppm), the peak derived from non-deuterated solvent for measurements (measurements of $^1$H NMR in $CD_3OD$; δ 3.31 ppm, measurements of $^{13}$C NMR in $CDCl_3$; δ 77.0 ppm) or hexafluorobenzene (measurements of $^{19}$F NMR; δ 0 ppm).

The binding constant (J) was shown by Hz. Abbreviations s, d, t, q, m and br denote singlet, doublet, triplet, quartet, multiplet, and broad, respectively.

Infrared spectroscopic spectra (IR) were measured by diffuse reflectance method on an IRPrestige-21 Fourier Transform Infrared Spectrophotometer manufactured by SHIMADZU Corporation, equipped with a DRS-8000A diffuse reflectance measuring device.

High resolution mass spectrometric spectra (HRMS) were measured on JMS-700 manufactured by JEOL by the electron impact ionization (EI$^+$) method, or the fast atom bombardment (FAB$^+$) method. In the FAB$^+$ method, m-nitrobenzyl alcohol (NBA) or glycerol was used as a matrix.

Synthesis Example 1

Synthesis of i-coelenterazine (i-CTZ)

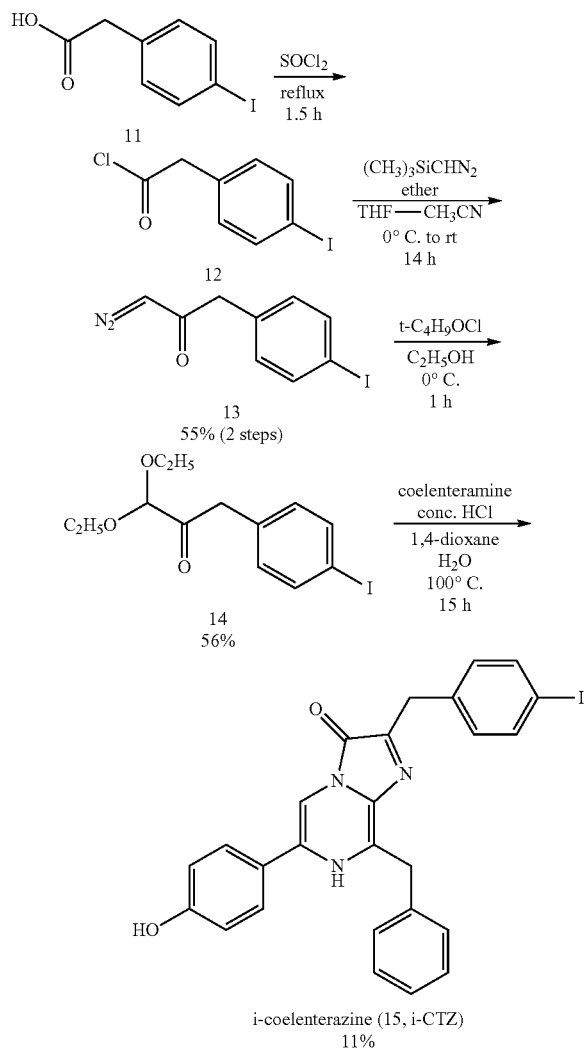

i-coelenterazine (15, i-CTZ)
11%

Synthesis Example 1-1

Under an argon atmosphere, to 4-iodophenylacetic acid (11) (prepared by the process described in Chen, Q.-H. et al., Bioorg. Med. Chem. 14, 7898-7909 (2006)) (1.06 g, 4.05 mmol) was added thionyl chloride (5.00 mL, 68.6 mmol) and heated to reflux (100° C.) for 1.5 h. After cooling to room temperature, the mixture was concentrated under reduced pressure to give 4-iodophenylacetyl chloride (12) as a brown oily crude product, which was used in the next reaction without further purification.

Synthesis Example 1-2

Under an argon atmosphere, 4-iodophenylacetyl chloride (12) prepared above was dissolved in tetrahydrofuran (THF) (2 mL) and acetonitrile (2 mL) and cooled to 0° C. To this was slowly added a solution of trimethylsilyldiazomethane in diethyl ether (2.0 M, 4.00 mL, 8.00 mmol), which was stirred overnight (14 h) after warming up to room temperature. After concentrating under reduced pressure, the residue was purified by silica gel flash column chromatography (n-hexane/diethyl ether=1/1) to give 1-diazo-3-(4-iodophenyl)propan-2-one (13) as a pale yellow solid (635 mg, 2.22 mmol, 54.9%, 2 steps).

TLC R$_f$=0.34 (n-hexane/diethyl ether=1/2);
$^1$H NMR (400 MHz, CDCl$_3$) δ 3.55 (s, 2H), 5.14 (s, 1H), 6.97-7.01 (AA'BB', 2H), 7.65-7.69 (AA'BB', 2H);
$^{13}$C NMR (67.8 MHz, CDCl$_3$) δ 47.3, 55.1, 92.9, 131.4 (2C), 134.2, 137.9 (2C), 191.9;
IR (KBr, cm$^{-1}$) 737, 802, 841, 1007, 1138, 1306, 1371, 1402, 1483, 1630, 2102, 2114, 3076;
HRMS (EI) m/z 285.9597 (M, C$_9$H$_7$IN$_2$O required 285.9603).

Synthesis Example 1-3

Under an argon atmosphere, 1-diazo-3-(4-iodophenyl)propan-2-one (13) (1.11 g, 3.88 mmol) was dissolved in anhydrous ethanol (10 mL) and cooled to 0° C. To this was added tert-butyl hypochlorite (440 μL, 3.89 mmol) and stirred for an hour at the same temperature. After concentrating under reduced pressure, the residue was purified by silica gel flash column chromatography (n-hexane/ethyl acetate=9/1) to give 1,1-diethoxy-3-(4-iodophenyl)propan-2-one (14) as a yellow oily substance (758 mg, 2.18 mmol, 56.1%).

TLC R$_f$=0.27 (n-hexane/ethyl acetate=9/1);
$^1$H NMR (400 MHz, CDCl$_3$) δ 1.25 (t, 6H, J=7.0 Hz), 3.55 (dq, 2H, J=9.5, 7.0 Hz), 3.71 (dq, 2H, J=9.5, 7.0 Hz), 3.83 (s, 2H), 4.61 (s, 1H), 6.94-6.98 (AA'BB', 2H), 7.62-7.66 (AA'BB', 2H);
$^{13}$C NMR (67.8 MHz, CDCl$_3$) δ 15.2 (2C), 43.0, 63.6 (2C), 92.5, 102.6, 131.9 (2C), 133.5, 137.6 (2C), 202.7;
IR (KBr, cm$^{-1}$) 718, 1007, 1061, 1098, 1157, 1315, 1369, 1400, 1443, 1485, 1584, 1643, 1732, 2882, 2928, 2976, 3321;
HRMS (FAB+/NBA) m/z 349.0303 (M+H, C$_{13}$H$_{18}$IO$_3$ required 349.0301).

Synthesis Example 1-4

Under an argon atmosphere, 1,1-diethoxy-3-(4-iodophenyl)propan-2-one (14) (421 mg, 1.21 mmol) was dissolved in 1,4-dioxane (2 mL) and water (0.4 mL). To this was added coelenteramine (prepared by the process described in Adamczyk, M. et al., Org. Prep. Proced. Int., 33, 477-485 (2001)) (222 mg, 801 μmol) and, after cooling to 0° C., conc. hydrochloric acid (0.20 mL) was further added thereto, and then stirred overnight (15 h) at 100° C. After cooling to room temperature, the mixture was concentrated under reduced pressure and the residue was purified by silica gel flash chromatography in an argon flow (n-hexane/ethyl acetate=1/2→ethyl acetate→ethyl acetate/methanol=20/1→10/1).

The solid obtained was further reprecipitated (n-hexane/acetone) to give i-coelenterazine (15, i-CTZ) as an ocher powder (45.2 mg, 84.7 μmol, 10.6%).

TLC $R_f$=0.52 (ethyl acetate/methanol=20/1);
HPLC retention time 21.5 min;
Mp 157-159° C. (dec.);
UV (MeOH) λmax (ε)=259 (24900), 343 (5500), 432 (8300) nm;
FL (MeOH) λmax Em. 545.5 nm;
$^1$H NMR (400 MHz, CD$_3$OD) δ 4.18 (s, 2H), 4.48 (s, 2H), 6.88-6.92 (AA'BB', 2H), 7.09-7.13 (AA'BB', 2H), 7.22-7.42 (m, 5H), 7.55-7.60 (AA'BB', 2H), 7.60-7.66 (AA'BB', 2H), 7.94 (br, $^1$H);
IR (KBr, cm$^{-1}$) 700, 839, 1007, 1171, 1236, 1277, 1506, 1541, 1558, 1609, 1647, 2810, 2934, 2965, 3030, 3059;
HRMS (EI) m/z 533.0587 (M, C$_{26}$H$_{20}$IN$_3$O$_2$ required 533.0600).

Synthesis Example 2

Synthesis of n-coelenterazine (n-CTZ)

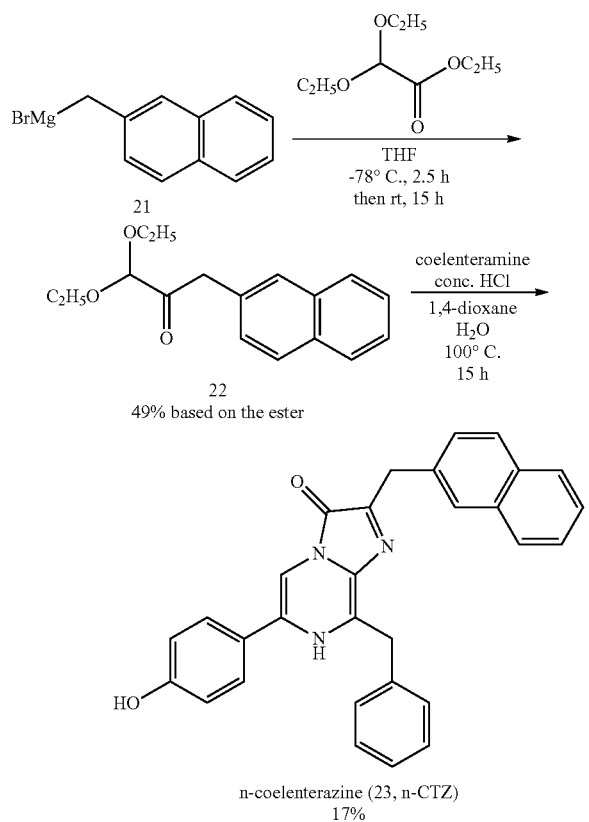

n-coelenterazine (23, n-CTZ)
17%

Synthesis Example 2-1

Under an argon atmosphere, to a solution of ethyl diethoxyacetate (900 μL, 5.06 mmol) in THF (15 mL) was added slowly a diethyl ether solution of (2-naphtalenylmethyl)magnesium bromide (21) (0.25 M, 25.0 mL, 6.25 mmol) at −78° C. After stirring at for 2.5 h at −78° C., the mixture was gradually warmed to room temperature and stirred for 15 h. To this was added 20% aqueous solution of ammonium chloride (10 mL) and the product was extracted with ethyl acetate (×3). The organic layer was sequentially washed with water (×1) and saturated brine (×1), and dried over anhydrous sodium sulfate. After filtration, the mixture was concentrated under reduced pressure and the residue was purified by silica gel flash column chromatography (n-hexane/ethyl acetate=19/1) to give 1,1-diethoxy-3-(2-naphthalenyl)propan-2-one (22) as a colorless oily substance (675 mg, 2.48 mmol, 49.0%).

TLC $R_f$=0.37 (n-hexane/ethyl acetate=9/1);
$^1$H NMR (400 MHz, CDCl$_3$) δ 1.26 (t, 6H, J=7.0 Hz), 3.56 (dq, 2H, J=9.5, 7.0 Hz), 3.72 (dq, 2H, J=9.5, 7.0 Hz), 4.06 (s, 2H), 4.66 (s, 1H), 7.35 (dd, 1H, J=1.8, 8.5 Hz), 7.42-7.49 (m, 2H), 7.69 (s, 1H), 7.76-7.84 (m, 3H);
$^{13}$C NMR (67.8 MHz, CDCl$_3$) δ 15.2 (2C), 43.9, 63.5 (2C), 102.4, 125.7, 126.1, 127.66, 127.69, 128.0, 128.1, 128.5, 131.4, 132.4, 133.5, 203.2;
IR (KBr, cm$^{-1}$) 812, 1017, 1061, 1098, 1125, 1310, 1370, 1508, 1732, 2882, 2928, 2976, 3053;
HRMS (FAB$^+$/NBA+NaI) m/z 295.1316 (M+Na, C$_{17}$H$_{20}$O$_3$Na required 295.1310).

Synthesis Example 2-2

Under an argon atmosphere, 1,1-diethoxy-3-(2-naphthalenyl)propan-2-one (22) (369 mg, 1.35 mmol) was dissolved in 1,4-dioxane (2 mL) and water (0.4 mL). To this was added coelenteramine (310 mg, 1.12 mmol) and, after cooling to 0° C., conc. hydrochloric acid (0.20 mL) was further added thereto, and then stirred at 100° C. overnight (15 hours). After cooling to room temperature, the mixture was concentrated under reduced pressure and the residue was purified by silica gel flash chromatography in an argon flow (n-hexane/ethyl acetate=1/2→ethyl acetate→ethyl acetate/methanol=50/1→20/1). The solid obtained was further reprecipitated (n-hexane/acetone) to give n-coelenterazine (23, n-CTZ) as a yellow powder (88.5 mg, 193 μmol, 17.3%).

TLC $R_f$=0.47 (ethyl acetate/methanol=20/1);
HPLC retention time 20.6 min;
Mp 149-151° C. (dec.);
UV (MeOH) $λ_{max}$ (ε)=262.5 (34500), 349.5 (6400), 432.5 (11700) nm;
FL (MeOH)) $λ_{max}$ Em. 434.5, 544 nm;
$^1$H NMR (400 MHz, CD$_3$OD) δ 4.35 (s, 2H), 4.41 (s, 2H), 6.85-6.91 (AA'BB', 2H), 7.18-7.31 (m, 3H), 7.35-7.45 (m, 4H), 7.46-7.54 (m, 3H), 7.68-7.80 (m, 5H);
IR (KBr, cm$^{-1}$) 698, 760, 815, 839, 1173, 1242, 1277, 1456, 1508, 1541, 1558, 1611, 2812, 2967, 3055, 3152;
HRMS (EI) m/z 457.1778 (M, C$_{30}$H$_{23}$N$_3$O$_2$ required 457.1790).

Synthesis Example 3

Synthesis of me-coelenterazine (me-CTZ)

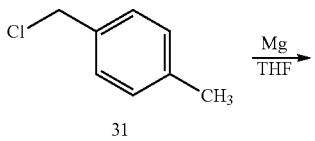

-continued

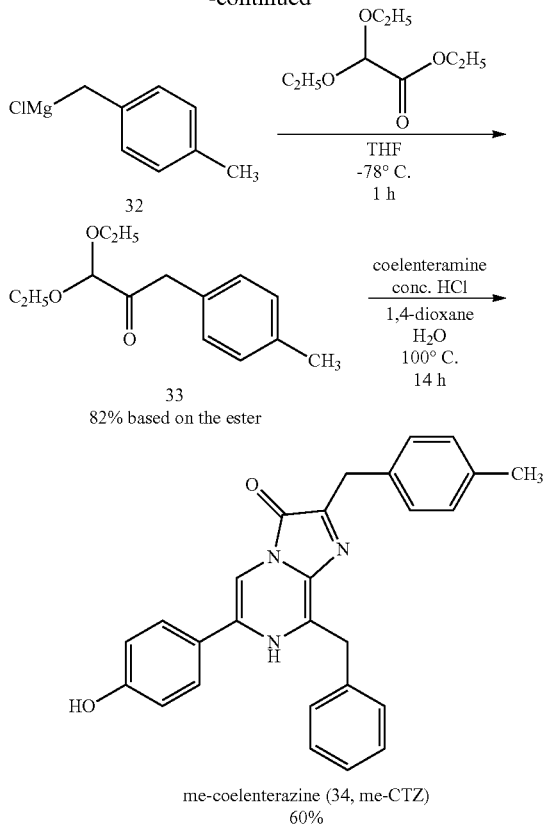

Synthesis Example 3-1

The magnesium turnings (270 mg, 11.1 mmol) were dried in vacuo by heating with a heat gun. After cooling to room temperature and being placed under an argon atmosphere, THF (8 mL) was added thereto, followed by slow addition of 4-methylbenzyl chloride (31) (1.35 mL, 10.2 mmol) at room temperature. The reaction mixture became warm as the result of an exothermic reaction and most of the magnesium turnings were consumed. After cooling to room temperature, it was used directly in the next reaction as a THF solution of (4-methylbenzyl)magnesium chloride (32).

Under an argon atmosphere, to a solution of ethyl diethoxyacetate (1.80 mL, 10.1 mmol) in THF (20 mL) was added slowly a THF solution of (32) prepared above at −78° C. After stirring at −78° C. for an hour, to this was added 20% aqueous solution of ammonium chloride (10 mL) and the product was extracted with ethyl acetate (×3). The organic layer was sequentially washed with water (×1) and saturated brine (×1), and dried over anhydrous sodium sulfate. After filtration, the mixture was concentrated under reduced pressure and the residue was purified by silica gel flash column chromatography (n-hexane/ethyl acetate=9/1) to give 1,1-diethoxy-3-(4-methylphenyl)propan-2-one (33) as a colorless oily substance (1.96 g, 8.27 mmol, 82.4%).

TLC $R_f$=0.45 (n-hexane/ethyl acetate=9/1);

$^1$H NMR (400 MHz, CDCl$_3$) δ 1.25 (t, 6H, J=7.0 Hz), 2.32 (s, 3H), 3.55 (dq, 2H, J=9.5, 7.0 Hz), 3.70 (dq, 2H, J=9.5, 7.0 Hz), 3.85 (s, 2H), 4.63 (s, 1H), 7.08-7.14 (2AA'BB', 4H);

$^{13}$C NMR (67.8 MHz, CDCl$_3$) δ 15.1 (2C), 21.0, 43.3, 63.3 (2C), 102.2, 129.1 (2C), 129.6 (2C), 130.6, 136.3, 203.3;

IR (KBr, cm$^{-1}$) 772, 804, 851, 1022, 1063, 1098, 1146, 1312, 1516, 1732, 2884, 2926, 2976;

HRMS (EI) m/z 236.1409 (M, C$_{14}$H$_{20}$O$_3$ required 236.1412).

Synthesis Example 3-2

Under an argon atmosphere, 1,1-diethoxy-3-(4-methylphenyl)propan-2-one (33) (216 mg, 914 μmol) was dissolved in 1,4-dioxane (2 mL) and water (0.4 mL). To this was added coelenteramine (196 mg, 707 μmol) and, after cooling to 0° C., conc. hydrochloric acid (0.20 mL) was further added thereto, and then stirred overnight (14 hours) at 100° C. After cooling to room temperature, the mixture was concentrated under reduced pressure and the residue was purified by silica gel flash chromatography in an argon flow (n-hexane/ethyl acetate=1/2→ethyl acetate→ethyl acetate/methanol=50/1→20/1). The solid obtained was further reprecipitated (n-hexane/acetone) to give me-coelenterazine (34, me-CTZ) as a yellow powder (180 mg, 427 μmol, 60.4%).

TLC $R_f$=0.51 (ethyl acetate/methanol=20/1);

HPLC retention time 17.1 min;

Mp 150-152° C. (dec.);

UV (MeOH) λ$_{max}$ (ε)=260 (20900), 351 (4600), 437.5 (8600) nm;

FL (MeOH) λ$_{max}$ Em. 433.5, 545 nm;

$^1$H NMR (400 MHz, CD$_3$OD) δ2.29 (s, 3H), 4.22 (s, 2H), 4.52 (s, 2H), 6.88-6.93 (AA'BB', 2H), 7.09-7.14 (AA'BB', 2H), 7.15-7.20 (AA'BB', 2H), 7.22-7.34 (m, 3H), 7.38-7.42 (m, 2H), 7.67-7.73 (AA'BB', 2H), 8.23 (br, $^1$H);

IR (KBr, cm$^{-1}$) 700, 820, 843, 1171, 1238, 1279, 1508, 1541, 1589, 1609, 2812, 2924, 3028;

HRMS (FAB$^+$/glycerol) m/z 422.1880 (M+H, C$_{27}$H$_{24}$N$_3$O$_2$ required 422.1869).

Synthesis Example 4

Synthesis of et-coelenterazine (et-CTZ)

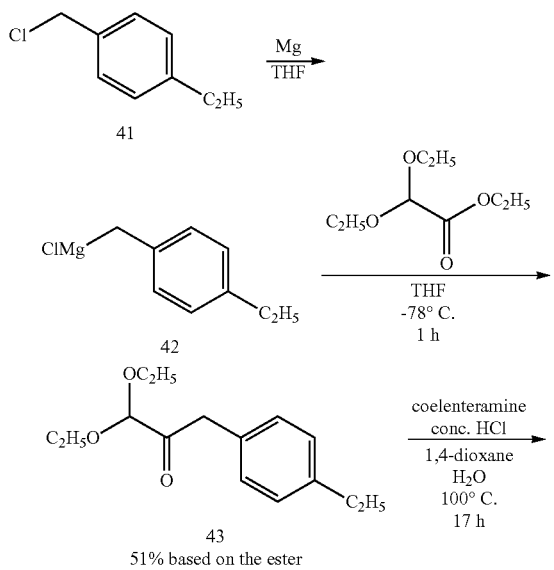

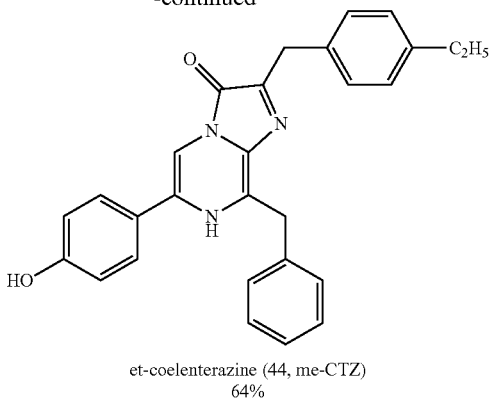

et-coelenterazine (44, me-CTZ)
64%

Synthesis Example 4-1

The magnesium turnings (273 mg, 11.2 mmol) were dried in vacuo by heating with a heat gun. After cooling to room temperature and being placed under an argon atmosphere, THF (8 mL) was added thereto, followed by slow addition of 4-ethylbenzyl chloride (41) (1.48 mL, 9.95 mmol) at room temperature. The reaction mixture became warm as the result of an exothermic reaction and most of magnesium turnings were consumed. After cooling to room temperature, it was used directly in the next reactions as a THE solution of (4-ethylbenzyl)magnesium chloride (42).

Under an argon atmosphere, to a solution of ethyl diethoxyacetate (1.80 mL, 10.1 mmol) in THF (20 mL) was added slowly a THF solution (42) of (4-ethylbenzyl)magnesium chloride prepared above at −78° C. After stirring at −78° C. for an hour, to this was added 20% aqueous solution of ammonium chloride (10 mL), and the product was extracted with ethyl acetate (×3). The organic layer was sequentially washed with water (×1) and saturated brine (×1), and dried over anhydrous sodium sulfate. After filtration, the mixture was concentrated under reduced pressure and the residue was purified by silica gel flash column chromatography (n-hexane/ethyl acetate=9/1) to give 1,1-diethoxy-3-(4-ethylphenyl)propan-2-one (43) as a colorless oily substance (1.29 g, 5.04 mmol, 50.6%).

TLC $R_f$=0.43 (n-hexane/ethyl acetate=9/1)

$^1$H NMR (400 MHz, CDCl$_3$) □ δ 1.22 (t, 3H, J=7.6 Hz), 1.25 (t, 6H, J=7.0 Hz), 2.63 (q, 2H, J=7.6 Hz), 3.55 (dq, 2H, J=9.5, 7.0 Hz), 3.70 (dq, 2H, J=9.5, 7.0 Hz), 3.86 (s, 2H), 4.63 (s, 1H), 7.10-7.17 (2AA'BB', 4H);

$^{13}$C NMR (67.8 MHz, CDCl$_3$) δ 15.1 (2C), 15.5, 28.4, 43.2, 63.2 (2C), 102.2, 127.9 (2C), 129.6 (2C), 130.8, 142.6, 203.2;

IR (KBr, cm$^{-1}$) 810, 853, 1022, 1061, 1099, 1151, 1314, 1514, 1732, 2874, 2930, 2974;

HRMS (EI) m/z 250.1566 (M, C$_{15}$H$_{22}$O$_3$ required 250.1569).

Synthesis Example 4-2

Under an argon atmosphere, 1,1-diethoxy-3-(4-ethylphenyl)propan-2-one (43) (301 mg, 1.20 mmol) was dissolved in 1,4-dioxane (2 mL) and water (0.4 mL). To this was added coelenteramine (238 mg, 858 μmol) and, after cooling to 0° C., conc. hydrochloric acid (0.20 mL) was further added thereto, and then stirred overnight (17 hours) at 100° C. After cooling to room temperature, the mixture was concentrated under reduced pressure and the residue was purified by silica gel flash chromatography in an argon flow (n-hexane/ethyl acetate=1/2→ethyl acetate→ethyl acetate/methanol=50/1→10/1). The solid obtained was further reprecipitated (n-hexane/acetone) to give et-coelenterazine (44, et-CTZ) as a yellow powder (240 mg, 551 μmol, 64.2%).

TLC $R_f$=0.52 (ethyl acetate/methanol=20/1);

HPLC retention time 20.5 min;

Mp 145-147° C. (dec.);

UV (MeOH) $\lambda_{max}$ (ε)=259.5 (22300), 342.5 (5000), 434.5 (8800) nm;

FL (MeOH) $\lambda_{max}$ Em. 433, 546.5 nm;

$^1$H NMR (400 MHz, CD$_3$OD) δ 1.19 (t, 3H, J=7.6 Hz), 2.60 (q, 2H, J=7.6 Hz), 4.24 (s, 2H), 4.53 (s, 2H), 6.88-6.96 (AA'BB', 2H), 7.17-7.22 (2AA'BB', 4H), 7.24-7.34 (m, 3H), 7.38-7.43 (m, 2H), 7.69-7.75 (AA'BB', 2H), 8.26 (br, $^1$H);

IR (KBr, cm$^{-1}$) 700, 820, 840, 1171, 1238, 1277, 1508, 1541, 1589, 1609, 1647, 2893, 2930, 2963, 3028;

HRMS (FAB$^+$/glycerol) m/z 436.2026 (M+H, C$_{28}$H$_{26}$N$_3$O$_2$ required 436.2025).

Synthesis Example 5

Synthesis of cf3-coelenterazine (cf3-CTZ)

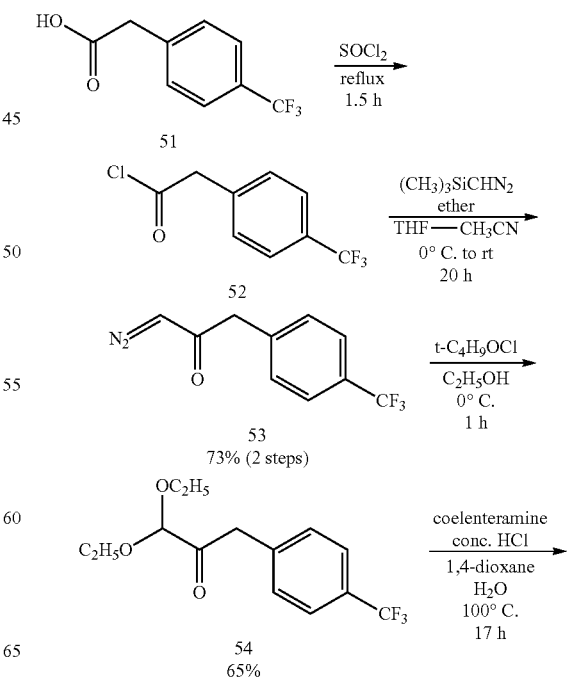

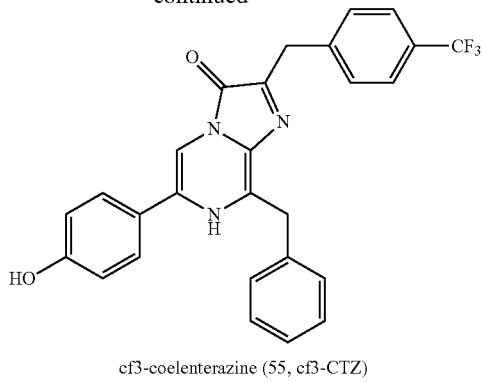

cf3-coelenterazine (55, cf3-CTZ)
62%

Synthesis Example 5-1

Under an argon atmosphere, to 4-trifluoromethylphenylacetic acid (51) (817 mg, 4.00 mmol) was added thionyl chloride (5.00 mL, 68.9 mmol), and heated to reflux (100° C.) for 1.5 h. After cooling to room temperature, the mixture was concentrated under reduced pressure to give 4-trifluoromethylphenylacetyl chloride (52) as a brown oily crude product, which was used in the next reaction without further purification.

Synthesis Example 5-2

Under an argon atmosphere, p-trifluoromethylphenylacetyl chloride (52) prepared above was dissolved in THF (2 mL) and acetonitrile (2 mL), and cooled to 0° C. To this was slowly added a solution of trimethylsilyldiazomethane in diethyl ether (2.0 M, 4.00 mL, 8.00 mmol), which was stirred overnight (20 hours) after warming up to room temperature. After being concentrated under reduced pressure, the residue was purified by silica gel flash column chromatography (n-hexane/diethyl ether=1/1) to give 1-diazo-3-[4-(trifluoromethyl)phenyl]propan-2-one (53) as a pale yellow oily substance (666 mg, 2.92 mmol, 72.9%, 2 steps).

TLC $R_f$=0.31 (n-hexane/diethyl ether=1/2);
$^1$H NMR (400 MHz, CDCl$_3$) δ 3.68 (s, 2H), 5.18 (s, 1H), 7.34-7.40 (AA'BB', 2H), 7.59-7.63 (AA'BB', 2H);
$^{13}$C NMR (67.8 MHz, CDCl$_3$) δ 47.4, 55.3, 124.2 (q, $^1J_{C-F}$=271.9 Hz), 125.7 (2C, q, $^3J_{C-F}$=3.8 Hz), 129.1 (q, $^2J_{C-F}$=32.4 Hz), 129.8 (2C), 138.6, 191.4;
$^{19}$F NMR (282 MHz, CDCl$_3$) δ 99.3 (s);
IR (KBr, cm$^{-1}$) 743, 824, 854, 1020, 1067, 1119, 1164, 1325, 1366, 1420, 1620, 1634, 1639, 2107, 3086;
HRMS (EI) m/z 228.0511 (M, C$_{10}$H$_7$F$_3$N$_2$O required 228.0510).

Synthesis Example 5-3

Under an argon atmosphere, 1-diazo-3-[4-(trifluoromethyl)phenyl]propan-2-one (53) (661 mg, 2.90 mmol) was dissolved in anhydrous ethanol (6 mL) and cooled to 0° C. To this was added tert-butyl hypochlorite (330 µL, 2.92 mmol) and stirred for an hour at the same temperature. After being concentrated under reduced pressure, the residue was purified by silica gel flash column chromatography (n-hexane/ethyl acetate=18/1) to give 1,1-diethoxy-3-[4-(trifluoromethyl) phenyl]propan-2-one (54) as a colorless oily substance (544 mg, 1.87 mmol, 64.7%).

TLC $R_f$=0.29 (n-hexane/ethyl acetate=9/1);
$^1$H NMR (400 MHz, CDCl$_3$) δ 1.26 (t, 6H, J=7.0 Hz), 3.57 (dq, 2H, J=9.2, 7.0 Hz), 3.74 (dq, 2H, J=9.2, 7.0 Hz), 3.96 (s, 2H), 4.62 (s, 1H), 7.30-7.35 (AA'BB', 2H), 7.54-7.60 (AA'BB', 2H);
$^{13}$C NMR (67.8 MHz, CDCl$_3$) δ 15.2 (2C), 43.0, 63.7 (2C), 102.8, 124.3 (q, $^1J_{C-F}$=271.9 Hz), 125.3 (2C, q, $^3J_{C-F}$=3.8 Hz), 129.6 (q, $^2J_{C-F}$=32.4 Hz), 130.3 (2C), 138.1, 202.4;
$^{19}$F NMR (282 MHz, CDCl$_3$) δ 99.3 (s);
IR (KBr, cm$^{-1}$) 864, 1020, 1067, 1109, 1125, 1165, 1325, 1732, 2884, 2934, 2980;
HRMS (FAB$^+$/NBA+NaI) m/z 313.1031 (M+Na, C$_{14}$H$_{17}$F$_3$O$_3$Na required 313.1027).

Synthesis Example 5-4

Under an argon atmosphere, 1,1-diethoxy-3-[4-(trifluoromethyl)phenyl]propan-2-one (54) (359 mg, 1.24 mmol) was dissolved in 1,4-dioxane (2 mL) and water (0.4 mL). To this was added coelenteramine (217 mg, 782 µmol) and, after cooling to 0° C., conc. hydrochloric acid (0.20 mL) was further added thereto, and then stirred overnight (17 hours) at 100° C. After cooling to room temperature, the mixture was concentrated under reduced pressure and the residue was purified by silica gel flash chromatography in an argon flow (n-hexane/ethyl acetate=1/2→ethyl acetate→ethyl acetate/methanol=20/1→10/1). The solid obtained was further reprecipitated (n-hexane/acetone) to give cf3-coelenterazine (55, cf3-CTZ) as a yellow powder (232 mg, 488 µmol, 62.4%).

TLC $R_f$=0.30 (ethyl acetate/methanol=20/1);
HPLC retention time 19.9 min;
Mp 157-161° C. (dec.);
UV (MeOH) $\lambda_{max}$ (ε)=259 (27000), 341.5 (5600), 440.5 (10500) nm;
FL (MCOH) $\lambda_{max}$ Em. 549.5 nm;
$^1$H NMR (400 MHz, CD$_3$OD) δ 4.37 (s, 2H), 4.55 (s, 2H), 6.90-6.95 (AA'BB', 2H), 7.23-7.34 (m, 3H), 7.39-7.43 (m, 2H), 7.49-7.53 (AA'BB', 2H), 7.61-7.71 (2AA'BB', 4H), 8.23 (br, $^1$H);
$^{19}$F NMR (282 MHz, CDCl$_3$) δ 101.8 (s);
IR (KBr, cm$^{-1}$) 702, 818, 1018, 1067, 1121, 1177, 1327, 1508, 1541, 1593, 1609, 1655, 2814, 2862, 2928, 3032, 3256;
HRMS (FAB$^+$/glycerol) m/z 476.1580 (M+H, C$_{27}$H$_{21}$F$_3$N$_3$O$_2$ required 476.1586).

Synthesis Example 6

Synthesis of meo-coelenterazine (meo-CTZ)

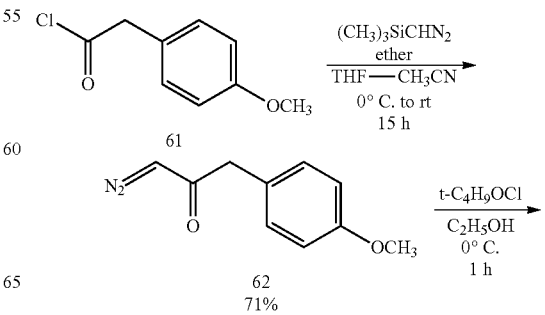

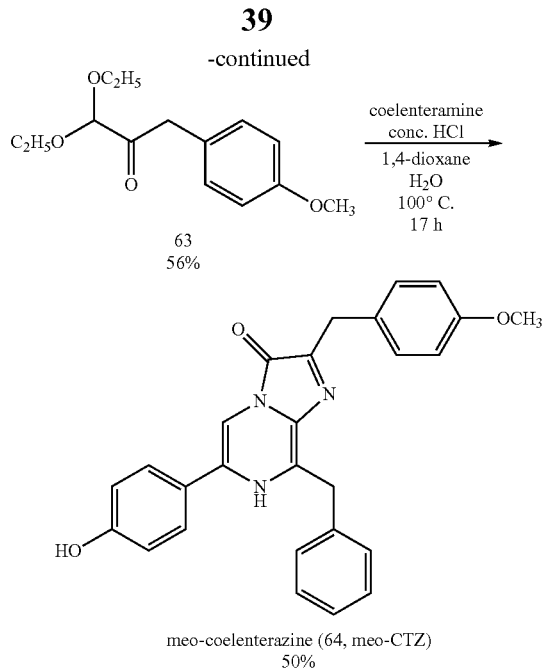

meo-coelenterazine (64, meo-CTZ)
50%

Synthesis Example 6-1

Under an argon atmosphere, 4-methoxyphenylacetyl chloride (61) (952 mg, 5.16 mmol) was dissolved in THF (2.5 mL) and acetonitrile (2.5 mL) and cooled to 0° C. To this was slowly added a solution of trimethylsilyldiazomethane in diethyl ether (2.0 M, 5.00 mL, 10.0 mmol), which was stirred overnight (15 hours) after warming up to room temperature. After concentrating under reduced pressure, the residue was purified by silica gel flash column chromatography (n-hexane/diethyl ether=1/1) to give 1-diazo-3-(4-methoxyphenyl)propan-2-one (62) as a pale yellow oily substance (692 mg, 3.64 mmol, 70.6%).

TLC $R_f$=0.41 (n-hexane/diethyl ether=1/2);

$^1$H NMR (400 MHz, CDCl$_3$) δ 3.56 (s, 2H), 3.81 (s, 3H), 5.11 (s, 1H), 6.85-6.90 (AA'BB', 2H), 7.12-7.18 (AA'BB', 2H);

$^{13}$C NMR (67.8 MHz, CDCl$_3$) δ 47.3, 54.7, 55.3, 114.3 (2C), 126.6, 130.5 (2C), 158.9, 193.4;

IR (KBr, cm$^{-1}$) 821, 851, 943, 1032, 1117, 1179, 1248, 1358, 1512, 1611, 1632, 2102, 2835, 2907, 2934, 3098, 3530;

HRMS (EI) m/z 190.0743 (M, C$_{10}$H$_{10}$N$_2$O$_2$ required 190.0742).

Synthesis Example 6-2

Under an argon atmosphere, 1-diazo-3-(4-methoxyphenyl)propan-2-one (62) (477 mg, 2.51 mmol) was dissolved in anhydrous ethanol (5 mL) and cooled to 0° C. To this was added tert-butyl hypochlorite (285 μL, 2.52 mmol) and stirred for an hour at the same temperature. After concentrating under reduced pressure, the residue was purified by silica gel flash column chromatography (n-hexane/ethyl acetate=10/1) to give 1,1-diethoxy-3-(4-methoxyphenyl)propan-2-one (63) as a colorless oily substance (357 mg, 1.41 mmol, 56.4%).

TLC $R_f$=0.29 (n-hexane/ethyl acetate=9/1);

$^1$H NMR (400 MHz, CDCl$_3$) δ 1.25 (t, 6H, J=7.0 Hz), 3.55 (dq, 2H, J=9.5, 7.0 Hz), 3.70 (dq, 2H, J=9.5, 7.0 Hz), 3.79 (s, 3H), 3.83 (s, 2H), 4.63 (s, 1H), 6.83-6.91 (AA'BB', 2H), 7.10-7.17 (AA'BB', 2H);

$^{13}$C NMR (67.8 MHz, CDCl$_3$) δ 15.2 (2C), 42.9, 55.3, 63.4 (2C), 102.3, 114.0 (2C), 125.8, 130.8 (2C), 158.6, 203.6;

IR (KBr, cm$^{-1}$) 1036, 1063, 1098, 1177, 1512, 1612, 1732, 2835, 2897, 2933, 2976;

HRMS (EI) m/z 252.1360 (M, C$_{14}$H$_{20}$O$_4$ required 252.1362).

Synthesis Example 6-3

Under an argon atmosphere, 1,1-diethoxy-3-(4-methoxyphenyl)propan-2-one (63) (355 mg, 1.41 mmol) was dissolved in 1,4-dioxane (2 mL) and water (0.4 mL). To this was added coelenteramine (221 mg, 797 mol) and, after cooling to 0° C., conc. hydrochloric acid (0.20 mL) was further added thereto, and then stirred overnight (17 hours) at 100° C. After cooling to room temperature, the mixture was concentrated under reduced pressure and the residue was purified by silica gel flash chromatography in an argon flow (n-hexane/ethyl acetate=1/2→ethyl acetate→ethyl acetate/methanol=20/1→10/1). The solid obtained was further reprecipitated (n-hexane/acetone) to give meo-coelenterazine (64, meo-CTZ) as an ocher powder (174 mg, 398 mmol, 49.9%).

TLC $R_f$=0.31 (ethyl acetate/methanol=20/1);

HPLC retention time 13.7 min;

Mp 137-139° C. (dec.);

UV (MeOH) $\lambda_{max}$ (ε)=267 (26000), 344.5 (7400), 435 (8500) nm;

FL (MeOH) $\lambda_{max}$ Em. 435.5, 549 nm;

$^1$H NMR (400 MHz, CD$_3$OD) δ 3.75 (s, 3H), 4.21 (s, 2H), 4.54 (s, 2H), 6.84-6.94 (2AA'BB', 4H), 7.18-7.36 (m, 5H), 7.38-7.43 (m, 2H), 7.69-7.75 (AA'BB', 2H), 8.31 (br, $^1$H);

IR (KBr, cm$^{-1}$) 820, 839, 1177, 1248, 1508, 1558, 1585, 1609, 1647, 2835, 2951, 3030, 3063;

HRMS (FAB$^+$/glycerol) m/z 438.1814 (M+H, C$_{27}$H$_{24}$N$_3$O$_3$ required 438.1818).

Synthesis Example 7

Synthesis of 3me-coelenterazine (3me-CTZ)

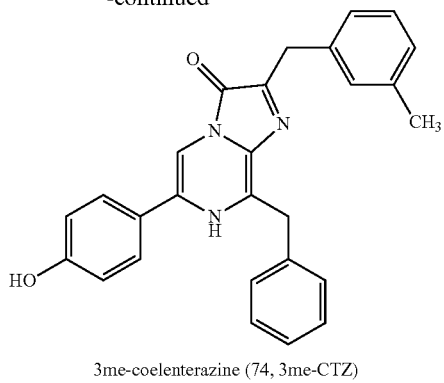

3me-coelenterazine (74, 3me-CTZ)
48%

Synthesis Example 7-1

The magnesium turnings (271 mg, 11.1 mmol) were dried in vacuo by heating with a heat gun. After cooling to room temperature and being placed under an argon atmosphere, THF (8 mL) was added thereto, followed by slow addition of 3-methylbenzyl chloride (71) (1.35 mL, 10.2 mmol) at room temperature. The reaction mixture became warm as the result of an exothermic reaction and most of the magnesium turnings were consumed. After cooling to room temperature, it was used directly in the next reaction as a THF solution of (3-methylbenzyl)magnesium chloride (72).

Under an argon atmosphere, to a solution of ethyl diethoxyacetate (1.80 mL, 10.1 mmol) in THF (20 mL) was added slowly a THF solution of (72) prepared above at −78° C. After stirring at −78° C. for an hour, to this was added 20% aqueous solution of ammonium chloride (10 mL) and the product was extracted with ethyl acetate (×3). The organic layer was sequentially washed with water (×1) and saturated brine (×1), and dried over anhydrous sodium sulfate. After filtration, the mixture was concentrated under reduced pressure and the residue was purified by silica gel flash column chromatography (n-hexane/ethyl acetate=9/1) to give 1,1-diethoxy-3-(3-methylphenyl)propan-2-one (73) as a colorless oily substance (1.38 g, 5.84 mmol, 58.0%).

TLC $R_f$=0.40 (n-hexane/ethyl acetate=9/1);
$^1$H NMR (400 MHz, CDCl$_3$) δ 1.25 (t, 6H, J=7.0 Hz), 2.33 (s, 3H), 3.55 (dq, 2H, J=9.5,
7.0 Hz), 3.70 (dq, 2H, J=9.5, 7.0 Hz), 3.85 (s, 2H), 4.63 (s, 1H), 6.99-7.08 (m, 3H), 7.18-7.23 (m, 1H);
$^{13}$C NMR (67.8 MHz, CDC$_3$) δ 15.2 (2C), 21.4, 43.7, 63.4 (2C), 102.3, 126.8, 127.6, 128.4, 130.6, 133.7, 138.1, 203.3;
IR (KBr, cm$^{-1}$) 700, 758, 1063, 1099, 1157, 1314, 1736, 2880, 2928, 2976;
HRMS (FAB$^+$/NBA+NaI) m/z 259.1307 (M+Na, C$_{14}$H$_{20}$O$_3$Na required 259.1310).

Synthesis Example 7-2

Under an argon atmosphere, 1,1-diethoxy-3-(3-methylphenyl)propan-2-one (73) (265 mg, 1.12 mmol) was dissolved in 1,4-dioxane (2 mL) and water (0.4 mL). To this was added coelenteramine (202 mg, 728 μmol) and, after cooling to 0° C., conc. hydrochloric acid (0.20 mL) was further added thereto, and then stirred overnight (17 hours) at 100° C. After cooling to room temperature, the mixture was concentrated under reduced pressure and the residue was purified by silica gel flash chromatography in an argon flow (n-hexane/ethyl acetate=1/2→ethyl acetate→ethyl acetate/methanol=50/1→20/1). The solid obtained was further reprecipitated (n-hexane/acetone) to give 3me-coelenterazine (74, 3me-CTZ) as a yellow powder (148 mg, 351 mmol, 48.2%).

TLC $R_f$=0.52 (ethyl acetate/methanol=20/1);
HPLC retention time 17.1 min;
Mp 142-145° C. (dec.);
UV (MeOH) $λ_{max}$ (ε)=260 (22500), 349.5 (5100), 435 (8900) nm;
FL (MeOH) $λ_{max}$ Em. 437, 547 nm;
$^1$H NMR (400 MHz, CD$_3$OD) δ 2.29 (s, 3H). 4.24 (s, 2H), 4.54 (s, 2H), 6.88-6.94 (AA'BB', 2H), 7.03-7.14 (m, 3H), 7.16-7.21 (m, 1H), 7.22-7.34 (m, 3H), 7.39-7.43 (m, 2H), 7.69-7.77 (AA'BB', 2H), 8.30 (br, 1H);
IR (KBr, cm$^{-1}$) 700, 748, 820, 841, 1171, 1236, 1277, 1506, 1541, 1589, 1608, 1647, 2862, 2922, 3028;
HRMS (FAB$^+$/glycerol) m/z 422.1863 (M+H, C$_{27}$H$_{24}$N$_3$O$_2$ required 422.1869).

Synthesis Example 8

Synthesis of 3meo-coelenterazine (3meo-CTZ)

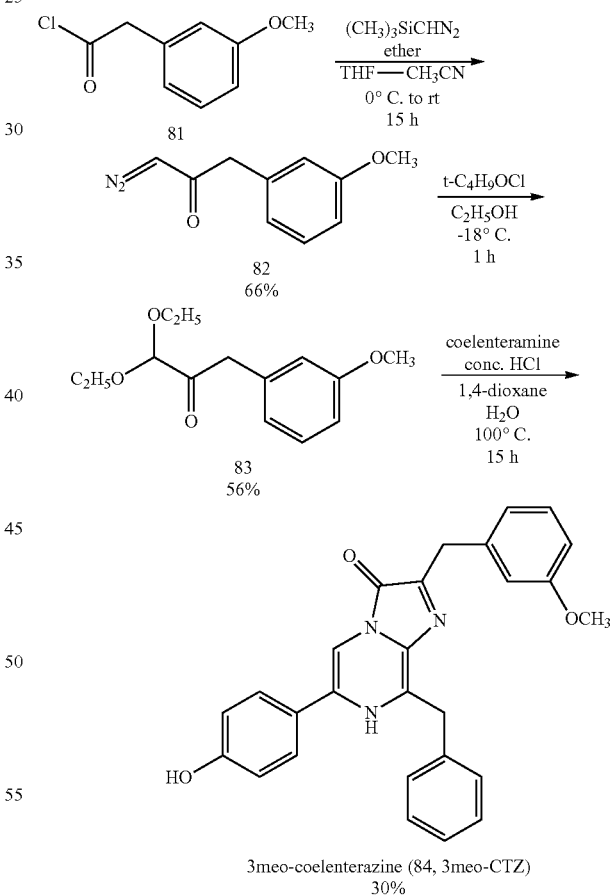

3meo-coelenterazine (84, 3meo-CTZ)
30%

Synthesis Example 8-1

Under an argon atmosphere, 3-methoxyphenylacetyl chloride (81) (952 mg, 5.16 mmol) was dissolved in THF (2.5 mL) and acetonitrile (2.5 mL) and cooled to 0° C. To this was slowly added a solution of trimethylsilyldiazomethane in diethyl ether (2.0 M, 5.00 mL, 10.0 mmol), which was stirred overnight (15 hours) after warming up to room temperature. After concentrating under reduced pressure, the residue was purified by silica gel flash column chromatography (n-hexane/diethyl ether=3/2) to give 1-diazo-3-(3-methoxyphenyl) propan-2-one (82) as a pale yellow oily substance (650 mg, 3.42 mmol, 66.3%).

TLC $R_f$=0.38 (n-hexane/diethyl ether=1/2);
$^1$H NMR (400 MHz, CDCl$_3$) δ 3.59 (s, 2H), 3.81 (s, 3H), 5.14 (s, 1H), 6.76-6.86 (m, 3H), 7.23-7.29 (m, 1H);
$^{13}$C NMR (67.8 MHz, CDCl$_3$) δ 47.9, 54.7, 55.0, 112.6, 114.9, 121.6, 129.7, 135.9, 159.8, 192.6;
IR (KBr, cm$^{-1}$) 691, 764, 876, 949, 1047, 1076, 1150, 1258, 1358, 1489, 1584, 1631, 2104, 2835, 2940, 3003, 3580;
HRMS (EI) m/z 190.0740 (M, C$_{10}$H$_{10}$N$_2$O$_2$ required 190.0742).

Synthesis Example 8-2

Under an argon atmosphere, 1-diazo-3-(3-methoxyphenyl)propan-2-one (82) (501 mg, 2.63 mmol) was dissolved in anhydrous ethanol (5 mL) and cooled to −18C. To this was added tert-butyl hypochlorite (300 µL, 2.65 mmol) and stirred for an hour at the same temperature. After concentrating under reduced pressure, the residue was purified by silica gel flash column chromatography (n-hexane/ethyl acetate=10/1) to give 1,1-diethoxy-3-(3-methoxyphenyl)propan-2-one (83) as a pale yellow oily substance (371 mg, 1.47 mmol, 55.8%).

TLC $R_f$=0.27 (n-hexane/ethyl acetate=9/1);
$^1$H NMR (400 MHz, CDCl$_3$) δ 1.25 (t, 6H, J=7.0 Hz), 3.55 (dq, 2H, J=9.5, 7.0 Hz), 3.70 (dq, 2H, J=9.5, 7.0 Hz), 3.79 (s, 3H), 3.86 (s, 2H), 4.64 (s, 1H), 6.74-6.83 (m, 3H), 7.21-7.25 (m, 1H);
$^{13}$C NMR (67.8 MHz, CDCl$_3$) δ 15.2 (2C), 43.8, 55.2, 63.4 (2C), 102.3, 112.5, 115.4, 122.2, 129.4, 135.2, 159.7, 203.1;
IR (KBr, cm$^{-1}$) 1057, 1098, 1150, 1260, 1585, 1732, 2835, 2886, 2934, 2976;
HRMS (FAB$^+$/NBA+KCl) m/z 291.0992 (M+K, C$_{14}$H$_{20}$O$_4$K required 291.0999).

Synthesis Example 8-3

Under an argon atmosphere, 1,1-diethoxy-3-(3-methoxyphenyl)propan-2-one (83) (254 mg, 1.01 mmol) was dissolved in 1,4-dioxane (2 mL) and water (0.4 mL). To this was added coelenteramine (209 mg, 754 µmol) and, after cooling to 0° C., conc. hydrochloric acid (0.20 mL) was further added thereto, and then stirred overnight (15 hours) at 100° C. After cooling to room temperature, the mixture was concentrated under reduced pressure and the residue was purified by silica gel flash chromatography in an argon flow (n-hexane/ethyl acetate=1/2→ethyl acetate→ethyl acetate/methanol=20/1→10/1) (×2). The solid obtained was further reprecipitated (n-hexane/acetone) to give 3meo-coelenterazine (84, 3meo-CTZ) as an ocher powder (98.7 mg, 226 µmol, 29.9%).

TLC $R_f$=0.33 (ethyl acetate/methanol=20/1);
HPLC retention time 13.8 min;
Mp 136-140° C. (dec.);
UV (MeOH) $\lambda_{max}$ (ε)=262 (25600), 346.5 (5400), 438.5 (9900) nm;
FL (MeOH) $\lambda_{max}$ Em. 428.5, 543.5 nm;
$^1$H NMR (400 MHz, CD$_3$OD) δ 3.75 (s, 3H), 4.25 (s, 2H), 4.55 (s, 2H), 6.77 (dd, 1H, J=1.9, 8.0 Hz), 6.84-6.92 (m, 4H), 7.16-7.34 (m, 4H), 7.38-7.44 (m, 2H), 7.63-7.70 (AA'BB', 2H), 8.17 (br, $^1$H);
IR (KBr, cm$^{-1}$) 700, 750, 839, 1045, 1170, 1260, 1506, 1541, 1595, 1608, 1647, 2835, 2938, 3030, 3059;
HRMS (FAB$^+$/glycerol) m/z 438.1814 (M+H, C$_{27}$H$_{24}$N$_3$O$_3$ required 438.1818).

Synthesis Example 9

Synthesis of αmeh-coelenterazine (αmeh-CTZ)

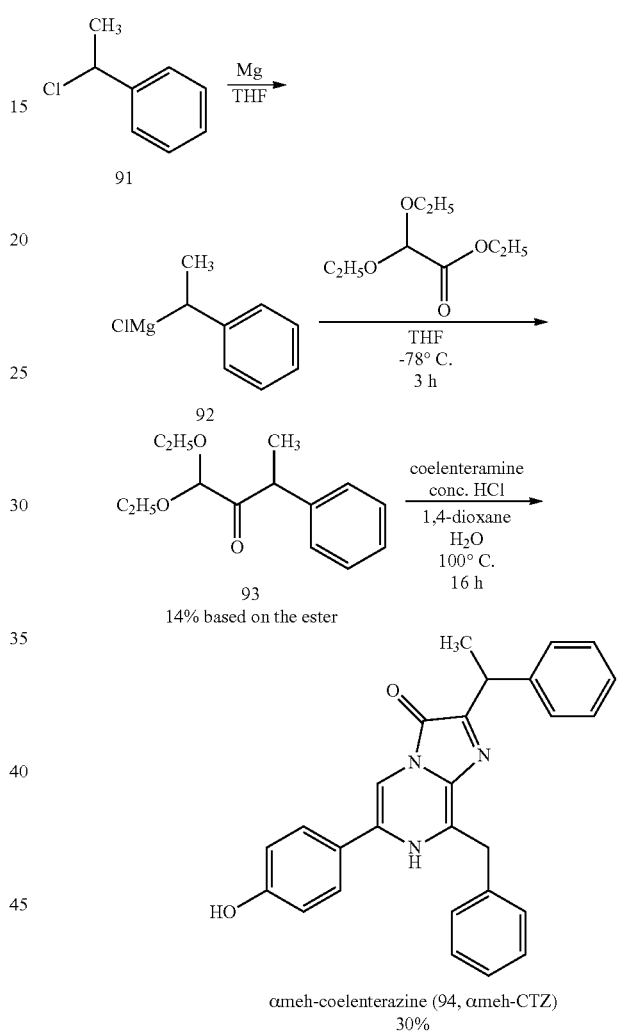

αmeh-coelenterazine (94, αmeh-CTZ)
30%

Synthesis Example 9-1

The magnesium turnings (274 mg, 11.3 mmol) were dried in vacuo by heating with a heat gun. After cooling to room temperature and being placed under an argon atmosphere, THF (8 mL) was added thereto, followed by slow addition of 1-chloroethylbenzene (91) (1.35 mL, 10.2 mmol) at room temperature. The reaction mixture became warm as the result of an exothermic reaction and most of magnesium turnings were consumed. After cooling to room temperature, it was used directly in the next reaction as a THF solution of (1-phenylethyl)magnesium chloride (92).

Under an argon atmosphere, to a solution of ethyl diethoxyacetate (1.80 mL, 10.1 mmol) in THF (20 mL) was added slowly a THF solution of (92) prepared above at −78°

C. After stirring at −78° C. for 3 hours, to this was added 20% aqueous solution of ammonium chloride (10 mL) and the product was extracted with ethyl acetate (×3). The organic layer was sequentially washed with water (×1) and saturated brine (×1), and dried over anhydrous sodium sulfate. After filtration, the mixture was concentrated under reduced pressure and the residue was purified by silica gel flash column chromatography (n-hexane/ethyl acetate=19/1) to give 1,1-diethoxy-3-phenylbutan-2-one (93) as a colorless oily substance (330 mg, 1.37 mmol, 13.7%).

TLC $R_f$=0.43 (n-hexane/ethyl acetate=9/1);

$^1$H NMR (400 MHz, CDCl$_3$) □ δ 1.13 (t, 3H, J=7.0 Hz), 1.20 (t, 3H, J=7.0 Hz), 1.41 (d, 3H, J=7.0 Hz), 3.32 (dq, 1H, J=9.5, 7.0 Hz), 3.47-3.64 (m, 3H), 4.26 (q, 1H, J=7.0 Hz), 4.59 (s, 1H), 7.22-7.36 (m, 5H);

$^{13}$C NMR (67.8 MHz, CDCl$_3$) δ 15.1, 15.2, 18.1, 47.3, 62.8, 63.0, 101.2, 127.1, 128.3 (2C), 128.7 (2C), 140.2, 205.8;

IR (KBr, cm$^{-1}$) 700, 1030, 1063, 1103, 1163, 1452, 1493, 1730, 2874, 2932, 2976;

HRMS (FAB$^+$/NBA+NaI) m/z 237.1496 (M+H, C$_{14}$H$_{21}$O$_3$ required 237.1491).

Synthesis Example 9-2

Under an argon atmosphere, 1,1-diethoxy-3-phenylbutan-2-one (93) (188 mg, 796 μmol) was dissolved in 1,4-dioxane (2 mL) and water (0.4 mL). To this was added coelenteramine (170 mg, 613 μmol) and, after cooling to 0° C., conc. hydrochloric acid (0.20 mL) was further added thereto, and then stirred overnight (16 hours) at 100° C. After cooling to room temperature, the mixture was concentrated under reduced pressure and the residue was purified by silica gel flash chromatography in an argon flow (n-hexane/ethyl acetate=1/2→ethyl acetate→ethyl acetate/methanol=20/1). The solid obtained was further reprecipitated (n-hexane/acetone) to give αmeh-coelenterazine (94, αmeh-CTZ) as a yellow powder (76.5 mg, 181 μmol, 29.6%).

TLC $R_f$=0.53 (ethyl acetate/methanol=20/1);
HPLC retention time 17.6 min;
Mp 143-145° C. (dec.);
UV (MeOH) $\lambda_{max}$ (ε)=259.5 (18800), 350 (4400), 439 (7800) nm;
FL (MeOH) $\lambda_{max}$ Em. 429.5, 551 nm;

$^1$H NMR (400 MHz, CD$_3$OD) δ 1.81 (d, 3H, J=7.3 Hz), 4.56 (q, 1H, J=7.3 Hz), 4.58 (s, 2H), 6.89-6.94 (AA'BB', 2H), 7.18-7.40 (m, 8H), 7.43-7.47 (m, 2H), 7.58-7.65 (AA'BB', 2H), 8.07 (br, $^1$H);

IR (KBr, cm$^{-1}$) 700, 820, 841, 1177, 1215, 1277, 1454, 1508, 1541, 1558, 1610, 1647, 2876, 2934, 2972, 3030, 3059;

HRMS (FAB$^+$/glycerol) m/z 422.1872 (M+H, C$_{27}$H$_{24}$N$_3$O$_2$ required 422.1869).

Synthesis Example 10

Synthesis of 3-isocoelenterazine (3iso-CTZ)

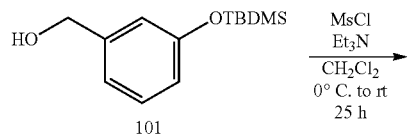

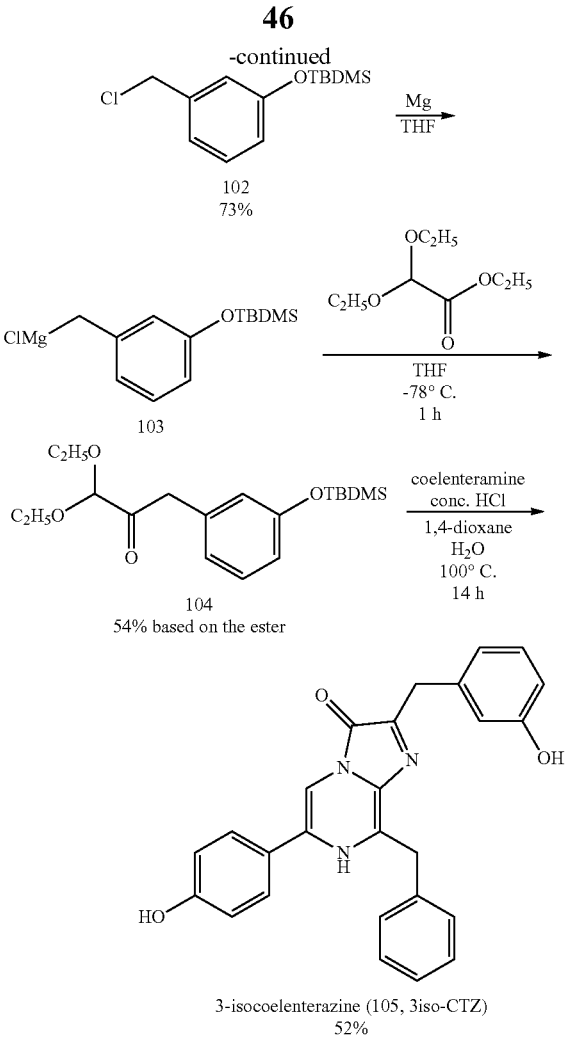

Ms = methanesulfonyl
TBDMS = tert-butyldimethylsilyl

Synthesis Example 10-1

3-(tert-Butyldimethylsilyloxy)benzyl alcohol (101) (prepared by the process described in Wu, Y.-C. et al., J. Am. Chem. Soc., 130, 7148-7152 (2008)) (7.94 g, 31.4 mmol) was dissolved in dichloromethane (150 mL), and cooled to 0° C. To this were sequentially added triethylamine (9.10 mL, 66.7 mmol) and methanesulfonyl chloride (3.80 mL, 49.1 mmol) and stirred for 25 hours after warming up to room temperature. To this was added water, and the product was extracted with dichloromethane (×3). The organic layer was sequentially washed with water (×1) and saturated brine (×1), and dried over anhydrous sodium sulfate. After filtration, the mixture was concentrated under reduced pressure and the residue was purified by silica gel flash column chromatography (n-hexane/ethyl acetate=95/1) to give 3-(tert-butyldimethylsilyloxy)benzyl chloride (102) as a colorless oily substance (5.90 g, 23.0 mmol, 73.1%).

TLC $R_f$=0.45 (n-hexane);

$^1$H NMR (400 MHz, CDCl$_3$) δ 0.20 (s, 6H), 0.99 (s, 9H), 4.53 (s, 2H), 6.79 (dd, 1H, J=1.4, 8.1 Hz), 6.87 (d, 1H, J=1.4 Hz), 6.97 (d, 1H, J=8.1 Hz), 7.20 (dd, 1H, J=8.1, 8.1 Hz).

Synthesis Example 10-2

The magnesium turnings (270 mg, 11.1 mmol) were dried in vacuo by heating with a heat gun. After cooling to room temperature and being placed under an argon atmosphere, THF (17.5 mL) was added thereto, followed by slow addition of 3-(tert-Butyldimethylsilyloxy)benzyl chloride (102) (2.57 g, 10.0 mmol) at room temperature. The reaction mixture was warmed as the result of an exothermic reaction and most of the magnesium turnings were consumed. After cooling to room temperature, it was used directly in the next reaction as a TI-IF solution of 3-(tert-butyldimethylsilyloxy)benzylmagnesium chloride (103) was cooled to room temperature and was used as it was in the next reaction.

Under an argon atmosphere, to a solution of ethyl diethoxyacetate (1.80 mL, 10.1 mmol) in THF (20 mL) was added slowly a THF solution of (103) prepared above at −78° C. After stirring at −78° C. for an hour, to this was added 20% aqueous solution of ammonium chloride (30 mL) and the product was extracted with ethyl acetate (×3). The organic layer was sequentially washed with water (×1) and saturated brine (×1), and dried over anhydrous sodium sulfate. After filtration, the mixture was concentrated under reduced pressure and the residue was purified by silica gel flash column chromatography (n-hexane/ethyl acetate=10/1) to give 3-[3-(tert-butyldimethylsilyloxy]phenyl]-1,1-diethoxypropan-2-one (104) as a colorless oily substance (1.90 g, 5.39 mmol, 53.9%).

TLC $R_f$=0.48 (n-hexanelethyl acetate=10/1);
$^1$H NMR (400 MHz, CDCl$_3$) δ 0.19 (s, 6H), 0.97 (s, 9H), 1.25 (t, 6H, J=7.0 Hz), 3.54 (dq, 2H, J=9.5, 7.0 Hz), 3.69 (dq, 2H, J=9.5, 7.0 Hz), 3.82 (s, 2H), 4.63 (s, 1H), 6.68-6.75 (m, 2H), 6.81 (d, 1H, J=7.8 Hz), 7.16 (dd, 1H, J=7.8, 7.8 Hz);
$^{13}$C NMR (67.8 MHz, CDCl$_3$) δ−4.4 (2C), 15.2 (2C), 18.2, 25.7 (3C), 43.7, 63.3 (2C), 102.2, 118.5, 121.6, 122.8, 129.3, 135.2, 155.7, 202.9;
IR (KBr, cm$^{-1}$) 781, 839, 982, 1063, 1157, 1275, 1487, 1585, 1601, 1736, 2859, 2886, 2930, 2955, 2974;
HRMS (EI) m/z 352.2073 (M, C$_{19}$H$_{32}$O$_4$Si required 352.2070).

Synthesis Example 10-3

Under an argon atmosphere, 3-[3-(tert-butyldimethylsilyloxy)phenyl]-1,1-diethoxypropan-2-one (104) (390 mg, 1.11 mmol) was dissolved in 1,4-dioxane (2 mL) and water (0.4 mL). To this was added coelenteramine (202 mg, 728 μmol) and, after cooling to 0° C., conc. hydrochloric acid (0.20 mL) was added thereto, and then stirred overnight (14 hours) at 100° C. After cooling to room temperature, the mixture was concentrated under reduced pressure and the residue was purified by silica gel flash chromatography in an argon flow (n-hexane/ethyl acetate=1/2→ethyl acetate→ethyl acetate/methanol=20/1). The solid obtained was further reprecipitated (n-hexane/acetone) to give 3-isocoelenterazine (105, 3 iso-CTZ) as a yellow powder (159 mg, 375 μmol, 51.5%).

TLC $R_f$=0.29 (ethyl acetate/methanol=20/1);
HPLC retention time 8.6 min;
Mp 160-162° C. (dec.);
UV (MeOH) $\lambda_{max}$ (ε)=265.5 (19300), 351.5 (4400), 433.5 (7700) nm;
FL (MeOH) $\lambda_{max}$ Em. 429, 549.0 nm;
$^1$H NMR (400 MHz, CD$_3$OD) δ 4.20 (s, 2H), 4.53 (s, 2H), 6.66 (dd, 1H, J=1.4, 8.1 Hz), 6.71-6.77 (m, 2H), 6.88-6.93 (AA'BB', 2H), 7.12 (dd, 1H, J=8.1, 8.1 Hz), 7.22-7.35 (m, 3H), 7.39-7.43 (m, 2H), 7.68-7.75 (AA'BB', 2H), 8.26 (br, $^1$H);
IR (KBr, cm$^{-1}$) 700, 760, 820, 841, 1171, 1238, 1275, 1456, 1506, 1541, 1591, 1608, 2953, 3063, 3150;

HRMS (FAB$^+$/glycerol) m/z 424.1663 (M+H, C$_{26}$H$_{22}$N$_3$O$_3$ required 424.1661).

Comparative Synthesis Example 1

Synthesis of i-coelenterazine (1-CTZ)

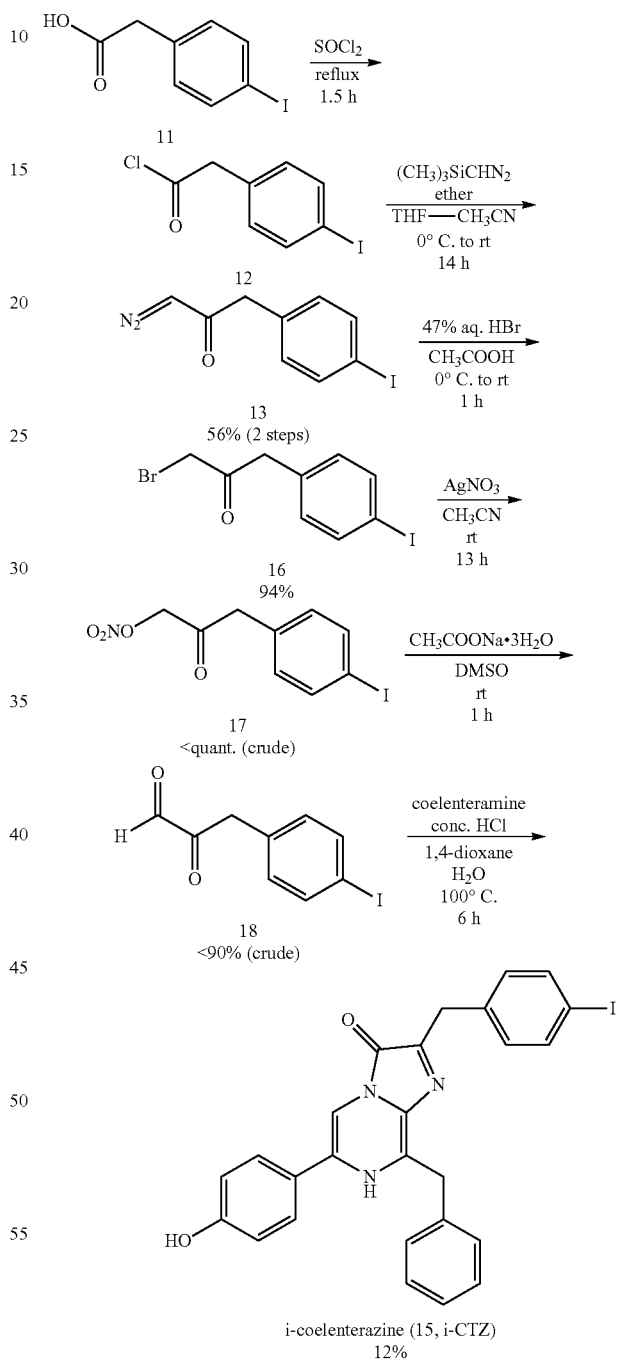

Comparative Synthesis Example 1-1

Under an argon atmosphere, to 4-iodophenylacetic acid (11) (prepared by the process described in Chen, Q.-H. et al., *Bioorg. Med. Chem.*, 14, 7898-7909 (2006)) (1.06 g, 4.05 mmol) was added thionyl chloride (5.00 mL, 68.6 mmol) and heated to reflux (100° C.) for 1.5 h. After cooling to room temperature, the mixture was concentrated under reduced pressure to give 4-iodophenylacetyl chloride (12) as a brown oily crude product.

Under an argon atmosphere, 4-iodophenylacetyl chloride (12) obtained above was dissolved in THF (2 mL) and acetonitrile (2 mL) and cooled to 0° C. To this was slowly added a solution of trimethylsilyldiazomethane in diethyl ether (2.0 M, 4.00 mL, 8.00 mmol), which was stirred overnight (14 h) after warming up to room temperature. After concentrating under reduced pressure, the residue was purified by silica gel flash column chromatography (n-hexane/diethyl ether=1/1) to give 1-diazo-3-(4-iodophenyl)propan-2-one (13) as a pale yellow solid (635 mg, 4.44 mmol, 55.5%, 2 steps).

Comparative Synthesis Example 1-2

1-Diazo-3-(4-iodophenyl)propan-2-one (13) (1.27 g, 4.43 mmol) was dissolved in acetic acid (20 mL) and cooled to 0° C. To this was added 47% hydrobromic acid (1.55 mL, 13.3 mmol) and stirred for an hour after warming to room temperature. After neutralization by adding saturated aqueous solution of sodium bicarbonate, the product was extracted with ethyl acetate (×3) and the organic layer was washed sequentially with saturated aqueous solution of sodium bicarbonate (×1) and saturated brine (×1), and dried over anhydrous sodium sulfate. After filtration, the mixture was concentrated under reduced pressure and the residue was purified by silica gel flash column chromatography (n-hexane/ethyl acetate=7/1) to give 1-bromo-3-(4-iodophenyl)propan-2-one (16) as a colorless solid (1.42 g, 4.18 mmol, 94.4%).

TLC $R_f$=0.41 (n-hexane/ethyl acetate=7/1);
$^1$H NMR (400 MHz, CDCl$_3$) δ 3.90 (s, 2H), 3.91 (s, 2H), 6.96-7.01 (AA'BB', 2H), 7.66-7.71 (AA'BB', 2H).

Comparative Synthesis Example 1-3

1-Bromo-3-(4-iodophenyl)propan-2-one (16) (460 mg, 1.36 mmol) was dissolved in acetonitrile (4 mL) and to this was added silver nitrate (596 mg, 3.51 mmol) dissolved in acetonitrile (4 mL), and stirred overnight (13 h) at room temperature. The reaction solution was filtered through Celite and the filtrate was washed sequentially with water (×1) and saturated brine (×1), and then the organic layer was dried over anhydrous sodium sulfate. After filtration, the filtrate was concentrated under reduced pressure to give 3-(4-iodophenyl)-2-oxopropyl nitrate (17) as a colorless solid (490 mg, <1.36 mmol, <100%), which was used in the next reaction without further purification.

TLC $R_f$=0.26 (tailing) (n-hexane/ethyl acetate=5/1);
$^1$H NMR (400 MHz, CDCl$_3$) δ 3.73 (s, 2H), 4.97 (s, 2H), 6.96-7.00 (AA'BB', 2H), 7.68-7.73 (AA'BB', 2H).

Comparative Synthesis Example 1-4

3-(4-Iodophenyl)-2-oxopropyl nitrate (17) (450 mg) was dissolved in dimethylsulfoxide (20 mL) and to this was added sodium acetate trihydrate (211 mg, 1.55 mmol), and stirred for an hour at room temperature. To this was added water and the product was extracted with diethyl ether (×3). The organic layer was washed sequentially with water (×1), saturated aqueous solution of sodium bicarbonate (×1) and saturated brine (×1), and then dried over anhydrous sodium sulfate. After filtration, the filtrate was concentrated under reduced pressure to give 3-(4-iodophenyl)-2-oxopropanal (18) as an orange solid (346 mg, <1.26 mmol, <90.1%), which was used in the next reaction without further purification.

TLC $R_f$=0.43 (tailing) (n-hexane/ethyl acetate=5/1);

Comparative Synthesis Example 1-5

Under an argon atmosphere, 3-(4-iodophenyl)-2-oxopropanal (18) (343 mg, 1.25 mmol) was dissolved in 1,4-dioxane (2.0 mL) and water (0.4 mL). To this was added coelenteramine (233 mg, 834 mmol) and, after cooling to 0° C., conc. hydrochloric acid (0.20 mL) was added thereto, and then stirred for 6 h at 100° C. After cooling to room temperature, the mixture was extracted with dichloromethane and a small quantity of methanol (×4). The organic layer was washed sequentially with water (×1) and saturated brine (×1) and then dried over anhydrous sodium sulfate. After filtration, the organic layer was concentrated under reduced pressure and the residue was purified in an argon flow by silica gel flash chromatography (deaerated dichloromethane/deaerated methanol=50/1-10/1). The solid obtained was further reprecipitated (n-hexane/acetone) to give i-coelenterazine (15, i-CTZ) as an ocher powder (52.6 mg, 98.6 µmol, 11.8%).

n-CTZ, i-CTZ, me-CTZ, et-CTZ, cf3-CTZ, meo-CTZ, 3me-CTZ, 3meo-CTZ, αmeh-CTZ and 3iso-CTZ prepared above were used for the production of semi-synthetic aequorins and for the analysis of substrate specificity of each luciferase, and so on, in the following EXAMPLES. In addition, coelenterazine (CTZ) and h-coelenterazine (h-CTZ) were used in the following EXAMPLES. CTZ and h-CTZ used were those manufactured by Chisso Corporation.

Hereinafter, CTZ, or h-CTZ, n-CTZ, me-CTZ, et-CTZ, cf3-CTZ, meo-CTZ, 3me-CTZ, 3meo-CTZ, αmeh-CTZ, 3iso-CTZ or i-CTZ is sometimes referred to as coelenterazine or analogs thereof.

Example 1

Production of Semi-synthetic Aequorins for Substrate Specificity Analysis and Measurement of Luminescence Activity To produce the following semi-synthetic aequorins, the recombinant apoaequorin manufactured by Chisso Corporation was used. This recombinant apoaequorin was obtained by expressing and purifying according to the method described in Inouye, S, and Sahara, Y. Protein Express. Purif. (2007) 53: 384-389, using piP-H-HE constructed from the expression vector piP-HEAE, which is described in the same literature by inserting histidine sequence therein.

(1) Production of Semi-synthetic Aequorins

One microliter of 2-mercaptoethanol and 1.31 µg of recombinant apoacquorin solution (made by Chisso Corp.) were added to and mixed with 1 ml of 30 mM Tris-HCl (pH 7.6) containing 10 mM EDTA. Subsequently, 1 µl of a solution of coelenterazine or its analog in ethanol was added and the mixture was allowed to stand at 4° C. to convert into a semi-synthetic aequorin. In order to confirm the regeneration time and regeneration efficiency from apoaequorin to the semi-synthetic aequorin, the luminescence activity was assayed at the respective points of the regeneration process (at the respective points of 0.5, 1, 1.5, 2, 3 and 18 hours from the start of regeneration). The results are shown in FIG. 1.

As shown in FIG. 1, it is demonstrated that coelenterazine analogs of the present invention (me-CTZ, et-CTZ, cf3-CTZ, meo-CTZ, 3me-CTZ, 3meo-CTZ, αmeh-CTZ and 3iso-CTZ) can be luminescence substrates for semi-synthetic aequorins, though luminescent intensities are different.

2) Method for Measuring the Luminescence Activity

Specifically, the luminescence activity described above was measured as follows. The luminescence reaction was started by adding 100 µl of 50 mM Tris-HCl (pH 7.6) containing 50 mM calcium chloride solution to 2 μl of a solution of the semi-synthetic aequorin at each regeneration process. The luminescence activity was measured for 10 seconds with a luminometer Luminescencer-PSN AB2200 (manufactured by Atto Co., Ltd.). The measured values were represented as the maximum intensity ($I_{max}$) of luminescence. The emission for 60 seconds was integrated, which was made a luminescence capacity.

Example 2

Figure 2:
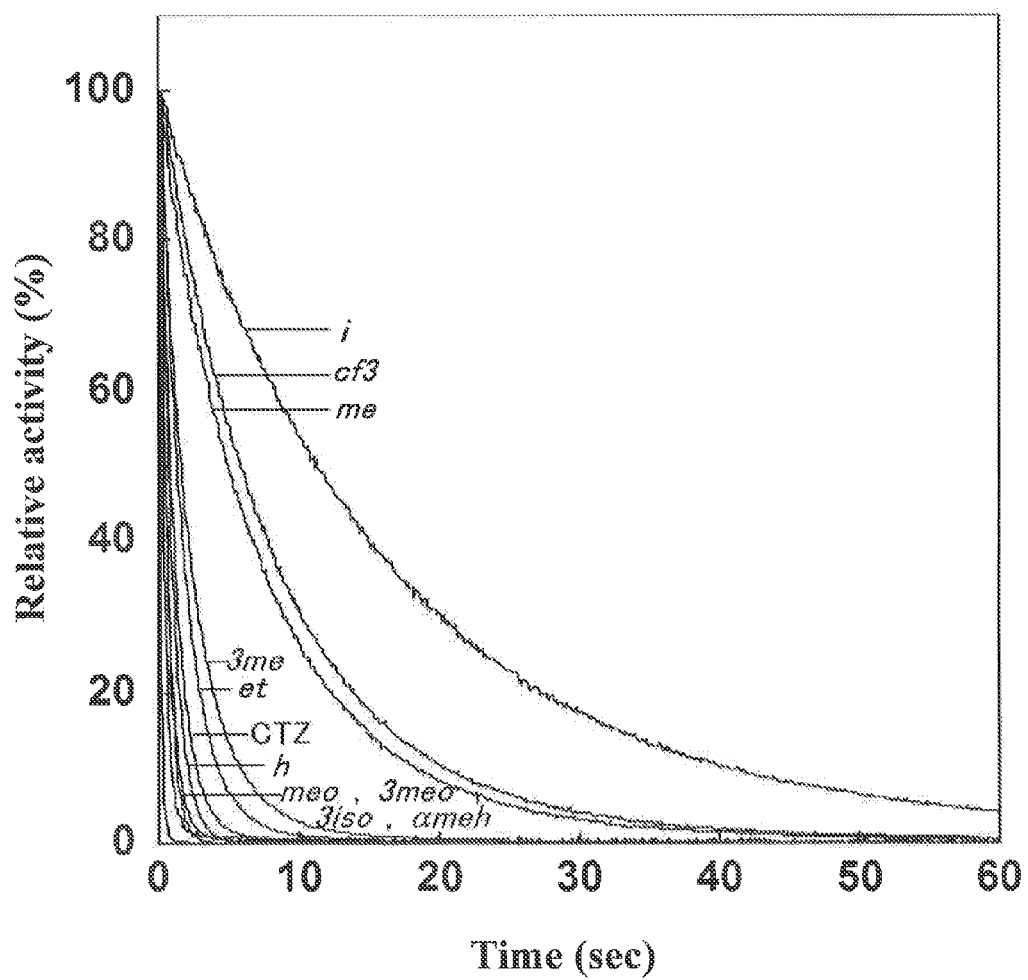
FIG. 2 shows the luminescence patterns for semi-synthetic aequorins.

Method for Measuring the Luminescence Patterns and Half Decay Time of Semi-synthetic Aequorins A solution of the regenerated semi-synthetic aequorin was diluted to 10-fold with 20 mM Tris-HCl (pH 7.6) containing 0.1% BSA (manufactured by Sigma), 0.01 mM EDTA and 150 mM NaCl. The dilution was dispensed into a 96-well microplate (Nunc #236108) in 5 μl/well. The luminescence reaction was started by injecting 100 μl/well of 50 mM Tris-HCl (pH 7.6) containing 50 mM calcium chloride solution using a luminescence plate reader Centro LB960 (manufactured by Berthold). The luminescence patterns for 60 seconds were measured to determine the half decay time of luminescence (time period to reach the half of the maximum luminescence intensity). The results are shown in FIG. 2 and summarized in TABLE 1 below.

TABLE 1

Luminescence properties of semi-synthetic aequorins

| Coelenterazine derivative | Luminescence activity $I_{max}$ (%) | Luminescence capacity 60 sec (%) | Half decay time sec. | Maximum emission wavelength $\lambda_{max}$ (nm) |
|---|---|---|---|---|
| Coelenterazine | 100.0 | 100.0 | 0.81 | 465.5 |
| h- | 87.9 | 70.1 | 0.69 | 465.5 |
| et- | 27.3 | 44.1 | 1.21 | 472.0 |
| n- | 3.6 | 24.0 | 4.71 | 467.0 |
| cf3- | 6.3 | 48.6 | 5.95 | 473.5 |
| i- | 5.0 | 65.3 | 11.42 | 472.0 |
| meo- | 22.3 | 60.1 | 1.63 | 469.0 |
| 3meo- | 64.9 | 35.6 | 0.52 | 466.0 |
| me- | 5.8 | 45.0 | 5.00 | 469.5 |
| 3me- | 35.0 | 21.2 | 0.51 | 466.0 |
| αmeh- | 2.2 | 0.9 | 0.35 | 467.5 |
| 3iso- | 51.6 | 13.4 | 0.24 | 464.0 |

As shown in FIG. 2 and TABLE 1, the half decay time of luminescence was longer than CTZ especially with the semi-synthetic aequorins using me-CTZ and cf3-CTZ as the luminescence substrates. Accordingly, $Ca^{2+}$ can be measured by light being allowed to be emitted slowly, not by instantaneous emission. This indicates that the semi-synthetic aequorins wherein me-CTZ and cf3-CTZ are used as the luminescence substrates are well suited for applications to a high-precision assay system using as an indicator $Ca^{2+}$ level change in the system, in the same manner as in the semi-synthetic aequorins wherein i-CTZ and n-CTZ conventionally known as aequorins having slow half decay time are used as the luminescence substrates.

Example 3

Method for Measuring the Emission Spectra of Semi-synthetic Aequorins

Figure 3:
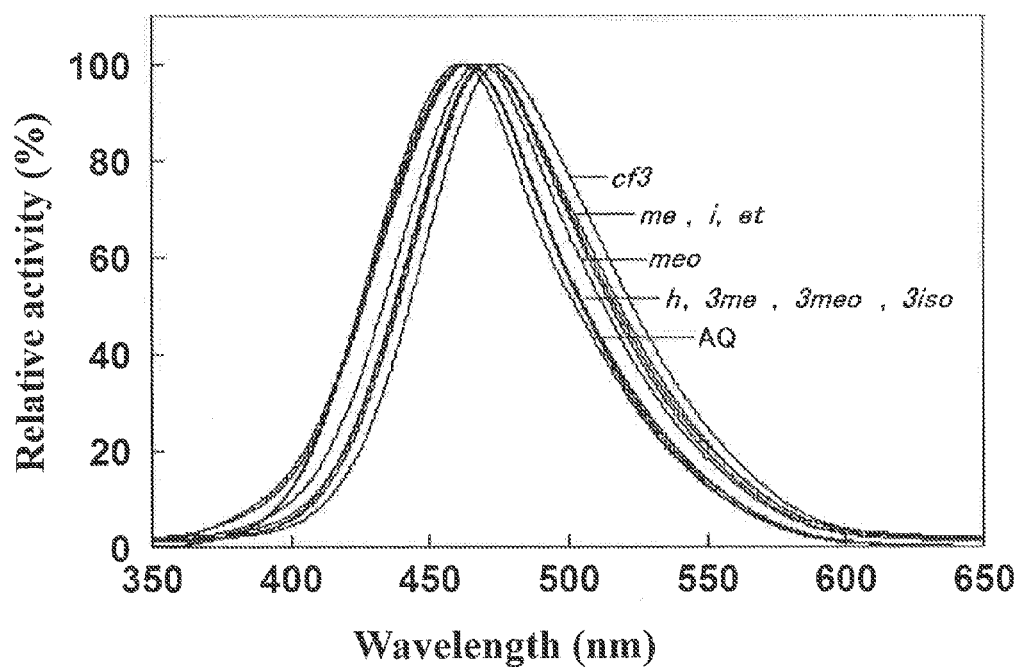
FIG. 3 shows the emission spectra of semi-synthetic aequorins by addition of calcium ions.

In a quartz cell with an optical path length of 10 mm, 1 ml of 50 mM Tris-HCl (pH 7.6) containing 1 mM EDTA and 100 μl (100 μg protein) of a solution of the regenerated semi-synthetic aequorin were charged and they were mixed. Subsequently, 100 μl of 50 mM Tris-HCl (pH 7.6) containing 0.1 ml of 10 mM calcium chloride solution was added to the mixture to trigger the luminescence reaction. The spectra were measured on a spectrofluorimeter (FP-6500, manufactured by JASCO Corporation) with the excitation source turned off. The measurement conditions used were as follows: band width, 20 nm; response, 0.5 second and scan speed, 2000 nm/min at 22 to 25° C. The results are shown in FIG. 3. In FIG. 3, AQ denotes semi-synthetic aequorin, for which coelenterazine is the luminescence substrate.

As shown in FIG. 3, the semi-synthetic aequorins, for which me-CTZ, et-CTZ, cf3-CTZ, meo-CTZ, 3me-CTZ, 3meo-CTZ and 3iso-CTZ are the luminescence substrates exhibit different emission spectra from those of known coelenterazine analogs (h-CTZ and i-CTZ).

Example 4

Preparation of Standard Calcium Solution

By dissolving 1 ml of 1 g/L standard calcium carbonate solution (manufactured by Wako Pure Chemical Industry) in 9 ml of 50 mM Tris-HCl (pH 7.6), $10^{-3}$ M calcium carbonate solution was prepared.

One milliliter of the resulting $10^{-3}$ M calcium carbonate solution was taken and added to 9 ml of 50 mM Tris-HCl (pH 7.6) to prepare $10^{4}$M calcium carbonate solution. Furthermore, 3 ml of the resulting $10^{4}$M calcium carbonate solution was taken and added to 6 ml of 50 mM Tris-HCl (pH 7.6) to prepare $3 \times 10^{-4}$ M calcium carbonate solution. Next, 1 ml of the resulting $10^{-4}$ M calcium carbonate solution was taken and added to 9 ml of 50 mM Tris-HCl (pH 7.6) to prepare $10^{-5}$ M calcium carbonate solution. Further 3 ml of the resulting $10^{-5}$ M calcium carbonate solution was taken and 6 ml of 50 mM Tris-HCl (pH 7.6) was added to prepare $3 \times 10^{-5}$ M calcium carbonate solution. The dilution series was prepared by the serial process above to prepare standard calcium solution of $10^{-3}$ M to $10^{-8}$ M.

Example 5

Production of Semi-synthetic Aequorin for Detecting Calcium Levels

After 5 mg of the recombinant apoaequorin (manufactured by Chisso Corp.) was dissolved in 5 ml of 50 mM Tris-HCl (pH 7.6) containing 10 mM DTT and 30 mM EDTA, 100 μg of a solution of 1.2-fold equivalent of coelenterazine analog in ethanol was added thereto. The mixture was allowed to stand at 4° C. overnight to convert into the semi-synthetic aequorin. The semi-synthetic aequorin obtained was concentrated using Amicon Ultra-4 (manufactured by Millipore, molecular weight cut off, 10,000). Subsequently, the concentrate was washed 3 times with 3 ml of 30 mM Tris-HCl (pH 7.6) containing 0.05 mM EDTA to remove an excess of coelenterazine analog and make the EDTA concentration 0.05 mM.

This semi-synthetic aequorin solution (2.5 mg/ml) was diluted with 20 mM Tris-HCl (pH 7.6) containing 0.1% BSA (manufactured by Sigma), 0.01 mM EDTA and 150 mM NaCl.

Example 6

Preparation of Calcium Standard Curve

The calcium standard solution prepared as described above was dispensed into a 96-well microplate (Nunc #236108) in 50 μl/well, and the semi-synthetic aequorin solution diluted was injected in 10 µl/well. The luminescence intensity was measured for 60 seconds using a luminescence plate reader Centro LB960 (manufactured by Berthold) and expressed in terms of the maximum luminescence intensity ($I_{max}$). The luminescence intensity was measured for each semi-synthetic aequorin in the same fashion. Based on the maximum luminescence intensity ($I_{max}$) obtained, the calcium standard curve for each semi-synthetic aequorin was prepared.

Figure 4:
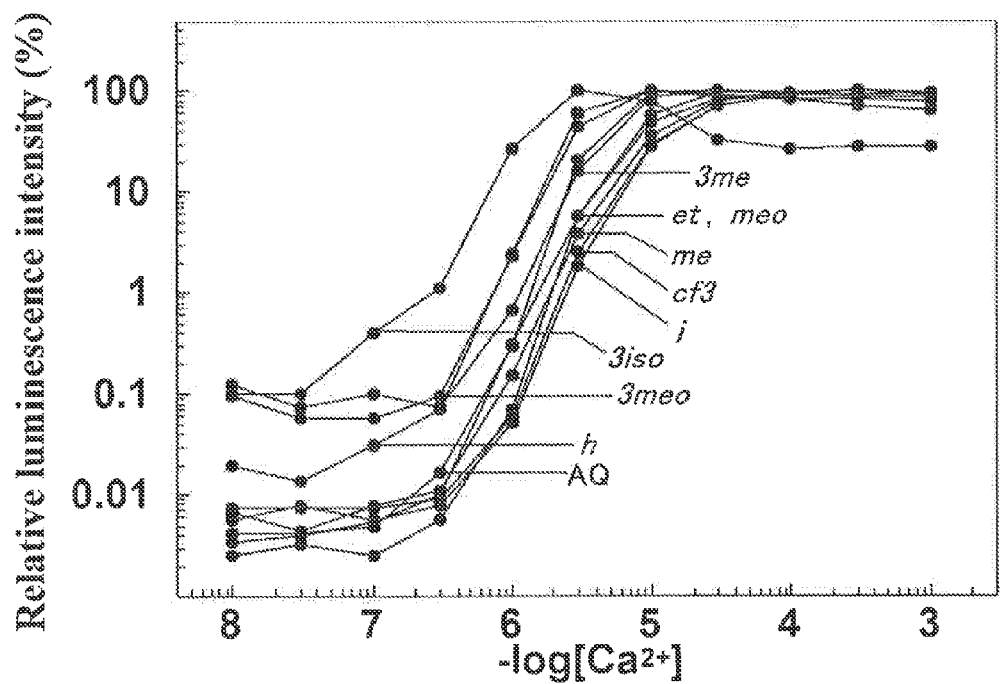
FIG. 4 shows the relationship between the initial luminescence intensity of semi-synthetic aequorins and calcium ion levels.

The results are shown in FIG. 4.

As shown in FIG. 4, it is observed that the photoproteins of the present invention can be used for the detection, quantification or the like of calcium ions, since the calcium standard curves can be prepared by using the semi-synthetic aequorins, which were prepared from coelenterazine analogs of the present invention (me-CTZ, et-CTZ, cf3-CTZ, meo-CTZ, 3me-CTZ, 3meo-CTZ, αmeh-CTZ and 3iso-CTZ).

Example 7

Method for Analyzing the Substrate Specificity and Measuring the Luminescence Activity of the 19 kDa Protein from *Oplophorus* luciferase The 19 kDa protein of *Oplophorus* luciferase was purified by the method described in Inouye, S, and Sasaki, S. Protein Express, and Purif. (2007) 56: 261-268, which was provided for use.

After 1 µl of the 19 kDa protein (2.3 mg/ml) of *Oplophorus* luciferase containing 1 mM DTT was dissolved in 100 µl of 30 mM Tris-HCl (pH 7.6) containing 10 mM EDTA, 1 µl of a solution of coelenterazine or its analog in ethanol (1 µg/µl) was mixed with the solution to trigger the luminescence reaction. The luminescence activity was measured for 60 seconds using a luminometer Luminescencer-PSN AB2200 (manufactured by Atto Co., Ltd.). The luminescence activity was measured 3 times and expressed as the maximum intensity ($I_{max}$) of luminescence. The emission for 10 seconds was integrated, which was made a luminescence capacity.

Figure 5:
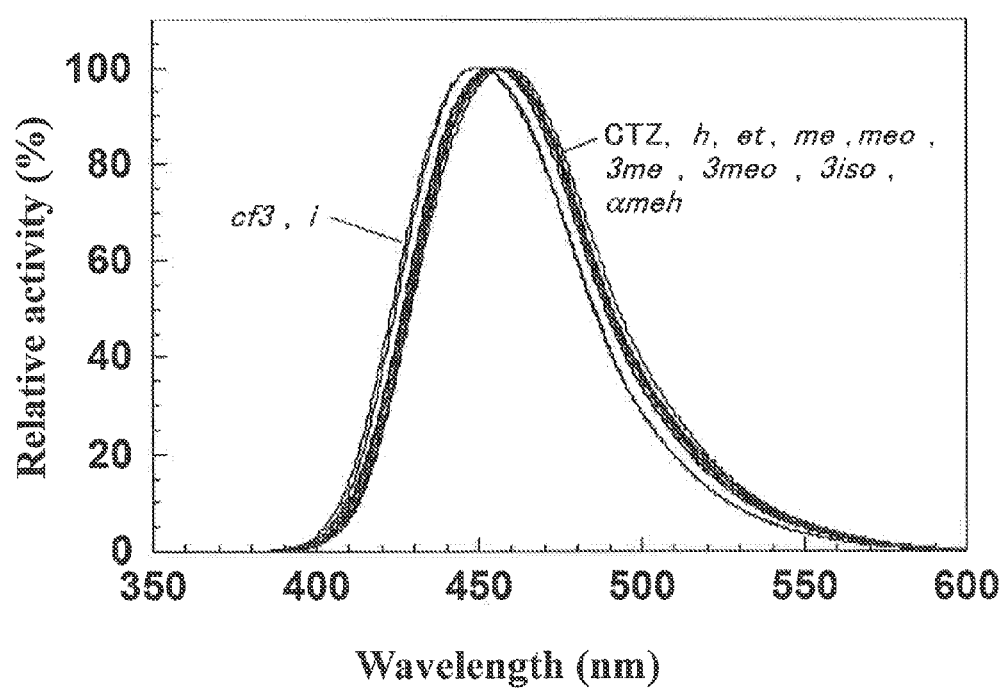
FIG. 5 shows the emission spectra of *Oplophorus* luciferase by addition of coelenterazine or its analogs.

The emission spectra were assayed by adding 5 µg of coelenterazine or its analog (dissolved in 5 µl of ethanol) to 990 µl of 30 mM Tris-HCl (pH 7.6) containing 10 mM EDTA and then adding 20 µl (46 µg) of *Oplophorus* luciferase thereby to trigger luminescence. The spectra were measured on a spectrofluorimeter (FP-6500, manufactured by JASCO Corporation) with the excitation source turned off, under band width of 20 nm, response of 0.5 second and scan speed of 2000 nm/min at 22 to 25° C. The results of luminescence activity, luminescence capacity and maximum emission wavelength are shown in TABLE 2 below. The emission spectrum charts are shown in FIG. 5.

TABLE 2

Substrate specificity and maximum emission wavelength of *Oplophorus* luciferase using coelenterazine derivatives

| Coelenterazine analog | Luminescence activity $I_{max}$ (%) | Luminescence capacity 10 secs. (%) | Maximum emission wavelength $\lambda_{max}$ (nm) |
| --- | --- | --- | --- |
| Coelenterazine | 100.0 | 100.0 | 457.0 |
| h- | 68.4 | 110.2 | 456.5 |
| i- | 32.3 | 53.8 | 450.0 |
| et- | 21.1 | 39.5 | 454.0 |
| cf3- | 49.5 | 68.2 | 450.5 |
| me- | 46.6 | 82.7 | 454.4 |
| 3me- | 80.0 | 122.8 | 455.5 |
| meo- | 68.1 | 108.6 | 454.5 |
| 3meo- | 189.1 | 204.7 | 455.5 |

TABLE 2-continued

Substrate specificity and maximum emission wavelength of *Oplophorus* luciferase using coelenterazine derivatives

| Coelenterazine analog | Luminescence activity $I_{max}$ (%) | Luminescence capacity 10 secs. (%) | Maximum emission wavelength $\lambda_{max}$ (nm) |
| --- | --- | --- | --- |
| αmeh- | 15.6 | 19.0 | 457.0 |
| 3iso- | 78.2 | 71.8 | 458.0 |

As shown in TABLE 2, it is observed that me-CTZ, et-CTZ, cf3-CTZ, meo-CTZ, 3me-CTZ, 3meo-CTZ, αme-CTZ and 3iso-CTZ become relatively good luminescence substrates for *Oplophorus* luciferase. Especially, 3me-CTZ, 3meo-CTZ and 3iso-CTZ exhibit high luminescence activity and/or luminescence capacity when compared to known h-CTZ.

Example 8

Method for Analyzing the Substrate Specificity and Measuring the Luminescence Activity of *Gaussia* luciferase

*Gaussia* luciferase was purified by the method described in JPA 2008-099669 and provided for use.

Figure 6:
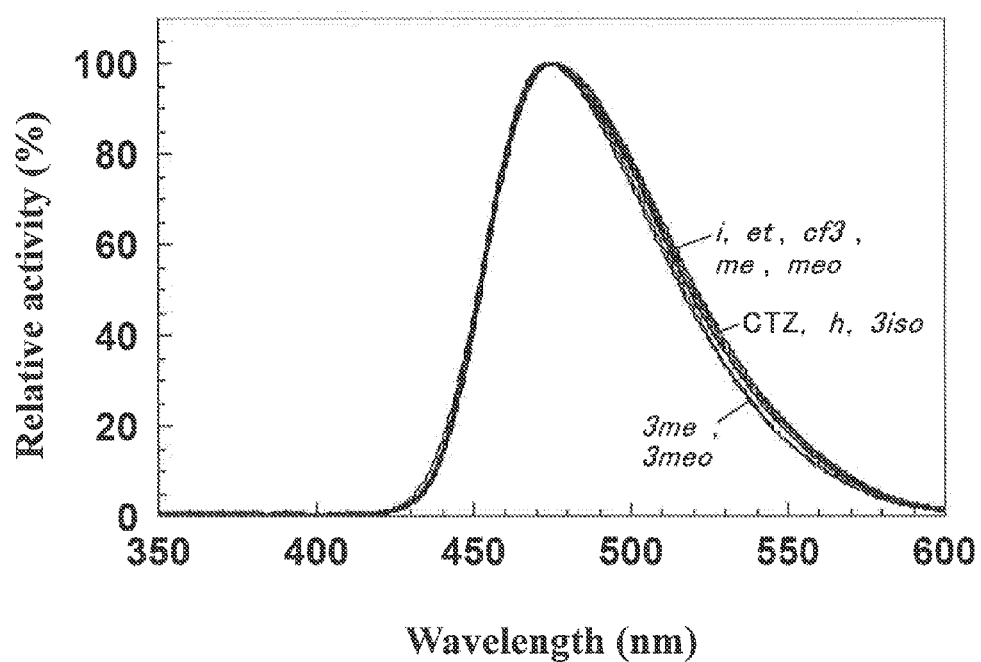
FIG. 6 shows the emission spectra of *Gaussia* luciferase by addition of coelenterazine or its analogs.

After 1 µl of *Gaussia* luciferase (0.16 mg/ml) was dissolved in 100 µl of phosphate buffered saline (manufactured by Sigma Inc.) containing 0.01% Tween 20 (manufactured by Sigma Inc.) and 10 mM EDTA, 1 µl of a solution of coelenterazine or its analog dissolved in ethanol (1 µg/Id) was mixed with the solution to trigger the luminescence reaction. The luminescence activity was measured for 10 seconds using a luminometer Luminescencer-PSN AB2200 (manufactured by Atto Co., Ltd.). The luminescence activity was measured 3 times and expressed as the maximum intensity ($I_{max}$) of luminescence. The emission spectra were assayed by adding 5 µg of coelenterazine or its analog (dissolved in 5 µl of ethanol) to 1000 µl of phosphate buffered saline containing 10 mM EDTA and 0.01% Tween 20, and then adding 1 µl (0.23 µg) of *Gaussia* luciferase thereby to trigger luminescence. The spectra were measured using a spectrofluorimeter (FP-6500, manufactured by JASCO Corporation) with the excitation source turned off, under band width of 20 nm, response of 0.5 second and scan speed of 2000 nm/min of 20 nm, response of 0.5 second and scan speed of 2000 nm/min at 22 to 25° C. The results of luminescence activity, luminescence capacity and maximum emission wavelength are shown in TABLE 3 below. The emission spectrum charts are shown in FIG. 6.

TABLE 3

Substrate specificity and maximum emission wavelength of *Gaussia* luciferase using coelenterazine derivatives

| Coelenterazine analog | Luminescence activity $I_{max}$ (%) | Luminescence capacity 10 secs. (%) | Maximum emission wavelength $\lambda_{max}$ (nm) |
| --- | --- | --- | --- |
| Coelenterazine | 100.0 | 100.0 | 473.0 |
| h- | 5.8 | 7.2 | 474.0 |
| i- | 0.9 | 1.3 | 475.0 |
| et- | 0.9 | 1.1 | 476.0 |
| cf3- | 0.8 | 0.7 | 476.5 |
| me- | 4.5 | 5.9 | 475.0 |
| 3me- | 2.6 | 2.1 | 475.5 |
| meo- | 13.6 | 15.5 | 475.5 |
| 3meo- | 3.8 | 3.1 | 474.5 |

TABLE 3-continued

Substrate specificity and maximum emission wavelength of *Gaussia* luciferase using coelenterazine derivatives

| Coelenterazine analog | Luminescence activity $I_{max}$ (%) | Luminescence capacity 10 secs. (%) | Maximum emission wavelength $\lambda_{max}$ (nm) |
|---|---|---|---|
| αmeh- | >0.01 | >0.01 | 473.0 |
| 3iso- | 14.3 | 7.4 | 477.0 |

*Gaussia* luciferase exhibits high substrate specificity, and any coelenterazine analog which acts as its luminescence substrate is unknown to date. As shown in TABLE 3, it is demonstrated that me-CTZ and 3iso-CTZ become effective luminescence substrates for *Gaussia* luciferase.

Example 9

Method for Analyzing the Substrate Specificity of *Renilla* luciferase and Measuring the Luminescence Activity

*Renilla* luciferase was purified by the method described in Inouye, S. & Shimomura, O. Biochem. Biophys. Res. Commun. (1997) 233: 349-353, which was provided for use.

Figure 7:
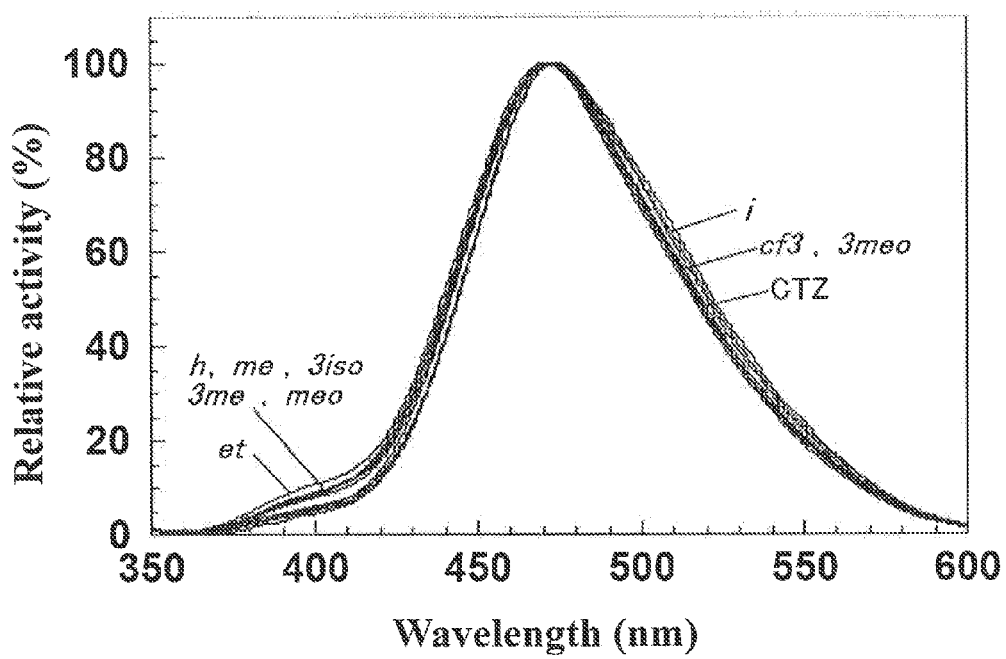
FIG. 7 shows the emission spectra of *Renilla* luciferase by addition of coelenterazine or its analogs.

After 1 μl of *Renilla* luciferase (0.45 mg/ml) was dissolved in 100 pd of 30 mM Tris-HCl (pH 7.6) containing 10 mM EDTA, 1 μl of a solution of coelenterazine or its analog in ethanol (1 μg/μl) was mixed with the solution to trigger the luminescence reaction. The luminescence activity was measured 3 times using a luminometer Luminescencer-PSN AB2200 (manufactured by Atto Co., Ltd.) and expressed as the maximum intensity ($I_{max}$) of luminescence. Emission was started by adding 5 μg of coelenterazine or its analog (dissolved in 5 μl of ethanol) to 1000 μl of 30 mM Tris-HCl (pH 7.6) containing 10 mM EDTA and 5 μl (2.3 μg) of *Renilla* luciferase. The emission spectra were measured on a spectrofluorimeter (FP-6500, manufactured by JASCO Corporation) with the excitation source turned off under band width of 20 nm, response of 0.5 second and scan speed of 2000 nm/min at 22 to 25° C. The results of luminescence activity, luminescence capacity and maximum emission wavelength are shown in TABLE 4 below. The emission spectrum charts are shown in FIG. 7.

TABLE 4

Substrate specificity and maximum emission wavelength of *Renilla* luciferase using coelenterazine derivatives

| Coelenterazine analog | Luminescence activity $I_{max}$ (%) | Luminescence capacity 10 secs. (%) | Maximum emission wavelength $\lambda_{max}$ (nm) |
|---|---|---|---|
| Coelenterazine | 100.0 | 100.0 | 472.5 |
| h- | 78.6 | 90.3 | 472.5 |
| i- | 0.2 | 0.3 | 473.0 |
| et- | 0.5 | 0.3 | 471.0 |
| cf3- | 0.8 | 0.8 | 474.5 |
| me- | 6.6 | 7.0 | 472.0 |
| 3me- | 12.7 | 13.1 | 471.5 |
| meo- | 8.0 | 8.6 | 472.5 |
| 3meo- | 26.0 | 31.6 | 473.5 |
| αmeh- | 0.0 | 0.0 | N.D.* |
| 3iso- | 25.7 | 27.5 | 472.0 |

N.D.: not detected

As shown in TABLE 4, it is demonstrated that me-CTZ, meo-CTZ, 3meo-CTZ and 3iso-CTZ can be substrates for *Renilla* luciferase.

[Sequence Listing Free Text]
[SEQ ID NO: 1] Nucleotide sequence of natural apoaequorin
[SEQ ID NO: 2] Amino acid sequence of natural apoaequorin
[SEQ ID NO: 3] Nucleotide sequence of natural apoclytin-I
[SEQ ID NO: 4] Amino acid sequence of natural apoclytin-I
[SEQ ID NO: 5] Nucleotide sequence of natural apoclytin-II
[SEQ ID NO: 6] Amino acid sequence of natural apoclytin-II
[SEQ ID NO: 7] Nucleotide sequence of natural apomitrocomin
[SEQ ID NO: 8] Amino acid sequence of natural apomitrocomin
[SEQ ID NO: 9] Nucleotide sequence of natural apobelin
[SEQ ID NO: 10] Amino acid sequence of natural apobelin
[SEQ ID NO: 11] Nucleotide sequence of natural apobervoin
[SEQ ID NO: 12] Amino acid sequence of natural apobervoin
[SEQ ID NO: 13] Nucleotide sequence of *Renilla* luciferase
[SEQ ID NO: 14] Amino acid sequence of *Renilla* luciferase
[SEQ ID NO: 15] Nucleotide sequence of *Oplophorus* luciferase
[SEQ ID NO: 16] Amino acid sequence of *Oplophorus* luciferase
[SEQ ID NO: 17] Nucleotide sequence of *Gaussia* luciferase
[SEQ ID NO: 18] Amino acid sequence of *Gaussia* luciferase

The invention claimed is:

1. A method for producing a calcium-binding photoprotein, which comprises contacting the compound represented by the general formula (1) below:

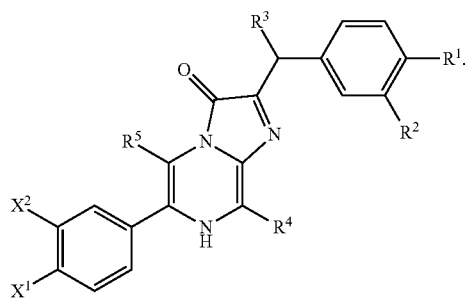

(1)

wherein:

$R^1$ is (a) hydrogen, (b) hydroxy, (c) an alkyl having 1 to 4 carbon atoms which may optionally be substituted with an alicyclic group, or (d) trifluoromethyl;

$R^2$ is (a) hydrogen, (b) hydroxy, (c) a halogen, (d) an alkyl having 1 to 4 carbon atoms which may optionally be substituted with an alicyclic group, (e) trifluoromethyl or (f) an alkoxyl;

$R^3$ is (a) hydrogen, (b) an alkyl having 1 to 4 carbon atoms which may optionally be substituted with an alicyclic group, or (c) an alkoxyl;

$R^4$ is a substituted or unsubstituted benzyl;

$R^5$ is (a) hydrogen or (b) a substituted or unsubstituted alkyl;

$X^1$ is (a) hydrogen or (b) hydroxy; and $X^2$ is (a) hydrogen or (b) hydroxy;

with the proviso that when $R^2$ and $R^3$ are hydrogen, $R^1$ is (a) an alkyl having 1 to 4 carbon atoms which may optionally be substituted with an alicyclic group, or (b) trifluoromethyl, when $R^1$ and $R^3$ are hydrogen, $R^2$ is (a) hydroxy, (b) an alkyl having 1 to 4 carbon atoms which may optionally be substituted with an alicyclic group, (c) trifluoromethyl, or (d) an alkoxyl, and, when $R^1$ and $R^2$ are hydrogen, $R^3$ is (a) an alkyl having 1 to 4 carbon atoms which may optionally be substituted with an alicyclic group, or (b) an alkoxyl, with an apoprotein of the calcium-binding photoprotein to obtain the calcium-binding photoprotein.

* * * * *